US010301633B2

(12) United States Patent
Daran et al.

(10) Patent No.: US 10,301,633 B2
(45) Date of Patent: May 28, 2019

(54) UREOHYDROLASES AS DOMINANT SELECTABLE MARKERS IN YEAST

(71) Applicant: HEINEKEN SUPPLY CHAIN B.V., Amsterdam (NL)

(72) Inventors: Jean-Marc Georges Daran, Delft (NL); Jacobus Thomas Pronk, Delft (NL); Gabriele Romagnoli, Delft (NL)

(73) Assignee: HEINEKEN SUPPLY CHAIN B.V., Amsterdam (NL)

( * ) Notice: Subject to any disclaimer, the term of this patent is extended or adjusted under 35 U.S.C. 154(b) by 0 days.

(21) Appl. No.: 15/301,599

(22) PCT Filed: Apr. 13, 2015

(86) PCT No.: PCT/NL2015/050238
§ 371 (c)(1),
(2) Date: Oct. 3, 2016

(87) PCT Pub. No.: WO2015/156675
PCT Pub. Date: Oct. 15, 2015

(65) Prior Publication Data
US 2017/0298368 A1    Oct. 19, 2017

(30) Foreign Application Priority Data

Apr. 11, 2014 (NL) .................................. 2012608

(51) Int. Cl.
*C12N 15/81* (2006.01)
*C12Q 1/04* (2006.01)
*C12N 9/78* (2006.01)

(52) U.S. Cl.
CPC ............ *C12N 15/81* (2013.01); *C12N 9/78* (2013.01); *C12Q 1/04* (2013.01); *C12Y 305/03007* (2013.01); *G01N 2333/395* (2013.01); *G01N 2333/978* (2013.01)

(58) Field of Classification Search
None
See application file for complete search history.

(56) References Cited

U.S. PATENT DOCUMENTS

2012/0052582 A1    3/2012 Benjamin

OTHER PUBLICATIONS

Database UniProt [Online], Aug. 16, 2004, SubName: Full=KLLA0F27995p: XP002731320, retrieved from EPI accession No. UNIPROT: Q6CIB4, Database accession No. Q6CIB4, pp. 1-2.
Dujon, B. et al., "Genome Evolution in Yeasts", Nature, Nature Publishing Group, United Kingdom, vol. 430, No. 6995, Jul. 1, 2004, pp. 35-44, XP002730312, ISSN: 0028-0836.
Nielsen, M. et al., "Efficient PCR-Based Gene Targeting With a Recyclable Marker for Aspergillus Nidulans", Fungal Genetics and Biology, San Diego, California, USA, vol. 43, No. 1, Nov. 11, 2005-Jan. 1, 2006, pp. 54-64, XP024918908, ISSN: 1087-1845.
Tan, G. et al., "SMC, a Simple Method to Rapidly Assemble Multiple Fragments Into One Construct", Frontiers in Bioscience 2010, vol. 2, Jan. 1, 2010, pp. 1105-1114, XP009180831, ISSN: 1945-0508.
Lunblad, V. et al., "Manipulation of Cloned Yeast DNA", Current Protocols in Molecular Biology, May 1, 2001, John Wiley & Sons, Inc., Hoboken, New Jersey, USA, XP055147296, ISBN: 978-0-47-114272-0, pp. 1-14.
Rothstein, R. et al., "Targeting, Disruption, Replacement and Allele Rescue: Integrative DNA Transformation in Yeast", Methods in Enzymology, Academic Press, US, vol. 1974, Jan. 1, 1991, pp. 281-301, XP002958952, ISSN: 0076-6879.
Fairhead, C. et al., "New Vectors for Combinatorial Deletions in Yeast Chromosomes and for Gap Repair Cloning Using 'Split-Marker' Recombination", Yeast, vol. 12, No. 14, Jan. 1, 1996, pp. 1439-1458.
Kashyap, D. et al., "A Novel Selectable Marker Based on Arginase Expression", Enzyme and Microbial Technology, Stoneham, MA, USA, vol. 51, No. 1, Apr. 5, 2012, pp. 53-58, XP028486368, ISSN: 0141-0229.
Klein, R.D. et al., "Reconstitution of a Bacterial/Plant Polyamine Biosynthesis Pathway in *Saccharomyces cerevisiae*", Microbiology, Society for General Microbiology, Reading, GB, vol. 145, No. 2, Feb. 1, 1999, pp. 301-307, XP002232122, ISSN: 1350-0872.
Sanjay, K. Mistry et al., "Cloning of Human Agmatinase. An Alternate Path for Polyamine Synthesis Induced in Liver by Hepatitis B Virus", American Journal of Physiology—Gastrointestinal and Liver Physiology, Feb. 1, 2002, pp. 375-381, XP055147206.
Romagnoli, G., et al., "An Alternative, Arginase-Independent Pathway for Arginine Metabolism in K Luyveromyces Lactis Involves Guanidinobutyrase as a Key Enzyme", Molecular Microbiology, vol. 93, No. 2, Jul. 23, 2014, pp. 369-389, XP 055147208, ISSN: 0950-382X.
Solis-Escalante, D. et al., "Efficient Simultaneous Excision of Multiple Selectable Marker Cassettes Using I-SceI-Induced Double-Strand DNA Breaks in *Saccharomyces Cerevisiae*", FEMS Yeast Research, vol. 14, No. 5, Jun. 27, 2014, pp. 741-754, XP055147302, ISSN: 1567-1356.
Kurtzman, C., "Phylogenetic circumscription of *Saccharomyces*, *Kluyveromyces* and other members of the *Saccharomycetaceae*, and the proposal of the new genera *Lachancea*, *Nakaseomyces*, *Naumovia*, *Vanderwaltozyma* and *Zygotorulaspora*", FEMS Yeast Research, vol. 4, 2003, pp. 233-245.

Primary Examiner — Nancy J Leith
(74) Attorney, Agent, or Firm — Pearne & Gordon LLP

(57) ABSTRACT

The invention relates to a nucleic acid molecule encoding a novel selection marker. Said marker is a guanidinobutyrase from *Kluyveromyces lactis*, which, when expressed in *Saccharomyces*, allows the growth of the yeast in the presence of guanidinobutyrate as the sole nitrogen source. Said marker can be used in a method for producing a microorganism having an altered genome. The invention further relates to a set of constructs, comprising a first construct comprising a recognition site for an endonuclease, a first region of homology with a target gene of a microorganism, and a first part of a nucleotide sequence encoding the selection marker, and a second construct comprising a second part of the nucleotide sequence encoding the selection marker, a second region of homology with the target gene of the microorganism, and a copy of the endonuclease recognition site. The invention further relates to methods for altering a target gene in a microorganism, to methods for producing a microorganism, and to microorganisms that are produced by the methods of the invention.

Figure 1:
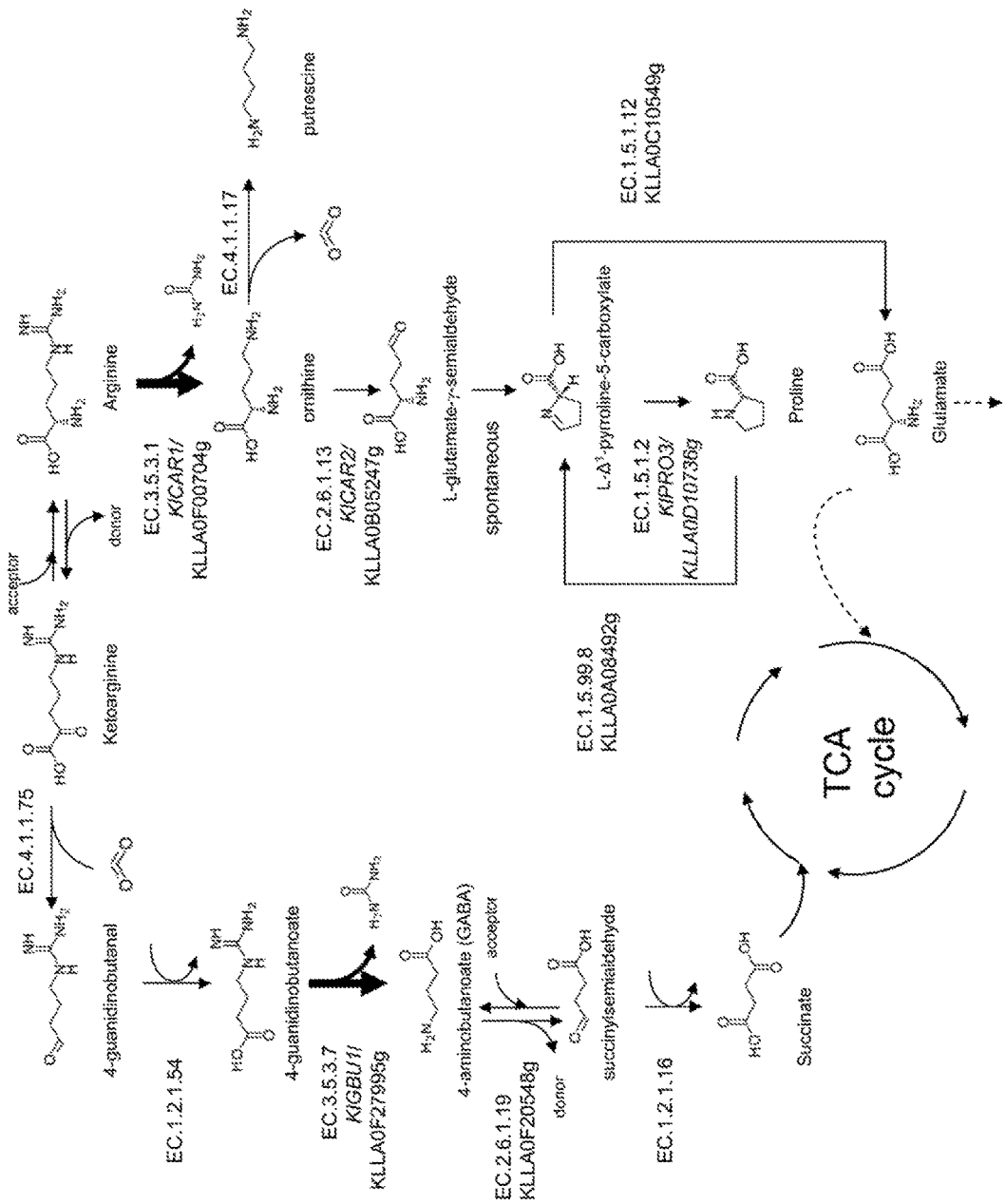

22 Claims, 16 Drawing Sheets
Specification includes a Sequence Listing.

FIG. 2A

```
XP_456325            ----MKVAGFI-LG-ALI---------QFSLTE----------------GHVE-------
XP_002498240         ----MRFSTLASLA-ALF---------EFT-TA----------------GR---------
XP_716668            ----MKLLALL----TLL---------PLVI------------------------------
XP_461566            ----MKVLNIS-TI-LFI---------ATTTTA----------------NQLH-------
EIF45280             ------------------------------MPFPK----------------SQSE-------
BAO40383             MINWSYYALFC-L--AIV---------PFAKCE----------------YYNE-------
AADM01000201.1       ------------------------------------------------------------
XP_503530            -----MDSEYG-DL-SVE---------QKPIKDHSHSHHHHDHGHGHGNGHVE-------
EFW95653             ----MAVAK-A-LQ-SPI---------QFA-------------------------------
XP_002552049         ML--MRSVLFS-L--ACA---------NAVLAS----------------GTTV-------
XP_001523956         ----MKLLLTL-LG--IL---------QVCIA-----------------------------
XP_001482640         ----MKLLPLL-FATALA---------QLTLKN----------------DNVV-------
XP_004196483         MLKSISYWAFI-LS-IYLGVVCADEAEQIASAE----------------GFAK-------
XP_001385334         ----MK-CSHI-VS-API---------FLSVAA----------------AVLQPVAWKSD
XP_003679661         -------MLYL-FS-LCV---------LLSLAW----------------CY-E-------
AACE03000003.1       ------------------------------------------------------------

Consensus                        M

XP_456325            -------Q-N--------------ENA-NLT-EMWGEDWP-------FSGIQTFAHLPH
XP_002498240         -----------------------------WTEDWP-------FAGFPSFAKLPF
XP_716668            --------------------------ST-NLE-EKWGGLWP-------FQGIATFAHLEH
XP_461566            -------S-DPFSDNVVYFDTHSAEREP-NLK-DMWDDLWP-------FQGINTFAHLEH
EIF45280             -------S-R--------------KSP-TLE-QLWGQXWP-------FTGIPTFAHLNT
BAO40383             -------DIG--------------TNS-TLN-DMWGEEWP-------FSGIQTFAHLPH
AADM01000201.1       ------------------------------------------------------------
XP_503530            -------V---------------EYL-NLPGNNFYEDLDAELNGPLYAGIQTFAHLGH
EFW95653             -------S-N--------------SEP-TLD-QLWGEDWP-------FNGIQTFAHLNY
XP_002552049         -------L-E--------------ED---LE-QMWGQDWP-------FSGIQTFAHLPH
XP_001523956         ------------------------T-DLE-EKWGSLWQ-------FQGIATFAHLEH
XP_001482640         -------Y-D--------------SNPPSLS-EMWDGLWP-------FQGINTFAHLDH
XP_004196483         -------M-Q--------------RNA-TLE-EMWGELWP-------FQGINTFAHLEH
XP_001385334         ELINDSID-G--------------SSP-SLK-EMWDDLWP-------FQGINTFAHLDH
XP_003679661         -------D-R--------------ATD-DLD-RLWGQDWP-------FSGINTYAHLPH
AACE03000003.1       ------------------------------------------------------------

Consensus            ------------------------L----WG-WP         F-GI-TFAHL-H
```

FIG. 2A, Cont'd

```
XP_456325         HKCLIDME---KKFDIGVIGVPFDTAVSFRGGARFGPQAIRKASQRQTSMRGFNFRADIN
XP_002498240      HTCLVD-N---PEFDIALIGVPFDTAVSFRPGARFGPQAIRRASQRQNGLRGFNARAGIN
XP_716668         FQCLIESE---KQFDIGIIGVPFDTAVSYRPGARFGPRAIRDASQRQNNLRGFNPKALFD
XP_461566         NKCLLDPD---QEYDIGIIGVPFDTATSYRPGARFGPRAIRSASQRQTSLRGYNQRADFN
EIF45280          TKCLLSPE---SXYDIGIIGVPFDTATSYRPGARFGPQAIRLASQRQNSMRGFNTRAGIN
BAO40383          QKCLLDMG---TKFDIGVIGMPFDTAVSYRPGARFGPQGIRKASQRQNSMRGFNFRAGIN
AADM01000201.1    ------------------MPFDTAVSYRPGARFGPQAIRRSSQRQNSMRGFNSRAGIN
XP_503530         VSCFDPTNFASEQFDIALVGAPFDTAVTFRSGARFGPAGIRKGSRRMSPGQVSPYREGFM
EFW95653          TKCLVDPE---TSFDIGVIGVPFDTATTYRSGARFGPRAIRTGSQRQTSKRAFNTRAGIN
XP_002552049      EKCLMNRS---LDFDIGVIGIPFDTAVTYRPGARFGPQAIRKSSQRQTSMRGFNFRAGIN
XP_001523956      TQCLVNPK---ESFDVAVIGVPFDTAVSYRPGARFGPRAIRDASQRQYSLRGFNHRALFN
XP_001482640      KVCLTQPD---EIYDFAIIGVPFDTAVLYRPGARFGPRAIRAAAQRQTSLRGYNQRANFN
XP_004196483      FKCLVEQD---EKYDIGIIGVPYDTSVSYRPGARFGPRAIRTASQRQTSLRGFNQRAFFN
XP_001385334      HKCLLEPG---NTYDVALIGVPFDTAVSYRPGARFGPRAIRAASQRQTSLRGYNQRANFN
XP_003679661      QKCLLDKN---FTFDIGIIGVPFDSAVTYRPGARFGPQAIRAASQRQIPIRSFNFRAGIN
AACE03000003.1    ---------------------------------------MRGFNFRAGIN

Consensus         -KCL----   --FDIG-IGVPFDTAVS-R-GARFGP-AIR-AS**QRQ-S-RGFN-RA-IN**

XP_456325         PYQDWASVVDCGDVPVTPMDNCLALKMMTAAYENLLSHESQTSDNNLP--PRFVTLGGDH
XP_002498240      PYDNWAHIIDCGDIPVTPMDNQLALEQMNAAYDELV-NGTTTSGNTAGALPRLVSLGGDH
XP_716668         PYQSWARIIDCGDIPVTPMDNSAAYKQMSEAFKDLLNRKS-SNNTEIP--PRYIALGGDH
XP_461566         PYTSWAKVIDCGDMPVTPMDNSLAFKQMNKGFEELIARRNSKNSTVTP--PRYIALGGDH
EIF45280          PYQNWASLVDCGDIPVTPMDNKVALDQMTAAFEELLLRRNSSLGDAHP--PRYVALGGDH
BAO40383          PYNNWASVIDCGDVPVTPMDNNLALQMMTAAYDNLLSHESKAESNELP--PRLVTLGGDH
AADM01000201.1    PYQNWAKIMDCGDVPVTPMDNQLALKMMTSAYETLLNHSSTTKDSKLP--PRLVTLGGDH
XP_503530         LYDDWAKFVDCGDVAMHPLDNRYALNQLYRGMRAIHNHTTSTLNATHI--PRAILMGGDH
EFW95653          PYQDWAKVIDCGDIPVTPMDNELALDQMTKAFEELLLKRKNAVDGSGP--PKLVALGGDH
XP_002552049      PYQDWAKVLDCGDVPVTPMDNNLALQMMGAAYHNLLNRNSTLKQAELP--PRFATLGGDH
XP_001523956      PYKSWAKIIDCGDIPVTPMDNHLAFKQMDIAFDELL-QRSSANDSRVP--PRYVVLGGDH
XP_001482640      PYTSWAKVLDCGDIPVTPMDNHLAFKQMDLAFEELILR--RNSSSKAP--PRYIALGGDH
XP_004196483      PYTSWARIVDCGDVPVTPVDNELAFKQMTAAFEELLLRRSAKNDSSMP--PRHIILGGDH
XP_001385334      PYASWAKIVDCGDLPITPMDNSIAFTQMTKGFEELLLRRSSNSSSELP--PRYVALGGDH
XP_003679661      PYQKWAKVVDCGDIPVTPMDSSLALEMMTAAYENLLDRDSEYSKSSMP--PRLLSLGGDH
AACE03000003.1    PYQSWAKVMDCGDIPVTPMDNQLALKMMDAAYENLLDRNSTAAESPLP--PRFASLGGDH
                   *  **   ****    * *   *                            *    ****
Consensus         PY--WA---DCGD-PVTPMDN-LAL- M--A-E-LL---S-------P  PR---LGGDH
```

FIG. 2A, Cont'd

```
XP_456325        SIILPALRALRKTYGRLAVIHFDSHLDTWAPSKYPSFWHSDTSEFTHGSMLWIAHNEGLL
XP_002498240     SVILPALRALHKHYGPISVIHLDSHLDTWSPDSYPSYWHSNTSEFTHGSMLWLAAQEGLI
XP_716668        SVLLPHIRALHKIYGPVNIIHFDAHLDTWKPNKYPT---SEKNDINHGSMLWKAYEEGLT
XP_461566        SVLLPHLRALHEVYGKINILHFDAHLDTWGPDKYPSFWHSKQAELNHGSMLWKANKE-CL
EIF45280         SIILPHLRALHEVYGKIAVIHFDAHLDTWTPXKYPSFWSSEQSKFTHGSMLWMAKKEGIL
BAO40383         SIILPALRSLHKLYGRLAVIHFDSHLDTWSPSKYPSFWHSDTSEFTHGSMLWIAHNEGLI
AADM01000201.1   SILLPVLRSLKEVYGPIAVIHFDSHLDTWAPAKYPSFWHSDTSEFTHGSMLWLASQEGLL
XP_503530        TTTLSALQAIYEKIGPVSVIHFDSHIDTWDPMVLGGN-VSSYMQVNHGTFLHYAAERGYL
EFW95653         SILLPHLRALNKVYGKVAVIHFDAHLDTWSPSKYPSFWSSDQSKFTHGSMLWMANEEDLL
XP_002552049     SIILPILRQLHKIYGPISVIHFDSHLDTWAPSKYPSYWHSNNSDFTHGSMLWIAKQEGLL
XP_001523956     SVLLPHLRALKKHYGRLNVLHFDAHLDTWSPLKYPSFWRTDQNDLNHGSMLWQAHEEG-L
XP_001482640     SVLLPHLRALKKAYGPLNVIHFDAHLDTWSPDKYPSFWHSDQSEITHGSMLWTAFEEG-L
XP_004196483     SVILPHLRALSKVHGPINVIHLDAHLDTWAPDKYPSFWHSAQSEVNHGSMLWKAHQEGLL
XP_001385334     SVLLPHLRALHEVYGRINVIHFDAHLDTWAPDKYPSFWHSDQSEINHGSMLWKAHHEG-L
XP_003679661     SIILPVIRNLYKLYGPITVLHFDSHLDTWSPSKYPSYWHSKSSKFTHGSMLWMAKQEGLL
AACE03000003.1   SVILPILRQLHKIYGPISVIHFDSHLDTWAPSKYPSYWHSDTSEFTHGSMLWIAKQEGLL
                       *         *    * * *** *                        **  *   *
Consensus        S--LP-LRAL-K-YG---VIHFD HLDTW-P-KYPSFWHS--SEFTHGSMLW-A--EGLL XP_456325        TENNNIHAGLRT---RLSGSSFEDYDDDDKVGFHRIEADEIMD---GGIKS----IVEKIK
XP_002498240     NKGHCVHGGLRT---RLSGDDWSDYEEDDRVGFHRIHADEMME---IGPRG----IAERIK
XP_716668        TK-HNIHVGVRT---RL--SELDDLQDDDEQNFVRIEADDIWL---KGPQW----VVDKIL
XP_461566        TSEHNVHAGVRT---KLSG--IEDYVDDSQNFTRITADDIWI---KGVQY----VVDKIL
EIF45280         SDDYNVHVGIRT---RISGVSWEDFDEDDDQGWLRFSADDVWV---GGKQSLDQIVASIK
BAO40383         TENSNVHAGLRT---RLSGTSYEDYDEDDQVGFYRIEADEIMD---GGPSA----IVEKIK
AADM01000201.1   SGGHNVHAGLRT---RLSGTSWEDYDEDDEVGFYRIQADEIMD---IGVHG----VAKKII
XP_503530        NHGHNLHVGSRAPYVRKHG-----DIEHDKHCGFAIVNAREIDE---VGIAG----VVQKIK
EFW95653         SDDYNVHIGLRT---RISGKDWEDYEDDDDQGWARFSADDIWINGLGGLKE----IVRSIN
XP_002552049     SENSNVHAGLRT---RLSGVGWDDYEEDKETGFHRIECDEILD---IGVRG----IARKIL
XP_001523956     TTNRNVHAGVRT---KLSG--IEDYQDDDAQNWVRIEADDIWL---KGPQY----VVDKIL
XP_001482640     TTNTNIHAGLRT---KLSG--LEDYEDDDKQNFVRIYADDIWI---DGVQS----VIAKIN
XP_004196483     S-HNNVHAGLRT---KLSG--IADYEDDDAQHFTRITADDIWI---KGPDY----VLDTIL
XP_001385334     TSHHNVHAGLRT---KLSG--LEDYEDDDSQHFIRIDADDIWL---KGPQW----VVQKIL
XP_003679661     SE-HNVHAGLRT---RLSGVDWEDYEDDDDVGFHRIESDDIIR---LGVQG----LAEKIK
AACE03000003.1   AENSNVHAGLRT---RLSGVGWDDYEEDSETGFHRIECDEILK---VGVNG----IAERIL
                     *  *  *          *  *                *         *
Consensus        ----N-HAGLRT   RLSG---EDY-DDD--GF-RI-AD-I--    -G---    -V-KI-
```

FIG. 2A, Cont'd

```
XP_456325        SKIPSDVPVYISVDIDVLDPSAAPGTGTMEVGGWMTRELIRIIRELEDLNLVGADIVEVS
XP_002498240     QIVPKNVPVYLSVDIDVLDPSAAPGTGTVEPGGWLTRELISLIRQLQDLPLVGADVVEVS
XP_716668        ATIPKDTATYISVDVDVLDPGFTSGTGTQEPGGFLPRELIYLLRSIDGLTVVGADVVEVS
XP_461566        ETIPPDTPTYLSVDIDVLDPAFGSGTGTQEPGGWLPRELIHVLRSIENLTIVGADIVEVS
EIF45280         KRIPAHYPVYISVDVDCMDPGFTPGTGTIEPGGMMPREVIYLLRHL-DLDLVGADVVEVA
BAO40383         SKIPDNVPVYISVDIDVLDPSAAPGTGTMEAGGWLTRELIRIIRQLDHLNLVGADVVEVS
AADM01000201.1   ERVPKDIPVYISVDIDVLDPSAAPGTGTMEVGGWLTRELISIIRKLEDLTLVGADIVEVS
XP_503530        DRV-GNTNVYISVDIDVLDPVYAPGTGTAEPGGYTTREFMQILDGLEGINIVGADVVEVA
EFW95653         ERIPKDYPTYVSVDIDCLDPGFAPGTGTIESGGLLPRELFYLLRNI-DVNLVGADIVEVS
XP_002552049     DIVPKDKPVYISVDIDVLDPSAAPGTGTVEVGGLLTRELISIIRQLDGLSLIGADVVEVS
XP_001523956     ETIPKDSPTYLSVDIDVLDPGFASGTGTQESGGWLPRELIHILRGVEELTIVGADVVEVA
XP_001482640     ATIPADTPTYISVDIDVLDPGFGSGTGTQEPGGWLPRELIYVLRHIDHLTIVGGDVVEVS
XP_004196483     KVVPANTPTYISVDIDVLDPAFGSGTGTQEPGGWLPRELIYILRGLENLDVVGADIVEVS
XP_001385334     DTVPDDSPTYISVDVDVLDPGFTSGTGTQEPGGWLPRELLHVLRSIEGLTVVGGDVVEVS
XP_003679661     QLLPKKQPLYISVDIDVLDPSAAPGTGTVEAGGWLTRELIYLLRSLEDYPIVGADVVEVS
AACE03000003.1   EHVPKDKPVYISVDIDVLDPSAAPGTGTIEVGGLLTRELISIIRQLEDLHLVGADVVEVS
                     *  ***   *  **      ****  *  **       **          *  * ***
Consensus        ----P-D-P YISVDIDVLDP---APGTGT-E-GGW-RELI-----R-LE-L---VGAD--VEVS XP_456325        PPFD-PTEITSLAGAQIAYELITNMVKKGPIDPELIKHN-----LELSDKLT-QGQQL--
XP_002498240     PPFD-HADVTAMAAAQVAYEIITNMVKT-PLELETRKF----------------------
XP_716668        PAYD-IAEITATNGAQIAYEVLTSMVKRGNIDKSLVKSV-----VHVFD-----------
XP_461566        PAFD-TAEITATNGAQVVFEILTSMVKKGSVG-HLVKNNNPKELLEVKSKNDGKSTQY--
EIF45280         PAYD-QAEITATNAAQVVFELVTTMVKRG-------------------------------
BAO40383         PPFD-PSEITTLAGAQVAYELITNMVKKGPLDPDMVKRN-----LESKNANH-FQMQ---
AADM01000201.1   PAYD-SGDVTSLAAAQIAYELITNMVKKGPVADEIVEKN-----KQIAENLA-ENNHV--
XP_503530        PAYDGPGDVTLLAAAQVIDSLASLMVMNGPL--------S-----TRQSTK---------
EFW95653         PQYD-HAEITATNGAEVAYQLITSIVK-----------------------QGKK---
XP_002552049     PAYD-QSDITSTAASQIVYELITNMVKKGPLDPAMIQAN-----K--NSEMD-QGDKP--
XP_001523956     PAYD-VSEVTATNGAQMAFEILTSMVKKGNVDKNIVDRT-----IEI-------------
XP_001482640     PAFD-NAEITATNGAQVAYELLTSMVKKGRVD--LLVQR-----EEATPIIK-SSEVE--
XP_004196483     PAFD-IAEITATNGAQVVFEILTSIVKKG--------NS-----EKVADSSS-QKDKG--
XP_001385334     PAFD-TAEITSTNGAQIAFEIITSMVKKGPIDPAIVKKN-----KKELVKIT-HVNELEQ
XP_003679661     PPFD-QSEITAIAASQIAYELLTSMVKSGPIEPQMIQEN-----GLFNLRAL-QDNHV--
AACE03000003.1   PAYD-HADITSTAASQIVYELITNMVKKGPVDPAIVEAN---------------------
                 *    *       *                 *
Consensus        P--D----EI--T-GAQ-AYEL-T-MVKKGP---------------------
```

FIG. 2A, Cont'd

```
XP_456325           -------LGFSSPT--------DELNDKIQ-----KE--QFV-----------LQA-----
XP_002498240        -----------FSNM-----------------------------------------------
XP_716668           --------------------------------------------------------------
XP_461566           -------LDKQEIN--------RLIENKLQ-----EF--ENIKFNLLSEIEQLRST----
EIF45280            -----------KPL--------PVRED-----------------------------------
BAO40383            ------------------------Q-----NE--QNV-----------LHI-----
AADM01000201.1      -------RVTEQGT--------TKILERLI-----QDANQAV-----------LHATNPLL
XP_503530           --------------------------------------------------------------
EFW95653            --------------------------------------------------------------
XP_002552049        -------QNLAENE---------YQSLGEGA-----RQ--NFMESL--------LQGRV---
XP_001523956        -----------FES------------------------------------------------
XP_001482640        -------LTLEERL---------TSEIRQLK-----NM--QAL-----------FN------
XP_004196483        -------SSAALQD--------DKIKQQKQDVLTRKN--PFV-----------ISN------
XP_001385334        EKKDFIDLEKAKKTIEQKLKELDELKSELS------SQ--LLE-----------LREIPF--
XP_003679661        ------DFSAAKP--------DTDYDKLL---------------------------------
AACE03000003.1      --------------------------------------------------------------

Consensus           --------------------------------------------------------------
```

```
XP_456325           (SEQ ID NO: 148)
XP_002498240        (SEQ ID NO: 149)
XP_716668           (SEQ ID NO: 150)
XP_461566           (SEQ ID NO: 151)
EIF45280            (SEQ ID NO: 152)
BAO40383            (SEQ ID NO: 153)
AADM01000201.1      (SEQ ID NO: 154)
XP_503530           (SEQ ID NO: 155)
EFW95653            (SEQ ID NO: 156)
XP_002552049        (SEQ ID NO: 157)
XP_001523956        (SEQ ID NO: 158)
XP_001482640        (SEQ ID NO: 159)
XP_004196483        (SEQ ID NO: 160)
XP_001385334        (SEQ ID NO: 161)
XP_003679661        (SEQ ID NO: 162)
AACE03000003.1      (SEQ ID NO: 163)
```

Consensus:  1. (SEQ ID NO: 148 -- Peptide sequences: TFAHL [amino acids ("aa") 44-48]; FDIG [aa 61-64]; IGVPFDTAVS [aa 66-75]; GARFGP [aa 79-84]; ASQRQ [aa 90-94]; RGFN [aa 98-101]; INPY [aa 106-109]; DCGD [aa 117-120]; PVTPMDN [aa 122-128]; LGGDHS [aa 161-166]; LRAL [aa 172-175]; VIHFD [aa 184-188]; HLDTW [aa 190-194]; KYPSFWHS [aa 198-205]; SEFTHGSMLW [aa 208-217]; EGLL [aa 222-225]; HAGLRT [aa 232-237]; RLSG [aa 238-241]; YISVDIDVLDP [aa 286-296]; APGTGT [aa 299-304]; RELI [aa 313-316]; VGAD [aa 328-331]; VEVSP [aa 333-337]; AYEL [aa 353-356]; MVKKGP [aa 360-365])

2. (SEQ ID NO: 164 -- First bold sequence)

3. (SEQ ID NO: 165 -- Second bold sequence)

FIG. 3

```
  1 mkvagfilga liqfsltegh veqnenanlt emwgedwpfs giqtfahlph hkclidmekk
 61 fdigvigvpf dtavsfrgga rfgpqairka sqrqtsmrgf nfradinpyq dwasvvdcgd
121 vpvtpmdncl alkmmtaaye nllshesqts dnnlpprfvt lggdhsiilp alralrktyg
181 rlavihfdsh ldtwapskyp sfwhsdtsef thgsmlwiah neglltennn ihaglrtrls
241 gssfedyddd dkvgfhriea deimdggiks ivekikskip sdvpvyisvd idvldpsaap
301 gtgtmevggw mtreliriir eledlnlvga divevsppfd pteitslaga qiayelitnm
361 vkkgpidpel ikhnlelsdk ltqgqqllgf ssptdelndk iqkeqfvlqa
(SEQ ID NO: 148)
```

FIG. 4A

```
NP_289508      --------------MSTLGHQYDNSLVSNAFGFLRLPMNFQPYDSDADWVITGVPFDMATS
WP_000105576   --------------MSTLGHQYDNSLVSNAFGFLRLPMNFQPYDSDADWVITGVPFDMATS
YP_005016506   --------------MSTLGHQYDNSLVSNAFGFLRLPMNFMPYDSDADWVITGVPFDMATS
YP_001337000   --------------MSTLGHQYDNSLVSNAFGFLRLPMNFMPYESDADWVITGVPFDMATS
YP_003614749   --------------MSTLGHQYDNSLVSNAFGFLRLPMNFQPYDSDADWVITGVPFDMATS
YP_001455807   --------------MSTLGHQYDNSLVSNAFGFLRLPLNFQPYDSDADWVITGVPFDMATS
-P_004532666   --------------MSTLGHQYDNSLVSNAFGFLRLPLNFQPYDSDADWVITGVPFDMATS
WP_006734551   --------------MSTLGHQYDNSLVSNAFGFLRLPMNFQPYDSDADWVITGVPFDMATS
AHE29794       MNETLYGDGAIRRPSIYGSSVENT-YAGVLSFMR--RNYTRDLGGVDVAVCGVPLDLATT
                              *  *   *      **  *       *    *** *  **
Consensus      MSTLGHQYDNSLVSNAFGFLRLPMNFQPYDSDADWVITGVPFDMATS NP_289508      GRAGGRHGPAAIRQVSTNLAWEHNRFPWNFDMRERLNVVDCGDLVYAFGDAREMSEKLQA
WP_000105576   GRAGGRHGPAAIRQVSTNLAWEHNRFPWNFDMRERLNVVDCGDLVYAFGDAREMSEKLQA
YP_005016506   GRAGGRHGPAAIRQVSTNLAWEHNRFPWNFDMRERLNVVDCGDLVYAFGDAREMSEKLQA
YP_001337000   GRAGGRHGPAAIRQVSTNLAWEHNRFPWNFDMRERLNVVDCGDLVYAFGDAREMSEKLQA
YP_003614749   GRAGGRHGPAAIRQVSTNLAWEHNRFPWNFDMRERLNVVDCGDLVYAFGDAREMSEKLQA
YP_001455807   GRAGGRHGPAAIRQVSTNLAWEHNRFPWNFDMRERLNVVDCGDLVYAFGDAREMSEKLQA
-P_004532666   GRAGGRHGPAAIRQVSTNLAWEHYRFPWNFDMRERLNVVDCGDLVYAFGDAREMSEKLQA
WP_006734551   GRAGGRHGPAAIRQVSTNLAWEHHRFPWNFDMRERLNVVDCGDLVYAFGDAREMSEKLQA
AHE29794       FRSGARLGPAAVRAASVQLA-ELRPYPWGFDPFDDLAVIDYGDCWFDAHNPLSIKPAIVE
                * *   **** *  *  *   * * **  ** **  *    **   *  *   *
Consensus      GRAGGRHGPAAIRQVSTNLAWEHNRFPWNFDMRERLNVVDCGDLVYAFGDAREMSEKLQA NP_289508      HAEKLLAAGKRMLSFGGDHFVTLPLLRAHAKHFGK-MALVHFDAHTDTYANGC--EFDHG
WP_000105576   HAEKLLASGKRMLSFGGDHFVTLPLLRAHAKHFGK-MALVHFDAHTDTYANGC--EFDHG
YP_005016506   HAEKLLAAGKRMLSFGGDHFVTLPLLRAHAKHFGK-MALVHFDAHTDTYANGC--EFDHG
YP_001337000   HAEKLLAAGKRMLSFGGDHFVTLPLLRAHAKHFGK-MALVHFDAHTDTYANGC--EFDHG
YP_003614749   HAEKLLAAGKRMLSFGGDHFVTLPLLRAHAKHFGK-MALVHFDAHTDTYANGC--EFDHG
YP_001455807   HAEKLLSAGKRMLSFGGDHFVTLPLLRAHAKHFGK-MALVHFDAHTDTYANGC--EFDHG
-P_004532666   HAERLLAAGKRMLSFGGDHFVTLPLLRAHAKHFGK-MALVHFDAHTDTYANGC--EFDHG
WP_006734551   HAEKLLSAGKRMLSFGGDHFVTLPLLRAHAKHFGK-MALVHFDAHTDTYANGC--EFDHG
AHE29794       HARTILQSGAAMLTLGGDHYITYPLLIAHAQRHGKPLSLIHFDAHCDTWADDAPDSLNHG
               **    *  *  * ****  *  ***  **   **    ***** **        **
Consensus      HAEKLLAAGKRMLSFGGDHFVTLPLLRAHAKHFGK-MALVHFDAHTDTYANGC  EFDHG
```

FIG. 4A, Cont'd

```
NP_289508       TMFYTAPKEGLIDPNHSVQIGIRTEFDKDNGFTVLDACQVNDRSVDDVIAQVKQIVGDMP
WP_000105576    TMFYTAPKEGLIDPNHSVQIGIRTEFDKDNGFTVLDACQVNDRSVDDVIAQVKQIVGDMP
YP_005016506    TMFYTAPNEGLIDPNHSVQIGIRTEFDKDNGFTVLDAGQVNDRSVDDVIAQVKQIVGDMP
YP_001337000    TMFYTAPNEGLIDPNHSVQIGIRTEFDKDNGFTVLDAGQVNDRSVDDVIAQVKQIVGDMP
YP_003614749    TMFYTAPNEGLIDPNHSVQIGIRTEFDKDNGFTVLDACQVNDRGVDDIIAQVKQIVGDMP
YP_001455807    TMFYTAPKEGLIDPNHSVQIGIRTEFDKDNGFTVLDACQVNDRGVDDIIAQVNQIVGDMP
-P_004532666    TMFYTAPKEGLIDPNHSVQIGIRTEFDKDNGFTVLDACQVNDRGVDDIIAQVKQIVGDMP
WP_006734551    TMFYTAPKEGLIDPHHSVQIGIRTEFDKDNGFTVLDACQVNDRGVDDILAQVKQIVGDMP
AHE29794        TMFYKAVNEGLIDPKTSVQVGIRTWNDDYLGIHVLDAAWVHEHGPRATAERIASIVGGRP
                ****  * ****** *** ****  *  * ****  *           ***  *
Consensus       TMFYTAPKEGLIDPNHSVQIGIRTEFDKDNGFTVLDACQVNDRGVDDVIAQVKQIVGDMP NP_289508       VYLTFDIDCLDPAFAPGTGTPVIGGLTSDRAIKLVRGLKDLNIVGMDVVEVAPAYDQSEI
WP_000105576    VYLTFDIDCLDPAFAPGTGTPVIGGLTSDRAIKLVRGLKDLNIVGMDVVEVAPAYDQSEI
YP_005016506    VYLTFDIDCLDPAFAPGTGTPVIGGLTSDRAIKLVRGLKDLNIVGMDVVEVAPAYDQSEI
YP_001337000    VYLTFDIDCLDPAFAPGTGTPVIGGLTSDRAIKLVRGLKDLNIVGMDVVEVAPAYDQSEI
YP_003614749    VYLTFDIDCLDPAFAPGTGTPVIGGLTSDRAIKLVRGLKDLNIVGMDVVEVAPAYDQSEI
YP_001455807    VYLTFDIDCLDPAFAPGTGTPVIGGLTSDRAIKLVRGLKDLNIVGMDVVEVAPAYDQSEI
-P_004532666    VYLTFDIDCLDPAFAPGTGTPVIGGLTSDRAIKLVRGLKDLNIVGMDVVEVAPAYDQSEI
WP_006734551    VYLTFDIDCLDPAFAPGTGTPVIGGLTSDRAIKLVRGLKDLNIVGMDVVEVAPAYDQSEI
AHE29794        AYLTFDIDCLDPAFAPGTGTPVAGGLSSAQALAIVRGLGGVNLIGADVVEVAPAYDQSEI
                 ******************** *** *  *  **** *   * **************
Consensus       VYLTFDIDCLDPAFAPGTGTPVIGGLTSDRAIKLVRGLKDLNIVGMDVVEVAPAYDQSEI NP_289508       TALAAATLALEMLYIQAAKKGE-- (SEQ ID NO: 166)
WP_000105576    TALAAATLALEMLYIQAAKKGE-- (SEQ ID NO: 167)
YP_005016506    TALAAATLALEMLYIQAAKKGE-- (SEQ ID NO: 168)
YP_001337000    TALAAATLALEMLYIQAAKKGE-- (SEQ ID NO: 169)
YP_003614749    TALAAATLALEMLYIQAAKKGE-- (SEQ ID NO: 170)
YP_001455807    TALAAATLALEMLYIQAAKKGE-- (SEQ ID NO: 171)
-P_004532666    TALAAATLALEMLYIQAAKKGE-- (SEQ ID NO: 172)
WP_006734551    TALAAATLALEMLYIQSAKKGE-- (SEQ ID NO: 173)
AHE29794        TAIAAHVACDLLCLWRQRKTGAR  (SEQ ID NO: 174)
                ** ***  *    *    *
Consensus       TALAAATLALEMLYIQAAKKGE   (SEQ ID NO: 177)
```

FIG. 5

```
  1 mstlghqydn slvsnafgfl rlpmnfqpyd sdadwvitgv pfdmatsgra ggrhgpaair
 61 qvstnlaweh nrfpwnfdmr erlnvvdcgd lvyafgdare mseklqahae kllaagkrml
121 sfggdhfvtl pllrahakhf gkmalvhfda htdtyangce fdhgtmfyta pkeglidpnh
181 svqigirtef dkdngftvld acqvndrsvd dviaqvkqiv gdmpvyltfd idcldpafap
241 gtgtpviggl tsdraiklvr glkdlnivgm dvvevapayd qseitalaaa tlalemlyiq
301 aakkge(SEQ ID NO: 166)
```

A
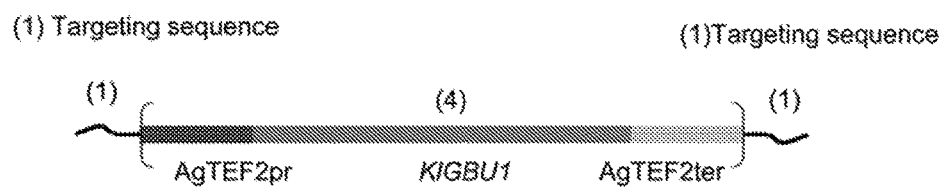
B
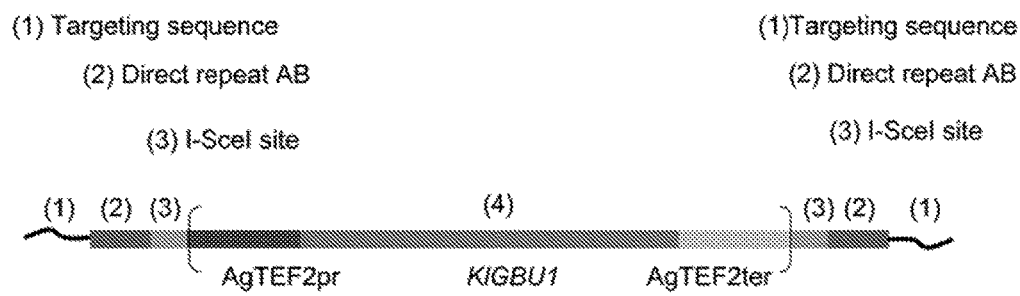
FIG. 10

SEQUENCE LISTING

```
<160> NUMBER OF SEQ ID NOS: 177

<210> SEQ ID NO 1
<211> LENGTH: 30
<212> TYPE: DNA
<213> ORGANISM: Artificial Sequence
<220> FEATURE:
<223> OTHER INFORMATION: homingnuclease PI-PspI

<400> SEQUENCE: 1
tggcaaacag ctattatggg tattatgggt                              30

<210> SEQ ID NO 2
<211> LENGTH: 30
<212> TYPE: DNA
<213> ORGANISM: Artificial Sequence
<220> FEATURE:
<223> OTHER INFORMATION: homing nuclease PI-SceI

<400> SEQUENCE: 2
atctatgtcg ggtgcggaga aagaggtaat                              30

<210> SEQ ID NO 3
<211> LENGTH: 24
<212> TYPE: DNA
<213> ORGANISM: Artificial Sequence
<220> FEATURE:
<223> OTHER INFORMATION: Recognition sequence I-AniI

<400> SEQUENCE: 3
ttgaggaggt ttctctgtaa ataa                                    24

<210> SEQ ID NO 4
<211> LENGTH: 13
<212> TYPE: DNA
<213> ORGANISM: Artificial Sequence
<220> FEATURE:
<223> OTHER INFORMATION: I-AniI Recognition sequence 5' from restriction
      site sense strand
```

```
<400> SEQUENCE: 4
ttgaggaggt ttc                                                          13

<210> SEQ ID NO 5
<211> LENGTH: 11
<212> TYPE: DNA
<213> ORGANISM: Artificial Sequence
<220> FEATURE:
<223> OTHER INFORMATION: I-AniI Recognition sequence 3' from restriction
      site sense strand

<400> SEQUENCE: 5
tctgtaaata a                                                            11

<210> SEQ ID NO 6
<211> LENGTH: 9
<212> TYPE: DNA
<213> ORGANISM: Artificial Sequence
<220> FEATURE:
<223> OTHER INFORMATION: I-AniI Recognition sequence 3' from restriction
      site antisense strand

<400> SEQUENCE: 6 ttgaggagg                                                                9

<210> SEQ ID NO 7
<211> LENGTH: 15
<212> TYPE: DNA
<213> ORGANISM: Artificial Sequence
<220> FEATURE:
<223> OTHER INFORMATION: I-AniI Recognition sequence 5' from restriction
      site antisense strand

<400> SEQUENCE: 7
tttctctgta aataa                                                        15

<210> SEQ ID NO 8
<211> LENGTH: 26
<212> TYPE: DNA
<213> ORGANISM: Artificial Sequence
<220> FEATURE:
<223> OTHER INFORMATION: I-CeuI Recognition sequence

<400> SEQUENCE: 8
taactataac ggtcctaagg tagcga                                            26

<210> SEQ ID NO 9
<211> LENGTH: 18
<212> TYPE: DNA
<213> ORGANISM: Artificial Sequence
<220> FEATURE:
<223> OTHER INFORMATION: I-CeuI Recognition sequence 5' from restriction
      site sense strand

<400> SEQUENCE: 9
taactataac ggtcctaa                                                     18

<210> SEQ ID NO 10
<211> LENGTH: 14
<212> TYPE: DNA
<213> ORGANISM: Artificial Sequence
<220> FEATURE:
<223> OTHER INFORMATION: I-CeuI Recognition sequence 3' from restriction
      site antisense strand
```

```
<400> SEQUENCE: 10
taactataac ggtc                                                           14

<210> SEQ ID NO 11
<211> LENGTH: 12
<212> TYPE: DNA
<213> ORGANISM: Artificial Sequence
<220> FEATURE:
<223> OTHER INFORMATION: I-CeuI Recognition sequence 5' from restriction
      site antisense strand

<400> SEQUENCE: 11
ctaaggtagc ga                                                             12

<210> SEQ ID NO 12
<211> LENGTH: 30
<212> TYPE: DNA
<213> ORGANISM: Artificial Sequence
<220> FEATURE:
<223> OTHER INFORMATION: I-ChuI Recognition sequence

<400> SEQUENCE: 12
gaaggtttgg cacctcgatg tcggctcatc                                          30

<210> SEQ ID NO 13
<211> LENGTH: 17
<212> TYPE: DNA
<213> ORGANISM: Artificial Sequence
<220> FEATURE:
<223> OTHER INFORMATION: I-ChuI Recognition sequence 5' from restriction
      site sense strand

<400> SEQUENCE: 13
gaaggtttgg cacctcg                                                        17

<210> SEQ ID NO 14
<211> LENGTH: 13
<212> TYPE: DNA
<213> ORGANISM: Artificial Sequence
<220> FEATURE:
<223> OTHER INFORMATION: I-ChuI Recognition sequence 3' from restriction
      site sense strand

<400> SEQUENCE: 14
atgtcggctc atc                                                            13

<210> SEQ ID NO 15
<211> LENGTH: 13
<212> TYPE: DNA
<213> ORGANISM: Artificial Sequence
<220> FEATURE:
<223> OTHER INFORMATION: I-ChuI Recognition sequence 3' from restriction
      site antisense strand

<400> SEQUENCE: 15
gaaggtttgg cac                                                            13

<210> SEQ ID NO 16
<211> LENGTH: 17
<212> TYPE: DNA
<213> ORGANISM: Artificial Sequence
<220> FEATURE:
<223> OTHER INFORMATION: I-ChuI Recognition sequence 5' from restriction
      site antisense strand
```

```
<400> SEQUENCE: 16
ctcgatgtcg gctcatc                                                  17

<210> SEQ ID NO 17
<211> LENGTH: 23
<212> TYPE: DNA
<213> ORGANISM: Artificial Sequence
<220> FEATURE:
<223> OTHER INFORMATION: I-CpaI Recognition sequence

<400> SEQUENCE: 17
cgatcctaag gtagcgaaat tca                                           23

<210> SEQ ID NO 18
<211> LENGTH: 18
<212> TYPE: DNA
<213> ORGANISM: Artificial Sequence
<220> FEATURE:
<223> OTHER INFORMATION: I-CpaI Recognition sequence 5' from restriction
      site sense strand

<400> SEQUENCE: 18
cgatcctaag gtagcgaa                                                 18

<210> SEQ ID NO 19
<211> LENGTH: 14
<212> TYPE: DNA
<213> ORGANISM: Artificial Sequence
<220> FEATURE:
<223> OTHER INFORMATION: I-CpaI Recognition sequence 3' from restriction
      site antisense strand

<400> SEQUENCE: 19
cgatcctaag gtag                                                     14

<210> SEQ ID NO 20
<211> LENGTH: 20
<212> TYPE: DNA
<213> ORGANISM: Artificial Sequence
<220> FEATURE:
<223> OTHER INFORMATION: I-CpaII Recognition sequence

<400> SEQUENCE: 20
cccggctaac tctgtgccag                                               20

<210> SEQ ID NO 21
<211> LENGTH: 12
<212> TYPE: DNA
<213> ORGANISM: Artificial Sequence
<220> FEATURE:
<223> OTHER INFORMATION: I-CpaII Recognition sequence 5' from
      restriction site sense strand

<400> SEQUENCE: 21
cccggctaac tc                                                       12

<210> SEQ ID NO 22
<211> LENGTH: 12
<212> TYPE: DNA
<213> ORGANISM: Artificial Sequence
<220> FEATURE:
<223> OTHER INFORMATION: I-CpaII Recognition sequence 5' from
      restriction site antisense strand

<400> SEQUENCE: 22
actctgtgcc ag                                                       12
```

<210> SEQ ID NO 23
<211> LENGTH: 30
<212> TYPE: DNA
<213> ORGANISM: Artificial Sequence
<220> FEATURE:
<223> OTHER INFORMATION: I-CreI Recognition sequence

<400> SEQUENCE: 23
ctgggttcaa aacgtcgtga gacagtttgg                                    30

<210> SEQ ID NO 24
<211> LENGTH: 20
<212> TYPE: DNA
<213> ORGANISM: Artificial Sequence
<220> FEATURE:
<223> OTHER INFORMATION: I-CreI Recognition sequence 5' from restriction
      site sense strand

<400> SEQUENCE: 24
ctgggttcaa aacgtcgtga                                               20

<210> SEQ ID NO 25
<211> LENGTH: 10
<212> TYPE: DNA
<213> ORGANISM: Artificial Sequence
<220> FEATURE:
<223> OTHER INFORMATION: I-CreI Recognition sequence 3' from restriction
      site sense strand

<400> SEQUENCE: 25
gacagtttgg                                                          10

<210> SEQ ID NO 26
<211> LENGTH: 16
<212> TYPE: DNA
<213> ORGANISM: Artificial Sequence
<220> FEATURE:
<223> OTHER INFORMATION: I-CreI Recognition sequence 3' from restriction
      site antisense strand

<400> SEQUENCE: 26
ctgggttcaa aacgtc                                                   16

<210> SEQ ID NO 27
<211> LENGTH: 14
<212> TYPE: DNA
<213> ORGANISM: Artificial Sequence
<220> FEATURE:
<223> OTHER INFORMATION: I-CreI Recognition sequence 5' from restriction
      site antisense strand

<400> SEQUENCE: 27
gtgagacagt ttgg                                                     14

<210> SEQ ID NO 28
<211> LENGTH: 30
<212> TYPE: DNA
<213> ORGANISM: Artificial Sequence
<220> FEATURE:
<223> OTHER INFORMATION: DmoI Recognition sequence

<400> SEQUENCE: 28
atgccttgcc gggtaagttc cggcgcgcat                                    30

<210> SEQ ID NO 29

```
<211> LENGTH: 16
<212> TYPE: DNA
<213> ORGANISM: Artificial Sequence
<220> FEATURE:
<223> OTHER INFORMATION: DmoI Recognition sequence 5' from restriction
      site sense strand

<400> SEQUENCE: 29
atgccttgcc gggtaa                                                       16

<210> SEQ ID NO 30
<211> LENGTH: 14
<212> TYPE: DNA
<213> ORGANISM: Artificial Sequence
<220> FEATURE:
<223> OTHER INFORMATION: DmoI Recognition sequence 3' from restriction
      site sense strand

<400> SEQUENCE: 30
gttccggcgc gcat                                                         14

<210> SEQ ID NO 31
<211> LENGTH: 12
<212> TYPE: DNA
<213> ORGANISM: Artificial Sequence
<220> FEATURE:
<223> OTHER INFORMATION: DmoI Recognition sequence 3' from restriction
      site antisense strand

<400> SEQUENCE: 31
atgccttgcc gg                                                           12

<210> SEQ ID NO 32
<211> LENGTH: 18
<212> TYPE: DNA
<213> ORGANISM: Artificial Sequence
<220> FEATURE:
<223> OTHER INFORMATION: DmoI Recognition sequence 5' from restriction
      site antisense strand

<400> SEQUENCE: 32
gtaagttccg gcgcgcat                                                     18

<210> SEQ ID NO 33
<211> LENGTH: 24
<212> TYPE: DNA
<213> ORGANISM: Artificial Sequence
<220> FEATURE:
<223> OTHER INFORMATION: H-DreI Recognition sequence

<400> SEQUENCE: 33
caaaacgtcg taagttccgg cgcg                                              24

<210> SEQ ID NO 34
<211> LENGTH: 13
<212> TYPE: DNA
<213> ORGANISM: Artificial Sequence
<220> FEATURE:
<223> OTHER INFORMATION: H-DreI Recognition sequence 5' from restriction
      site sense strand

<400> SEQUENCE: 34
caaaacgtcg taa                                                          13

<210> SEQ ID NO 35
<211> LENGTH: 11
<212> TYPE: DNA
```

```
<213> ORGANISM: Artificial Sequence
<220> FEATURE:
<223> OTHER INFORMATION: H-DreI Recognition sequence 3' from restriction
      site sense strand

<400> SEQUENCE: 35
gttccggcgc g                                                          11

<210> SEQ ID NO 36
<211> LENGTH: 15
<212> TYPE: DNA
<213> ORGANISM: Artificial Sequence
<220> FEATURE:
<223> OTHER INFORMATION: H-DreI Recognition sequence 5' from restriction
      site antisense strand

<400> SEQUENCE: 36
gtaagttccg gcgcg                                                      15

<210> SEQ ID NO 37
<211> LENGTH: 24
<212> TYPE: DNA
<213> ORGANISM: Artificial Sequence
<220> FEATURE:
<223> OTHER INFORMATION: I-HmuI Recognition sequence

<400> SEQUENCE: 37
agtaatgagc ctaacgctca gcaa                                            24

<210> SEQ ID NO 38
<211> LENGTH: 16
<212> TYPE: DNA
<213> ORGANISM: Artificial Sequence
<220> FEATURE:
<223> OTHER INFORMATION: I-HmuI Recognition sequence 3' from restriction
      site antisense strand

<400> SEQUENCE: 38
agtaatgagc ctaacg                                                     16

<210> SEQ ID NO 39
<211> LENGTH: 24
<212> TYPE: DNA
<213> ORGANISM: Artificial Sequence
<220> FEATURE:
<223> OTHER INFORMATION: I-HmuII Recognition sequence

<400> SEQUENCE: 39
agtaatgagc ctaacgctca acaa                                            24

<210> SEQ ID NO 40
<211> LENGTH: 59
<212> TYPE: DNA
<213> ORGANISM: Artificial Sequence
<220> FEATURE:
<223> OTHER INFORMATION: I-HmuII Recognition sequence 5' from
      restriction site sense strand
<220> FEATURE:
<221> NAME/KEY: misc_feature
<222> LOCATION: (25)..(59)
<223> OTHER INFORMATION: n is a, c, g, or t

<400> SEQUENCE: 40
tcattactcg gattgcgagt tgttnnnnnn nnnnnnnnnn nnnnnnnnnn nnnnnnnn       59

<210> SEQ ID NO 41
<211> LENGTH: 24
```

```
<212> TYPE: DNA
<213> ORGANISM: Artificial Sequence
<220> FEATURE:
<223> OTHER INFORMATION: I-LlaI Recognition sequence

<400> SEQUENCE: 41
cacatccata accatatcat tttt                                         24

<210> SEQ ID NO 42
<211> LENGTH: 11
<212> TYPE: DNA
<213> ORGANISM: Artificial Sequence
<220> FEATURE:
<223> OTHER INFORMATION: I-LlaI Recognition sequence 5' from restriction
      site sense strand

<400> SEQUENCE: 42
cacatccata a                                                       11

<210> SEQ ID NO 43
<211> LENGTH: 13
<212> TYPE: DNA
<213> ORGANISM: Artificial Sequence
<220> FEATURE:
<223> OTHER INFORMATION: I-LlaI Recognition sequence 3' from restriction
      site sense strand

<400> SEQUENCE: 43
ccatatcatt ttt                                                     13

<210> SEQ ID NO 44
<211> LENGTH: 21
<212> TYPE: DNA
<213> ORGANISM: Artificial Sequence
<220> FEATURE:
<223> OTHER INFORMATION: I-LlaI Recognition sequence 3' from restriction
      site antisense strand

<400> SEQUENCE: 44
cacatccata accatatcat t                                            21

<210> SEQ ID NO 45
<211> LENGTH: 30
<212> TYPE: DNA
<213> ORGANISM: Artificial Sequence
<220> FEATURE:
<223> OTHER INFORMATION: I-MsoI Recognition sequence

<400> SEQUENCE: 45
ctgggttcaa aacgtcgtga gacagtttgg                                   30

<210> SEQ ID NO 46
<211> LENGTH: 20
<212> TYPE: DNA
<213> ORGANISM: Artificial Sequence
<220> FEATURE:
<223> OTHER INFORMATION: I-MsoI Recognition sequence 5' from restriction
      site sense strand

<400> SEQUENCE: 46
ctgggttcaa aacgtcgtga                                              20

<210> SEQ ID NO 47
<211> LENGTH: 10
<212> TYPE: DNA
<213> ORGANISM: Artificial Sequence
<220> FEATURE:
```

```
<223> OTHER INFORMATION: I-MsoI Recognition sequence 3' from restriction
      site sense strand

<400> SEQUENCE: 47
gacagtttgg                                                               10

<210> SEQ ID NO 48
<211> LENGTH: 16
<212> TYPE: DNA
<213> ORGANISM: Artificial Sequence
<220> FEATURE:
<223> OTHER INFORMATION: I-MsoI Recognition sequence 3' from restriction
      site antisense strand

<400> SEQUENCE: 48
ctgggttcaa aacgtc                                                        16

<210> SEQ ID NO 49
<211> LENGTH: 14
<212> TYPE: DNA
<213> ORGANISM: Artificial Sequence
<220> FEATURE:
<223> OTHER INFORMATION: I-MsoI Recognition sequence 5' from restriction
      site antisense strand

<400> SEQUENCE: 49
gtgagacagt ttgg                                                          14

<210> SEQ ID NO 50
<211> LENGTH: 30
<212> TYPE: DNA
<213> ORGANISM: Artificial Sequence
<220> FEATURE:
<223> OTHER INFORMATION: PI-PfuI Recognition sequence

<400> SEQUENCE: 50
gaagatggga ggagggaccg gactcaactt                                         30

<210> SEQ ID NO 51
<211> LENGTH: 16
<212> TYPE: DNA
<213> ORGANISM: Artificial Sequence
<220> FEATURE:
<223> OTHER INFORMATION: PI-PfuI Recognition sequence 5' from
      restriction site sense strand

<400> SEQUENCE: 51
gaagatggga ggaggg                                                        16

<210> SEQ ID NO 52
<211> LENGTH: 14
<212> TYPE: DNA
<213> ORGANISM: Artificial Sequence
<220> FEATURE:
<223> OTHER INFORMATION: PI-PfuI Recognition sequence 3' from
      restriction site sense strand

<400> SEQUENCE: 52
accggactca actt                                                          14

<210> SEQ ID NO 53
<211> LENGTH: 12
<212> TYPE: DNA
<213> ORGANISM: Artificial Sequence
<220> FEATURE:
<223> OTHER INFORMATION: PI-PfuI Recognition sequence 3' from
      restriction site antisense strand
```

-continued

<400> SEQUENCE: 53
gaagatggga gg                                                    12

<210> SEQ ID NO 54
<211> LENGTH: 18
<212> TYPE: DNA
<213> ORGANISM: Artificial Sequence
<220> FEATURE:
<223> OTHER INFORMATION: PI-PfuI Recognition sequence 5' from
      restriction site antisense strand

<400> SEQUENCE: 54
agggaccgga ctcaactt                                              18

<210> SEQ ID NO 55
<211> LENGTH: 15
<212> TYPE: DNA
<213> ORGANISM: Artificial Sequence
<220> FEATURE:
<223> OTHER INFORMATION: PI-PkoII Recognition sequence

<400> SEQUENCE: 55
cagtactacg gttac                                                 15

<210> SEQ ID NO 56
<211> LENGTH: 10
<212> TYPE: DNA
<213> ORGANISM: Artificial Sequence
<220> FEATURE:
<223> OTHER INFORMATION: PI-PkoII Recognition sequence 5' from
      restriction site sense strand

<400> SEQUENCE: 56
cagtactacg                                                       10

<210> SEQ ID NO 57
<211> LENGTH: 25
<212> TYPE: DNA
<213> ORGANISM: Artificial Sequence
<220> FEATURE:
<223> OTHER INFORMATION: I-PorI Recognition sequence

<400> SEQUENCE: 57
gcgagcccgt aagggtgtgt acggg                                      25

<210> SEQ ID NO 58
<211> LENGTH: 16
<212> TYPE: DNA
<213> ORGANISM: Artificial Sequence
<220> FEATURE:
<223> OTHER INFORMATION: I-PorI Recognition sequence 5' from restriction
      site sense strand

<400> SEQUENCE: 58
gcgagcccgt aagggt                                                16

<210> SEQ ID NO 59
<211> LENGTH: 12
<212> TYPE: DNA
<213> ORGANISM: Artificial Sequence
<220> FEATURE:
<223> OTHER INFORMATION: I-PorI Recognition sequence 3' from restriction
      site antisense strand

<400> SEQUENCE: 59
gcgagcccgt aa                                           12

<210> SEQ ID NO 60
<211> LENGTH: 13
<212> TYPE: DNA
<213> ORGANISM: Artificial Sequence
<220> FEATURE:
<223> OTHER INFORMATION: I-PorI Recognition sequence 5' from restriction
      site antisense strand

<400> SEQUENCE: 60
gggtgtgtac ggg                                          13

<210> SEQ ID NO 61
<211> LENGTH: 29
<212> TYPE: DNA
<213> ORGANISM: Artificial Sequence
<220> FEATURE:
<223> OTHER INFORMATION: I-PpoI Recognition sequence

<400> SEQUENCE: 61
taactatgac tctcttaagg tagccaaat                         29

<210> SEQ ID NO 62
<211> LENGTH: 18
<212> TYPE: DNA
<213> ORGANISM: Artificial Sequence
<220> FEATURE:
<223> OTHER INFORMATION: I-PpoI Recognition sequence 5' from restriction
      site sense strand

<400> SEQUENCE: 62
taactatgac tctcttaa                                     18

<210> SEQ ID NO 63
<211> LENGTH: 11
<212> TYPE: DNA
<213> ORGANISM: Artificial Sequence
<220> FEATURE:
<223> OTHER INFORMATION: I-PpoI Recognition sequence 3' from restriction
      site sense strand

<400> SEQUENCE: 63
ggtagccaaa t                                            11

<210> SEQ ID NO 64
<211> LENGTH: 14
<212> TYPE: DNA
<213> ORGANISM: Artificial Sequence
<220> FEATURE:
<223> OTHER INFORMATION: I-PpoI Recognition sequence 3' from restriction
      site antisense strand

<400> SEQUENCE: 64
taactatgac tctc                                         14

<210> SEQ ID NO 65
<211> LENGTH: 15
<212> TYPE: DNA
<213> ORGANISM: Artificial Sequence
<220> FEATURE:
<223> OTHER INFORMATION: I-PpoI Recognition sequence 5' from restriction
      site antisense strand

<400> SEQUENCE: 65
ttaaggtagc caaat                                        15

<210> SEQ ID NO 66
<211> LENGTH: 30
<212> TYPE: DNA
<213> ORGANISM: Artificial Sequence
<220> FEATURE:
<223> OTHER INFORMATION: PI-PspI Recognition sequence

<400> SEQUENCE: 66
tggcaaacag ctattatggg tattatgggt                                30

<210> SEQ ID NO 67
<211> LENGTH: 17
<212> TYPE: DNA
<213> ORGANISM: Artificial Sequence
<220> FEATURE:
<223> OTHER INFORMATION: PI PspI Recognition sequence 5' from
      restriction site sense strand

<400> SEQUENCE: 67
tggcaaacag ctattat                                              17

<210> SEQ ID NO 68
<211> LENGTH: 13
<212> TYPE: DNA
<213> ORGANISM: Artificial Sequence
<220> FEATURE:
<223> OTHER INFORMATION: PI-PspI Recognition sequence 3' from
      restriction site sense strand

<400> SEQUENCE: 68
gggtattatg ggt                                                  13

<210> SEQ ID NO 69
<211> LENGTH: 13
<212> TYPE: DNA
<213> ORGANISM: Artificial Sequence
<220> FEATURE:
<223> OTHER INFORMATION: PI-PspI Recognition sequence 3' from
      restriction site antisense strand

<400> SEQUENCE: 69
tggcaaacag cta                                                  13

<210> SEQ ID NO 70
<211> LENGTH: 17
<212> TYPE: DNA
<213> ORGANISM: Artificial Sequence
<220> FEATURE:
<223> OTHER INFORMATION: PI-PspI Recognition sequence 5' from
      restriction site antisense strand

<400> SEQUENCE: 70
ttatgggtat tatgggt                                              17

<210> SEQ ID NO 71
<211> LENGTH: 28
<212> TYPE: DNA
<213> ORGANISM: Artificial Sequence
<220> FEATURE:
<223> OTHER INFORMATION: I-ScaI Recognition sequence

<400> SEQUENCE: 71
tgtcacattg aggtgcacta gttattac                                  28

<210> SEQ ID NO 72
<211> LENGTH: 19

```
<212> TYPE: DNA
<213> ORGANISM: Artificial Sequence
<220> FEATURE:
<223> OTHER INFORMATION: I-ScaI Recognition sequence 5' from restriction
      site sense strand

<400> SEQUENCE: 72
tgtcacattg aggtgcact                                                    19

<210> SEQ ID NO 73
<211> LENGTH: 15
<212> TYPE: DNA
<213> ORGANISM: Artificial Sequence
<220> FEATURE:
<223> OTHER INFORMATION: I-ScaI Recognition sequence 3' from restriction
      site antisense strand

<400> SEQUENCE: 73
tgtcacattg aggtg                                                        15

<210> SEQ ID NO 74
<211> LENGTH: 13
<212> TYPE: DNA
<213> ORGANISM: Artificial Sequence
<220> FEATURE:
<223> OTHER INFORMATION: I-ScaI Recognition sequence 5' from restriction
      site antisense strand

<400> SEQUENCE: 74
cactagttat tac                                                          13

<210> SEQ ID NO 75
<211> LENGTH: 30
<212> TYPE: DNA
<213> ORGANISM: Artificial Sequence
<220> FEATURE:
<223> OTHER INFORMATION: I-SceI Recognition sequence

<400> SEQUENCE: 75
agttacgcta gggataacag ggtaatatag                                        30

<210> SEQ ID NO 76
<211> LENGTH: 17
<212> TYPE: DNA
<213> ORGANISM: Artificial Sequence
<220> FEATURE:
<223> OTHER INFORMATION: I-SceI Recognition sequence 5' from restriction
      site sense strand

<400> SEQUENCE: 76
agttacgcta gggataa                                                      17

<210> SEQ ID NO 77
<211> LENGTH: 13
<212> TYPE: DNA
<213> ORGANISM: Artificial Sequence
<220> FEATURE:
<223> OTHER INFORMATION: I-SceI Recognition sequence 3' from restriction
      site sense strand

<400> SEQUENCE: 77
cagggtaata tag                                                          13

<210> SEQ ID NO 78
<211> LENGTH: 13
<212> TYPE: DNA
<213> ORGANISM: Artificial Sequence
```

```
<220> FEATURE:
<223> OTHER INFORMATION: I-SceI Recognition sequence 3' from restriction
      site antisense strand

<400> SEQUENCE: 78
agttacgcta ggg                                                          13

<210> SEQ ID NO 79
<211> LENGTH: 17
<212> TYPE: DNA
<213> ORGANISM: Artificial Sequence
<220> FEATURE:
<223> OTHER INFORMATION: I-SceI Recognition sequence 5' from restriction
      site antisense strand

<400> SEQUENCE: 79
ataacagggt aatatag                                                      17

<210> SEQ ID NO 80
<211> LENGTH: 39
<212> TYPE: DNA
<213> ORGANISM: Artificial Sequence
<220> FEATURE:
<223> OTHER INFORMATION: PI-SceI Recognition sequence

<400> SEQUENCE: 80
atctatgtcg ggtgcggaga aagaggtaat gaaatggca                              39

<210> SEQ ID NO 81
<211> LENGTH: 15
<212> TYPE: DNA
<213> ORGANISM: Artificial Sequence
<220> FEATURE:
<223> OTHER INFORMATION: PI-SceI Recognition sequence 5' from
      restriction site sense strand

<400> SEQUENCE: 81
atctatgtcg ggtgc                                                        15

<210> SEQ ID NO 82
<211> LENGTH: 24
<212> TYPE: DNA
<213> ORGANISM: Artificial Sequence
<220> FEATURE:
<223> OTHER INFORMATION: PI-SceI Recognition sequence 3' from
      restriction site sense strand

<400> SEQUENCE: 82
ggagaaagag gtaatgaaat ggca                                              24

<210> SEQ ID NO 83
<211> LENGTH: 11
<212> TYPE: DNA
<213> ORGANISM: Artificial Sequence
<220> FEATURE:
<223> OTHER INFORMATION: PI-SceI Recognition sequence 3' from
      restriction site antisense strand

<400> SEQUENCE: 83
atctatgtcg g                                                            11

<210> SEQ ID NO 84
<211> LENGTH: 28
<212> TYPE: DNA
<213> ORGANISM: Artificial Sequence
<220> FEATURE:
<223> OTHER INFORMATION: PI-SceI Recognition sequence 5' from
```

-continued restriction site antisense strand

<400> SEQUENCE: 84
gtgcggagaa agaggtaatg aaatggca                                28

<210> SEQ ID NO 85
<211> LENGTH: 29
<212> TYPE: DNA
<213> ORGANISM: Artificial Sequence
<220> FEATURE:
<223> OTHER INFORMATION: I-SceII Recognition sequence

<400> SEQUENCE: 85
ttttgattct ttggtcaccc tgaagtata                               29

<210> SEQ ID NO 86
<211> LENGTH: 20
<212> TYPE: DNA
<213> ORGANISM: Artificial Sequence
<220> FEATURE:
<223> OTHER INFORMATION: I-sceII Recognition sequence 5' from
      restriction site sense strand

<400> SEQUENCE: 86
ttttgattct ttggtcaccc                                         20

<210> SEQ ID NO 87
<211> LENGTH: 16
<212> TYPE: DNA
<213> ORGANISM: Artificial Sequence
<220> FEATURE:
<223> OTHER INFORMATION: I-SceII Recognition sequence 3' from
      restriction site antisense strand

<400> SEQUENCE: 87
ttttgattct ttggtc                                             16

<210> SEQ ID NO 88
<211> LENGTH: 13
<212> TYPE: DNA
<213> ORGANISM: Artificial Sequence
<220> FEATURE:
<223> OTHER INFORMATION: I-SceII Recognition sequence 5' from
      restriction site antisense strand

<400> SEQUENCE: 88
accctgaagt ata                                                13

<210> SEQ ID NO 89
<211> LENGTH: 29
<212> TYPE: DNA
<213> ORGANISM: Artificial Sequence
<220> FEATURE:
<223> OTHER INFORMATION: I-SceIII Recognition sequence

<400> SEQUENCE: 89
attggaggtt ttggtaacta tttattacc                               29

<210> SEQ ID NO 90
<211> LENGTH: 18
<212> TYPE: DNA
<213> ORGANISM: Artificial Sequence
<220> FEATURE:
<223> OTHER INFORMATION: I-SceIII Recognition sequence 5' from
      restriction site sense strand

<400> SEQUENCE: 90

```
attggaggtt ttggtaac                                              18
```

<210> SEQ ID NO 91
<211> LENGTH: 11
<212> TYPE: DNA
<213> ORGANISM: Artificial Sequence
<220> FEATURE:
<223> OTHER INFORMATION: I-SceIII Recognition sequence 3' from
      restriction site sense strand

<400> SEQUENCE: 91

```
tatttattac c                                                     11
```

<210> SEQ ID NO 92
<211> LENGTH: 14
<212> TYPE: DNA
<213> ORGANISM: Artificial Sequence
<220> FEATURE:
<223> OTHER INFORMATION: I-SceIII Recognition sequence 3' from
      restriction site antisense strand

<400> SEQUENCE: 92

```
attggaggtt ttgg                                                  14
```

<210> SEQ ID NO 93
<211> LENGTH: 15
<212> TYPE: DNA
<213> ORGANISM: Artificial Sequence
<220> FEATURE:
<223> OTHER INFORMATION: I-SceIII Recognition sequence 5' from
      restriction site antisense strand

<400> SEQUENCE: 93

```
taactattta ttacc                                                 15
```

<210> SEQ ID NO 94
<211> LENGTH: 29
<212> TYPE: DNA
<213> ORGANISM: Artificial Sequence
<220> FEATURE:
<223> OTHER INFORMATION: I-SceIV Recognition sequence

<400> SEQUENCE: 94

```
tcttttctct tgattagccc taatctacg                                  29
```

<210> SEQ ID NO 95
<211> LENGTH: 16
<212> TYPE: DNA
<213> ORGANISM: Artificial Sequence
<220> FEATURE:
<223> OTHER INFORMATION: I-SceIV Recognition sequence 5' from
      restriction site sense strand

<400> SEQUENCE: 95

```
tcttttctct tgatta                                                16
```

<210> SEQ ID NO 96
<211> LENGTH: 13
<212> TYPE: DNA
<213> ORGANISM: Artificial Sequence
<220> FEATURE:
<223> OTHER INFORMATION: I-SceIV Recognition sequence 3' from
      restriction site sense strand

<400> SEQUENCE: 96

```
gccctaatct acg                                                   13
```

<210> SEQ ID NO 97
<211> LENGTH: 12
<212> TYPE: DNA
<213> ORGANISM: Artificial Sequence
<220> FEATURE:
<223> OTHER INFORMATION: I-SceIV Recognition sequence 3' from
      restriction site antisense strand

<400> SEQUENCE: 97
tcttttctct tg                                                        12

<210> SEQ ID NO 98
<211> LENGTH: 17
<212> TYPE: DNA
<213> ORGANISM: Artificial Sequence
<220> FEATURE:
<223> OTHER INFORMATION: I-SceIV Recognition sequence 5' from
      restriction site antisense strand

<400> SEQUENCE: 98
attagcccta atctacg                                                   17

<210> SEQ ID NO 99
<211> LENGTH: 24
<212> TYPE: DNA
<213> ORGANISM: Artificial Sequence
<220> FEATURE:
<223> OTHER INFORMATION: I-SceV Recognition sequence

<400> SEQUENCE: 99
aataattttc ttcttagtaa tgcc                                           24

<210> SEQ ID NO 100
<211> LENGTH: 11
<212> TYPE: DNA
<213> ORGANISM: Artificial Sequence
<220> FEATURE:
<223> OTHER INFORMATION: I-SceV Recognition sequence 5' from restriction
      site sense strand

<400> SEQUENCE: 100
aataattttc t                                                         11

<210> SEQ ID NO 101
<211> LENGTH: 13
<212> TYPE: DNA
<213> ORGANISM: Artificial Sequence
<220> FEATURE:
<223> OTHER INFORMATION: I-SceV Recognition sequence 3' from restriction
      site sense strand

<400> SEQUENCE: 101
tcttagtaat gcc                                                       13

<210> SEQ ID NO 102
<211> LENGTH: 21
<212> TYPE: DNA
<213> ORGANISM: Artificial Sequence
<220> FEATURE:
<223> OTHER INFORMATION: I-SceV Recognition sequence 3' from restriction
      site antisense strand

<400> SEQUENCE: 102
aataattttc ttcttagtaa t                                              21

```
<210> SEQ ID NO 103
<211> LENGTH: 24
<212> TYPE: DNA
<213> ORGANISM: Artificial Sequence
<220> FEATURE:
<223> OTHER INFORMATION: I-SceVI Recognition sequence

<400> SEQUENCE: 103
gttatttaat gttttagtag ttgg                                          24

<210> SEQ ID NO 104
<211> LENGTH: 11
<212> TYPE: DNA
<213> ORGANISM: Artificial Sequence
<220> FEATURE:
<223> OTHER INFORMATION: I-SceVI Recognition sequence 5' from
      restriction site sense strand

<400> SEQUENCE: 104
gttatttaat g                                                        11

<210> SEQ ID NO 105
<211> LENGTH: 13
<212> TYPE: DNA
<213> ORGANISM: Artificial Sequence
<220> FEATURE:
<223> OTHER INFORMATION: I-SceVI Recognition sequence 3' from
      restriction site sense strand

<400> SEQUENCE: 105
ttttagtagt tgg                                                      13

<210> SEQ ID NO 106
<211> LENGTH: 21
<212> TYPE: DNA
<213> ORGANISM: Artificial Sequence
<220> FEATURE:
<223> OTHER INFORMATION: I-SceVI Recognition sequence 3' from
      restriction site antisense strand

<400> SEQUENCE: 106
gttatttaat gttttagtag t                                             21

<210> SEQ ID NO 107
<211> LENGTH: 28
<212> TYPE: DNA
<213> ORGANISM: Artificial Sequence
<220> FEATURE:
<223> OTHER INFORMATION: I-SceVII Recognition sequence

<400> SEQUENCE: 107
tgtcacattg aggtgcacta gttattac                                      28

<210> SEQ ID NO 108
<211> LENGTH: 19
<212> TYPE: DNA
<213> ORGANISM: Artificial Sequence
<220> FEATURE:
<223> OTHER INFORMATION: I-Ssp6803I Recognition sequence

<400> SEQUENCE: 108
gtcgggctca tacccgaa                                                 19

<210> SEQ ID NO 109
<211> LENGTH: 11
<212> TYPE: DNA
<213> ORGANISM: Artificial Sequence
```

```
<220> FEATURE:
<223> OTHER INFORMATION: I-Ssp6803I Recognition sequence 3' from
      restriction site sense strand

<400> SEQUENCE: 109
cataacccga a                                                           11

<210> SEQ ID NO 110
<211> LENGTH: 11
<212> TYPE: DNA
<213> ORGANISM: Artificial Sequence
<220> FEATURE:
<223> OTHER INFORMATION: I-Ssp6803I Recognition sequence 3' from
      restriction site antisense strand

<400> SEQUENCE: 110
gtcgggctca t                                                           11

<210> SEQ ID NO 111
<211> LENGTH: 24
<212> TYPE: DNA
<213> ORGANISM: Artificial Sequence
<220> FEATURE:
<223> OTHER INFORMATION: I-TevI Recognition sequence

<400> SEQUENCE: 111
agtggtatca acgctcagta gatg                                             24

<210> SEQ ID NO 112
<211> LENGTH: 12
<212> TYPE: DNA
<213> ORGANISM: Artificial Sequence
<220> FEATURE:
<223> OTHER INFORMATION: I-TevI Recognition sequence 5' from restriction
      site sense strand

<400> SEQUENCE: 112
agtggtatca ac                                                          12

<210> SEQ ID NO 113
<211> LENGTH: 12
<212> TYPE: DNA
<213> ORGANISM: Artificial Sequence
<220> FEATURE:
<223> OTHER INFORMATION: I-TevI Recognition sequence 3' from restriction
      site sense strand

<400> SEQUENCE: 113
gctcagtaga tg                                                          12

<210> SEQ ID NO 114
<211> LENGTH: 10
<212> TYPE: DNA
<213> ORGANISM: Artificial Sequence
<220> FEATURE:
<223> OTHER INFORMATION: I-TevI Recognition sequence 3' from restriction
      site antisense strand

<400> SEQUENCE: 114
agtggtatca                                                             10

<210> SEQ ID NO 115
<211> LENGTH: 14
<212> TYPE: DNA
<213> ORGANISM: Artificial Sequence
<220> FEATURE:
<223> OTHER INFORMATION: I-TevI Recognition sequence 5' from restriction
``` site antisense strand

<400> SEQUENCE: 115
acgctcagta gatg                                                   14

<210> SEQ ID NO 116
<211> LENGTH: 30
<212> TYPE: DNA
<213> ORGANISM: Artificial Sequence
<220> FEATURE:
<223> OTHER INFORMATION: I-TevII Recognition sequence

<400> SEQUENCE: 116
gcttatgagt atgaagtgaa cacgttattc                                  30

<210> SEQ ID NO 117
<211> LENGTH: 25
<212> TYPE: DNA
<213> ORGANISM: Artificial Sequence
<220> FEATURE:
<223> OTHER INFORMATION: I-TevII Recognition sequence 5' from
      restriction site sense strand

<400> SEQUENCE: 117
gcttatgagt atgaagtgaa cacgt                                       25

<210> SEQ ID NO 118
<211> LENGTH: 23
<212> TYPE: DNA
<213> ORGANISM: Artificial Sequence
<220> FEATURE:
<223> OTHER INFORMATION: I-TevII Recognition sequence 3' from
      restriction site antisense strand

<400> SEQUENCE: 118
gcttatgagt atgaagtgaa cac                                         23

<210> SEQ ID NO 119
<211> LENGTH: 30
<212> TYPE: DNA
<213> ORGANISM: Artificial Sequence
<220> FEATURE:
<223> OTHER INFORMATION: I-TevIII Recognition sequence

<400> SEQUENCE: 119
tatgtatctt ttgcgtgtac ctttaacttc                                  30

<210> SEQ ID NO 120
<211> LENGTH: 29
<212> TYPE: DNA
<213> ORGANISM: Artificial Sequence
<220> FEATURE:
<223> OTHER INFORMATION: I-TevIII Recognition sequence 3' from
      restriction site sense strand

<400> SEQUENCE: 120
atgtatcttt tgcgtgtacc tttaacttc                                   29

<210> SEQ ID NO 121
<211> LENGTH: 28
<212> TYPE: DNA
<213> ORGANISM: Artificial Sequence
<220> FEATURE:
<223> OTHER INFORMATION: I-TevIII Recognition sequence 5' from
      restriction site antisense strand

<400> SEQUENCE: 121

```
tgtatctttt gcgtgtacct ttaacttc                                              28
```

<210> SEQ ID NO 122
<211> LENGTH: 22
<212> TYPE: DNA
<213> ORGANISM: Artificial Sequence
<220> FEATURE:
<223> OTHER INFORMATION: PI-TliI Recognition sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 122

```
taygcngaya cngacggytt yt                                                    22
```

<210> SEQ ID NO 123
<211> LENGTH: 17
<212> TYPE: DNA
<213> ORGANISM: Artificial Sequence
<220> FEATURE:
<223> OTHER INFORMATION: PI-TliI Recognition sequence 5' from
      restriction site sense strand
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 123

```
taygcngaya cngacgg                                                          17
```

<210> SEQ ID NO 124
<211> LENGTH: 13
<212> TYPE: DNA
<213> ORGANISM: Artificial Sequence
<220> FEATURE:
<223> OTHER INFORMATION: I-TliI Recognition sequence 3' from restriction
      site antisense strand
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 124

```
taygcngaya cng                                                              13
```

<210> SEQ ID NO 125
<211> LENGTH: 30
<212> TYPE: DNA
<213> ORGANISM: Artificial Sequence
<220> FEATURE:
<223> OTHER INFORMATION: PI-TliII Recognition sequence

<400> SEQUENCE: 125

```
aaattgcttg caaacagcta ttacggctat                                            30
```

<210> SEQ ID NO 126

```
<211> LENGTH: 19
<212> TYPE: DNA
<213> ORGANISM: Artificial Sequence
<220> FEATURE:
<223> OTHER INFORMATION: I-Tsp06II Recognition sequence

<400> SEQUENCE: 126
cttcagtatg ccccgaaac                                              19

<210> SEQ ID NO 127
<211> LENGTH: 10
<212> TYPE: DNA
<213> ORGANISM: Artificial Sequence
<220> FEATURE:
<223> OTHER INFORMATION: I-Tsp06II Recognition sequence 3' from
      restriction site sense strand

<400> SEQUENCE: 127
gccccgaaac                                                        10

<210> SEQ ID NO 128
<211> LENGTH: 14
<212> TYPE: DNA
<213> ORGANISM: Artificial Sequence
<220> FEATURE:
<223> OTHER INFORMATION: I-Tsp06II Recognition sequence 5' from
      restriction site antisense strand

<400> SEQUENCE: 128
gtatgccccg aaac                                                   14

<210> SEQ ID NO 129
<211> LENGTH: 24
<212> TYPE: DNA
<213> ORGANISM: Artificial Sequence
<220> FEATURE:
<223> OTHER INFORMATION: I-Vdi14II Recognition sequence

<400> SEQUENCE: 129
cctgactctc ttaaggtagc caaa                                        24

<210> SEQ ID NO 130
<211> LENGTH: 14
<212> TYPE: DNA
<213> ORGANISM: Artificial Sequence
<220> FEATURE:
<223> OTHER INFORMATION: I-Vdi14II Recognition sequence 5' from
      restriction site sense strand

<400> SEQUENCE: 130
cctgactctc ttaa                                                   14

<210> SEQ ID NO 131
<211> LENGTH: 10
<212> TYPE: DNA
<213> ORGANISM: Artificial Sequence
<220> FEATURE:
<223> OTHER INFORMATION: I-Vdi14II Recognition sequence 3' from
      restriction site sense strand

<400> SEQUENCE: 131
ggtagccaaa                                                        10

<210> SEQ ID NO 132
<211> LENGTH: 16
<212> TYPE: DNA
<213> ORGANISM: Artificial Sequence
```

<220> FEATURE:
<223> OTHER INFORMATION: I-Vdi14II Recognition sequence 5' from
      restriction site antisense strand

<400> SEQUENCE: 132
tcttaaggta gccaaa                                                 16

<210> SEQ ID NO 133
<211> LENGTH: 9
<212> TYPE: PRT
<213> ORGANISM: Artificial Sequence
<220> FEATURE:
<223> OTHER INFORMATION: consensus of HI family

<400> SEQUENCE: 133

Leu Ala Gly Leu Ile Asp Ala Asp Gly
1               5

<210> SEQ ID NO 134
<211> LENGTH: 69
<212> TYPE: DNA
<213> ORGANISM: Artificial Sequence
<220> FEATURE:
<223> OTHER INFORMATION: primer

<400> SEQUENCE: 134
gggagatctc cgccaagcga attgaaggac cgtgcgtaga atgaagaaca ttaagggttg   60
tcgacctgc                                                          69

<210> SEQ ID NO 135
<211> LENGTH: 70
<212> TYPE: DNA
<213> ORGANISM: Artificial Sequence
<220> FEATURE:
<223> OTHER INFORMATION: primer

<400> SEQUENCE: 135
gggtctagaa tgacaagagg gtcgaactcg cctaagtcgt aattgagtcc agatccacta   60
gtggcctatg                                                         70

<210> SEQ ID NO 136
<211> LENGTH: 99
<212> TYPE: DNA
<213> ORGANISM: Artificial Sequence
<220> FEATURE:
<223> OTHER INFORMATION: primer

<400> SEQUENCE: 136
gggtctagac cgccaagcga attgaaggac cgtgcgtaga atgaagaacc tatattaccc   60
tgttatccct agcgtaactt aagggttct cgagagctc                          99

<210> SEQ ID NO 137
<211> LENGTH: 99
<212> TYPE: DNA
<213> ORGANISM: Artificial Sequence
<220> FEATURE:
<223> OTHER INFORMATION: primer

<400> SEQUENCE: 137
gggagatcta tgacaagagg gtcgaactcg cctaagtcgt aattgagtca gttacgctag   60
ggataacagg gtaatatagc tgtttagctt gcctcgtcc                         99

<210> SEQ ID NO 138

```
<211> LENGTH: 18
<212> TYPE: DNA
<213> ORGANISM: Artificial Sequence
<220> FEATURE:
<223> OTHER INFORMATION: primer

<400> SEQUENCE: 138
gtatcacgag gcccttc                                                    18

<210> SEQ ID NO 139
<211> LENGTH: 20
<212> TYPE: DNA
<213> ORGANISM: Artificial Sequence
<220> FEATURE:
<223> OTHER INFORMATION: primer

<400> SEQUENCE: 139
caattcaacg cgtctgtgag                                                 20

<210> SEQ ID NO 140
<211> LENGTH: 18
<212> TYPE: DNA
<213> ORGANISM: Artificial Sequence
<220> FEATURE:
<223> OTHER INFORMATION: primer

<400> SEQUENCE: 140
tctttcctgc gttatccc                                                   18

<210> SEQ ID NO 141
<211> LENGTH: 22
<212> TYPE: DNA
<213> ORGANISM: Artificial Sequence
<220> FEATURE:
<223> OTHER INFORMATION: primer

<400> SEQUENCE: 141
ctcggtgagt tttctccttc at                                              22

<210> SEQ ID NO 142
<211> LENGTH: 43
<212> TYPE: DNA
<213> ORGANISM: Artificial Sequence
<220> FEATURE:
<223> OTHER INFORMATION: primer

<400> SEQUENCE: 142
catccgaaca taaacaacca tgaaggttgc aggatttata ttg                       43

<210> SEQ ID NO 143
<211> LENGTH: 51
<212> TYPE: DNA
<213> ORGANISM: Artificial Sequence
<220> FEATURE:
<223> OTHER INFORMATION: primer

<400> SEQUENCE: 143
caagaatctt tttattgtca gtactgatca ggcttgcaaa acaaattgtt c              51

<210> SEQ ID NO 144
<211> LENGTH: 43
<212> TYPE: DNA
<213> ORGANISM: Artificial Sequence
<220> FEATURE:
<223> OTHER INFORMATION: primer

<400> SEQUENCE: 144
```

```
caatataaat cctgcaacct tcatggttgt ttatgttcgg atg                    43
```

<210> SEQ ID NO 145
<211> LENGTH: 51
<212> TYPE: DNA
<213> ORGANISM: Artificial Sequence
<220> FEATURE:
<223> OTHER INFORMATION: primer

<400> SEQUENCE: 145

```
gaacaatttg ttttgcaagc ctgatcagta ctgacaataa aaagattctt g          51
```

<210> SEQ ID NO 146
<211> LENGTH: 110
<212> TYPE: DNA
<213> ORGANISM: Artificial Sequence
<220> FEATURE:
<223> OTHER INFORMATION: primer

<400> SEQUENCE: 146

```
gtaaaatcgt tggatctctc ttctaagtac atcctactat aacaatcaag aaaaacaaga    60
aaatcggaca aaacaatcaa gtatgcgctg caggtcgaca acccttaatg             110
```

<210> SEQ ID NO 147
<211> LENGTH: 110
<212> TYPE: DNA
<213> ORGANISM: Artificial Sequence
<220> FEATURE:
<223> OTHER INFORMATION: primer

<400> SEQUENCE: 147

```
gatgtaatca taacaaagcc taaaaaatag gtatatcatt ttataattat ttgctgtaca    60
agtatatcaa taaacttata tattagccgc ataggccact agtggatctg              110
```

<210> SEQ ID NO 148
<211> LENGTH: 410
<212> TYPE: PRT
<213> ORGANISM: Kluyveromyces lactis

<400> SEQUENCE: 148

```
Met Lys Val Ala Gly Phe Ile Leu Gly Ala Leu Ile Gln Phe Ser Leu
1               5                   10                  15

Thr Glu Gly His Val Glu Gln Asn Glu Asn Ala Asn Leu Thr Glu Met
                20                  25                  30

Trp Gly Glu Asp Trp Pro Phe Ser Gly Ile Gln Thr Phe Ala His Leu
            35                  40                  45

Pro His His Lys Cys Leu Ile Asp Met Glu Lys Lys Phe Asp Ile Gly
        50                  55                  60

Val Ile Gly Val Pro Phe Asp Thr Ala Val Ser Phe Arg Gly Gly Ala
65                  70                  75                  80

Arg Phe Gly Pro Gln Ala Ile Arg Lys Ala Ser Gln Arg Gln Thr Ser
                85                  90                  95

Met Arg Gly Phe Asn Phe Arg Ala Asp Ile Asn Pro Tyr Gln Asp Trp
            100                 105                 110

Ala Ser Val Val Asp Cys Gly Asp Val Pro Val Thr Pro Met Asp Asn
        115                 120                 125

Cys Leu Ala Leu Lys Met Met Thr Ala Ala Tyr Glu Asn Leu Leu Ser
    130                 135                 140

His Glu Ser Gln Thr Ser Asp Asn Asn Leu Pro Pro Arg Phe Val Thr
```

```
            145                 150                 155                 160
Leu Gly Gly Asp His Ser Ile Ile Leu Pro Ala Leu Arg Ala Leu Arg
                165                 170                 175
Lys Thr Tyr Gly Arg Leu Ala Val Ile His Phe Asp Ser His Leu Asp
            180                 185                 190
Thr Trp Ala Pro Ser Lys Tyr Pro Ser Phe Trp His Ser Asp Thr Ser
                195                 200                 205
Glu Phe Thr His Gly Ser Met Leu Trp Ile Ala His Asn Glu Gly Leu
            210                 215                 220
Leu Thr Glu Asn Asn Ile His Ala Gly Leu Arg Thr Arg Leu Ser
225                 230                 235                 240
Gly Ser Ser Phe Glu Asp Tyr Asp Asp Asp Lys Val Gly Phe His
                245                 250                 255
Arg Ile Glu Ala Asp Glu Ile Met Asp Gly Gly Ile Lys Ser Ile Val
            260                 265                 270
Glu Lys Ile Lys Ser Lys Ile Pro Ser Asp Val Pro Val Tyr Ile Ser
                275                 280                 285
Val Asp Ile Asp Val Leu Asp Pro Ser Ala Ala Pro Gly Thr Gly Thr
            290                 295                 300
Met Glu Val Gly Gly Trp Met Thr Arg Glu Leu Ile Arg Ile Ile Arg
305                 310                 315                 320
Glu Leu Glu Asp Leu Asn Leu Val Gly Ala Asp Ile Val Glu Val Ser
                325                 330                 335
Pro Pro Phe Asp Pro Thr Glu Ile Thr Ser Leu Ala Gly Ala Gln Ile
            340                 345                 350
Ala Tyr Glu Leu Ile Thr Asn Met Val Lys Lys Gly Pro Ile Asp Pro
            355                 360                 365
Glu Leu Ile Lys His Asn Leu Glu Leu Ser Asp Lys Leu Thr Gln Gly
            370                 375                 380
Gln Gln Leu Leu Gly Phe Ser Ser Pro Thr Asp Glu Leu Asn Asp Lys
385                 390                 395                 400
Ile Gln Lys Glu Gln Phe Val Leu Gln Ala
                405                 410

<210> SEQ ID NO 149
<211> LENGTH: 364
<212> TYPE: PRT
<213> ORGANISM: Zygosaccharomyces rouxii

<400> SEQUENCE: 149

Met Arg Phe Ser Thr Leu Ala Ser Leu Ala Ala Leu Phe Glu Phe Thr
1               5                   10                  15
Thr Ala Gly Arg Trp Thr Glu Asp Trp Pro Phe Ala Gly Phe Pro Ser
            20                  25                  30
Phe Ala Lys Leu Pro Phe His Thr Cys Leu Val Asp Asn Pro Glu Phe
        35                  40                  45
Asp Ile Ala Leu Ile Gly Val Pro Phe Asp Thr Ala Val Ser Phe Arg
    50                  55                  60
Pro Gly Ala Arg Phe Gly Pro Gln Ala Ile Arg Arg Ala Ser Gln Arg
65                  70                  75                  80
Gln Asn Gly Leu Arg Gly Phe Asn Ala Arg Ala Gly Ile Asn Pro Tyr
                85                  90                  95
Asp Asn Trp Ala His Ile Ile Asp Cys Gly Asp Ile Pro Val Thr Pro
            100                 105                 110
```

Met Asp Asn Gln Leu Ala Leu Glu Gln Met Asn Ala Ala Tyr Asp Glu
            115                 120                 125

Leu Val Asn Gly Thr Thr Thr Ser Gly Asn Thr Ala Gly Ala Leu Pro
        130                 135                 140

Arg Leu Val Ser Leu Gly Gly Asp His Ser Val Ile Leu Pro Ala Leu
145                 150                 155                 160

Arg Ala Leu His Lys His Tyr Gly Pro Ile Ser Val Ile His Leu Asp
                165                 170                 175

Ser His Leu Asp Thr Trp Ser Pro Asp Ser Tyr Pro Ser Tyr Trp His
            180                 185                 190

Ser Asn Thr Ser Glu Phe Thr His Gly Ser Met Leu Trp Leu Ala Ala
        195                 200                 205

Gln Glu Gly Leu Ile Asn Lys Gly His Cys Val His Gly Gly Leu Arg
210                 215                 220

Thr Arg Leu Ser Gly Asp Asp Trp Ser Asp Tyr Glu Glu Asp Asp Arg
225                 230                 235                 240

Val Gly Phe His Arg Ile His Ala Asp Glu Met Met Glu Ile Gly Pro
                245                 250                 255

Arg Gly Ile Ala Glu Arg Ile Lys Gln Ile Val Pro Lys Asn Val Pro
            260                 265                 270

Val Tyr Leu Ser Val Asp Ile Asp Val Leu Asp Pro Ser Ala Ala Pro
        275                 280                 285

Gly Thr Gly Thr Val Glu Pro Gly Gly Trp Leu Thr Arg Glu Leu Ile
290                 295                 300

Ser Leu Ile Arg Gln Leu Gln Asp Leu Pro Leu Val Gly Ala Asp Val
305                 310                 315                 320

Val Glu Val Ser Pro Pro Phe Asp His Ala Asp Val Thr Ala Met Ala
                325                 330                 335

Ala Ala Gln Val Ala Tyr Glu Ile Ile Thr Asn Met Val Lys Thr Pro
            340                 345                 350

Leu Glu Leu Glu Thr Arg Lys Phe Phe Ser Asn Met
        355                 360

<210> SEQ ID NO 150
<211> LENGTH: 361
<212> TYPE: PRT
<213> ORGANISM: Candida albicans

<400> SEQUENCE: 150

Met Lys Leu Leu Ala Leu Leu Thr Leu Leu Pro Leu Val Ile Ser Thr
1               5                   10                  15

Asn Leu Glu Glu Lys Trp Gly Gly Leu Trp Pro Phe Gln Gly Ile Ala
            20                  25                  30

Thr Phe Ala His Leu Glu His Phe Gln Cys Leu Ile Glu Ser Glu Lys
        35                  40                  45

Gln Phe Asp Ile Gly Ile Gly Val Pro Phe Asp Thr Ala Val Ser
    50                  55                  60

Tyr Arg Pro Gly Ala Arg Phe Gly Pro Arg Ala Ile Arg Asp Ala Ser
65                  70                  75                  80

Gln Arg Gln Asn Asn Leu Arg Gly Phe Asn Pro Lys Ala Leu Phe Asp
                85                  90                  95

Pro Tyr Gln Ser Trp Ala Arg Ile Ile Asp Cys Gly Asp Ile Pro Val
            100                 105                 110

Thr Pro Met Asp Asn Ser Ala Ala Tyr Lys Gln Met Ser Glu Ala Phe
        115                 120                 125

Lys Asp Leu Leu Asn Arg Lys Ser Ser Asn Asn Thr Glu Ile Pro Pro
            130                 135                 140

Arg Tyr Ile Ala Leu Gly Gly Asp His Ser Val Leu Leu Pro His Ile
145                 150                 155                 160

Arg Ala Leu His Lys Ile Tyr Gly Pro Val Asn Ile Ile His Phe Asp
                165                 170                 175

Ala His Leu Asp Thr Trp Lys Pro Asn Lys Tyr Pro Thr Ser Glu Lys
            180                 185                 190

Asn Asp Ile Asn His Gly Ser Met Leu Trp Lys Ala Tyr Glu Glu Gly
            195                 200                 205

Leu Thr Thr Lys His Asn Ile His Val Gly Val Arg Thr Arg Leu Ser
210                 215                 220

Glu Leu Asp Asp Leu Gln Asp Asp Glu Gln Asn Phe Val Arg Ile
225                 230                 235                 240

Glu Ala Asp Asp Ile Trp Leu Lys Gly Pro Gln Trp Val Val Asp Lys
                245                 250                 255

Ile Leu Ala Thr Ile Pro Lys Asp Thr Ala Thr Tyr Ile Ser Val Asp
                260                 265                 270

Val Asp Val Leu Asp Pro Gly Phe Thr Ser Gly Thr Gly Thr Gln Glu
            275                 280                 285

Pro Gly Gly Phe Leu Pro Arg Glu Leu Ile Tyr Leu Leu Arg Ser Ile
290                 295                 300

Asp Gly Leu Thr Val Val Gly Ala Asp Val Val Glu Val Ser Pro Ala
305                 310                 315                 320

Tyr Asp Ile Ala Glu Ile Thr Ala Thr Asn Gly Ala Gln Ile Ala Tyr
                325                 330                 335

Glu Val Leu Thr Ser Met Val Lys Arg Gly Asn Ile Asp Lys Ser Leu
            340                 345                 350

Val Lys Ser Val Val His Val Phe Asp
            355                 360

<210> SEQ ID NO 151
<211> LENGTH: 438
<212> TYPE: PRT
<213> ORGANISM: Debaryomyces hansenii

<400> SEQUENCE: 151

Met Lys Val Leu Asn Ile Ser Thr Ile Leu Phe Ile Ala Thr Thr Thr
1               5                   10                  15

Thr Ala Asn Gln Leu His Ser Asp Pro Phe Ser Asp Asn Val Val Tyr
            20                  25                  30

Phe Asp Thr His Ser Ala Glu Arg Glu Pro Asn Leu Lys Asp Met Trp
        35                  40                  45

Asp Asp Leu Trp Pro Phe Gln Gly Ile Asn Thr Phe Ala His Leu Glu
    50                  55                  60

His Asn Lys Cys Leu Leu Asp Pro Asp Gln Glu Tyr Asp Ile Gly Ile
65                  70                  75                  80

Ile Gly Val Pro Phe Asp Thr Ala Thr Ser Tyr Arg Pro Gly Ala Arg
                85                  90                  95

Phe Gly Pro Arg Ala Ile Arg Ser Ala Ser Gln Arg Gln Thr Ser Leu
            100                 105                 110

Arg Gly Tyr Asn Gln Arg Ala Asp Phe Asn Pro Tyr Thr Ser Trp Ala
        115                 120                 125

Lys Val Ile Asp Cys Gly Asp Met Pro Val Thr Pro Met Asp Asn Ser

```
              130                 135                 140
Leu Ala Phe Lys Gln Met Asn Lys Gly Phe Glu Glu Leu Ile Ala Arg
145                 150                 155                 160

Arg Asn Ser Lys Asn Ser Thr Val Thr Pro Arg Tyr Ile Ala Leu
                165                 170                 175

Gly Gly Asp His Ser Val Leu Leu Pro His Leu Arg Ala Leu His Glu
                180                 185                 190

Val Tyr Gly Lys Ile Asn Ile Leu His Phe Asp Ala His Leu Asp Thr
                195                 200                 205

Trp Gly Pro Asp Lys Tyr Pro Ser Phe Trp His Ser Lys Gln Ala Glu
                210                 215                 220

Leu Asn His Gly Ser Met Leu Trp Lys Ala Asn Lys Glu Cys Leu Thr
225                 230                 235                 240

Ser Glu His Asn Val His Ala Gly Val Arg Thr Lys Leu Ser Gly Ile
                245                 250                 255

Glu Asp Tyr Val Asp Asp Ser Gln Asn Phe Thr Arg Ile Thr Ala
                260                 265                 270

Asp Asp Ile Trp Ile Lys Gly Val Gln Tyr Val Val Asp Lys Ile Leu
                275                 280                 285

Glu Thr Ile Pro Pro Asp Thr Pro Thr Tyr Leu Ser Val Asp Ile Asp
                290                 295                 300

Val Leu Asp Pro Ala Phe Gly Ser Gly Thr Gly Thr Gln Glu Pro Gly
305                 310                 315                 320

Gly Trp Leu Pro Arg Glu Leu Ile His Val Leu Arg Ser Ile Glu Asn
                325                 330                 335

Leu Thr Ile Val Gly Ala Asp Ile Val Glu Val Ser Pro Ala Phe Asp
                340                 345                 350

Thr Ala Glu Ile Thr Ala Thr Asn Gly Ala Gln Val Val Phe Glu Ile
                355                 360                 365

Leu Thr Ser Met Val Lys Lys Gly Ser Val Gly His Leu Val Lys Asn
                370                 375                 380

Asn Asn Pro Lys Glu Leu Leu Glu Val Lys Ser Lys Asn Asp Gly Lys
385                 390                 395                 400

Ser Thr Gln Tyr Leu Asp Lys Gln Glu Ile Asn Arg Leu Ile Glu Asn
                405                 410                 415

Lys Leu Gln Glu Phe Glu Asn Ile Lys Phe Asn Leu Leu Ser Glu Ile
                420                 425                 430

Glu Gln Leu Arg Ser Thr
            435

<210> SEQ ID NO 152
<211> LENGTH: 361
<212> TYPE: PRT
<213> ORGANISM: Dekkera bruxellensis
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid

<400> SEQUENCE: 152
```

Met Pro Phe Pro Lys Ser Gln Ser Glu Ser Arg Lys Ser Pro Thr Leu
1               5                   10                  15

Glu Gln Leu Trp Gly Gln Xaa Trp Pro Phe Thr Gly Ile Pro Thr Phe
            20                  25                  30

Ala His Leu Asn Thr Thr Lys Cys Leu Leu Ser Pro Glu Ser Xaa Tyr
        35                  40                  45

Asp Ile Gly Ile Ile Gly Val Pro Phe Asp Thr Ala Thr Ser Tyr Arg
    50                  55                  60

Pro Gly Ala Arg Phe Gly Pro Gln Ala Ile Arg Leu Ala Ser Gln Arg
65                  70                  75                  80

Gln Asn Ser Met Arg Gly Phe Asn Thr Arg Ala Gly Ile Asn Pro Tyr
                85                  90                  95

Gln Asn Trp Ala Ser Leu Val Asp Cys Gly Asp Ile Pro Val Thr Pro
            100                 105                 110

Met Asp Asn Lys Val Ala Leu Asp Gln Met Thr Ala Ala Phe Glu Glu
        115                 120                 125

Leu Leu Leu Arg Arg Asn Ser Ser Leu Gly Asp Ala His Pro Pro Arg
    130                 135                 140

Tyr Val Ala Leu Gly Gly Asp His Ser Ile Ile Leu Pro His Leu Arg
145                 150                 155                 160

Ala Leu His Glu Val Tyr Gly Lys Ile Ala Val Ile His Phe Asp Ala
                165                 170                 175

His Leu Asp Thr Trp Thr Pro Xaa Lys Tyr Pro Ser Phe Trp Ser Ser
            180                 185                 190

Glu Gln Ser Lys Phe Thr His Gly Ser Met Leu Trp Met Ala Lys Lys
        195                 200                 205

Glu Gly Ile Leu Ser Asp Asp Tyr Asn Val His Val Gly Ile Arg Thr
    210                 215                 220

Arg Ile Ser Gly Val Ser Trp Glu Asp Phe Asp Glu Asp Asp Asp Gln
225                 230                 235                 240

Gly Trp Leu Arg Phe Ser Ala Asp Asp Val Trp Val Gly Gly Lys Gln
                245                 250                 255

Ser Leu Asp Gln Ile Val Ala Ser Ile Lys Lys Arg Ile Pro Ala His
            260                 265                 270

Tyr Pro Val Tyr Ile Ser Val Asp Val Asp Cys Met Asp Pro Gly Phe
    275                 280                 285

Thr Pro Gly Thr Gly Thr Ile Glu Pro Gly Gly Met Met Pro Arg Glu
290                 295                 300

Val Ile Tyr Leu Leu Arg His Leu Asp Leu Asp Leu Val Gly Ala Asp
305                 310                 315                 320

Val Val Glu Val Ala Pro Ala Tyr Asp Gln Ala Glu Ile Thr Ala Thr
                325                 330                 335

Asn Ala Ala Gln Val Val Phe Glu Leu Val Thr Thr Met Val Lys Arg
            340                 345                 350

Gly Lys Pro Leu Pro Val Arg Glu Asp
        355                 360

<210> SEQ ID NO 153
<211> LENGTH: 399
<212> TYPE: PRT
<213> ORGANISM: Kluyveromyces marxianus

<400> SEQUENCE: 153

Met Ile Asn Trp Ser Tyr Tyr Ala Leu Phe Cys Leu Ala Ile Val Pro
1               5                   10                  15

Phe Ala Lys Cys Glu Tyr Tyr Asn Glu Asp Ile Gly Thr Asn Ser Thr
            20                  25                  30

Leu Asn Asp Met Trp Gly Glu Trp Pro Phe Ser Gly Ile Gln Thr
        35                  40                  45

Phe Ala His Leu Pro His Gln Lys Cys Leu Leu Asp Met Gly Thr Lys
 50                  55                  60

Phe Asp Ile Gly Val Ile Gly Met Pro Phe Asp Thr Ala Val Ser Tyr
 65                  70                  75                  80

Arg Pro Gly Ala Arg Phe Gly Pro Gln Gly Ile Arg Lys Ala Ser Gln
                85                  90                  95

Arg Gln Asn Ser Met Arg Gly Phe Asn Phe Arg Ala Gly Ile Asn Pro
            100                 105                 110

Tyr Asn Asn Trp Ala Ser Val Ile Asp Cys Gly Asp Val Pro Val Thr
        115                 120                 125

Pro Met Asp Asn Asn Leu Ala Leu Gln Met Met Thr Ala Ala Tyr Asp
130                 135                 140

Asn Leu Leu Ser His Glu Ser Lys Ala Glu Ser Asn Glu Leu Pro Pro
145                 150                 155                 160

Arg Leu Val Thr Leu Gly Gly Asp His Ser Ile Ile Leu Pro Ala Leu
                165                 170                 175

Arg Ser Leu His Lys Leu Tyr Gly Arg Leu Ala Val Ile His Phe Asp
            180                 185                 190

Ser His Leu Asp Thr Trp Ser Pro Ser Lys Tyr Pro Ser Phe Trp His
        195                 200                 205

Ser Asp Thr Ser Glu Phe Thr His Gly Ser Met Leu Trp Ile Ala His
210                 215                 220

Asn Glu Gly Leu Ile Thr Glu Asn Ser Asn Val His Ala Gly Leu Arg
225                 230                 235                 240

Thr Arg Leu Ser Gly Thr Ser Tyr Glu Asp Tyr Asp Glu Asp Asp Gln
                245                 250                 255

Val Gly Phe Tyr Arg Ile Glu Ala Asp Glu Ile Met Asp Gly Gly Pro
            260                 265                 270

Ser Ala Ile Val Glu Lys Ile Lys Ser Lys Ile Pro Asp Asn Val Pro
        275                 280                 285

Val Tyr Ile Ser Val Asp Ile Asp Val Leu Asp Pro Ser Ala Ala Pro
290                 295                 300

Gly Thr Gly Thr Met Glu Ala Gly Gly Trp Leu Thr Arg Glu Leu Ile
305                 310                 315                 320

Arg Ile Ile Arg Gln Leu Asp His Leu Asn Leu Val Gly Ala Asp Val
                325                 330                 335

Val Glu Val Ser Pro Pro Phe Asp Pro Ser Glu Ile Thr Thr Leu Ala
            340                 345                 350

Gly Ala Gln Val Ala Tyr Glu Leu Ile Thr Asn Met Val Lys Lys Gly
        355                 360                 365

Pro Leu Asp Pro Asp Met Val Lys Arg Asn Leu Glu Ser Lys Asn Ala
        370                 375                 380

Asn His Phe Gln Met Gln Gln Asn Glu Gln Asn Val Leu His Ile
385                 390                 395

<210> SEQ ID NO 154
<211> LENGTH: 350
<212> TYPE: PRT
<213> ORGANISM: Lachancea waltii

<400> SEQUENCE: 154

Met Pro Phe Asp Thr Ala Val Ser Tyr Arg Pro Gly Ala Arg Phe Gly
1               5                   10                  15

Pro Gln Ala Ile Arg Arg Ser Ser Gln Arg Gln Asn Ser Met Arg Gly
            20                  25                  30

Phe Asn Ser Arg Ala Gly Ile Asn Pro Tyr Gln Asn Trp Ala Lys Ile
        35                  40                  45

Met Asp Cys Gly Asp Val Pro Val Thr Pro Met Asp Asn Gln Leu Ala
    50                  55                  60

Leu Lys Met Met Thr Ser Ala Tyr Glu Thr Leu Leu Asn His Ser Ser
65                  70                  75                  80

Thr Thr Lys Asp Ser Lys Leu Pro Pro Arg Leu Val Thr Leu Gly Gly
                85                  90                  95

Asp His Ser Ile Leu Leu Pro Val Leu Arg Ser Leu Lys Glu Val Tyr
            100                 105                 110

Gly Pro Ile Ala Val Ile His Phe Asp Ser His Leu Asp Thr Trp Ala
        115                 120                 125

Pro Ala Lys Tyr Pro Ser Phe Trp His Ser Asp Thr Ser Glu Phe Thr
    130                 135                 140

His Gly Ser Met Leu Trp Leu Ala Ser Gln Glu Gly Leu Leu Ser Gly
145                 150                 155                 160

Gly His Asn Val His Ala Gly Leu Arg Thr Arg Leu Ser Gly Thr Ser
                165                 170                 175

Trp Glu Asp Tyr Asp Glu Asp Glu Val Gly Phe Tyr Arg Ile Gln
            180                 185                 190

Ala Asp Glu Ile Met Asp Ile Gly Val His Gly Val Ala Lys Lys Ile
        195                 200                 205

Ile Glu Arg Val Pro Lys Asp Ile Pro Val Tyr Ile Ser Val Asp Ile
    210                 215                 220

Asp Val Leu Asp Pro Ser Ala Ala Pro Gly Thr Gly Thr Met Glu Val
225                 230                 235                 240

Gly Gly Trp Leu Thr Arg Glu Leu Ile Ser Ile Ile Arg Lys Leu Glu
                245                 250                 255

Asp Leu Thr Leu Val Gly Ala Asp Ile Val Glu Val Ser Pro Ala Tyr
            260                 265                 270

Asp Ser Gly Asp Val Thr Ser Leu Ala Ala Gln Ile Ala Tyr Glu
        275                 280                 285

Leu Ile Thr Asn Met Val Lys Lys Gly Pro Val Ala Asp Glu Ile Val
    290                 295                 300

Glu Lys Asn Lys Gln Ile Ala Glu Asn Leu Ala Glu Asn Asn His Val
305                 310                 315                 320

Arg Val Thr Glu Gln Gly Thr Thr Lys Ile Leu Glu Arg Leu Ile Gln
                325                 330                 335

Asp Ala Asn Gln Ala Val Leu His Ala Thr Asn Pro Leu Leu
            340                 345                 350

<210> SEQ ID NO 155
<211> LENGTH: 396
<212> TYPE: PRT
<213> ORGANISM: Yarrowia lipolytica

<400> SEQUENCE: 155

Met Asp Ser Glu Tyr Gly Asp Leu Ser Val Glu Gln Lys Pro Ile Lys
1               5                   10                  15

Asp His Ser His Ser His His His Asp His Gly His Gly His Gly
                20                  25                  30

Asn Gly His Val Glu Val Glu Tyr Leu Asn Leu Pro Gly Asn Asn Phe
            35                  40                  45

Tyr Glu Asp Leu Asp Ala Glu Leu Asn Gly Pro Leu Tyr Ala Gly Ile
 50                  55                  60

Gln Thr Phe Ala His Leu Gly His Val Ser Cys Phe Asp Pro Thr Asn
 65                  70                  75                  80

Phe Ala Ser Glu Gln Phe Asp Ile Ala Leu Val Gly Ala Pro Phe Asp
                 85                  90                  95

Thr Ala Val Thr Phe Arg Ser Gly Ala Arg Phe Gly Pro Ala Gly Ile
                100                 105                 110

Arg Lys Gly Ser Arg Arg Met Ser Pro Gly Gln Val Ser Pro Tyr Arg
            115                 120                 125

Glu Gly Phe Met Leu Tyr Asp Asp Trp Ala Lys Phe Val Asp Cys Gly
130                 135                 140

Asp Val Ala Met His Pro Leu Asp Asn Arg Tyr Ala Leu Asn Gln Leu
145                 150                 155                 160

Tyr Arg Gly Met Arg Ala Ile His Asn His Thr Thr Ser Thr Leu Asn
                165                 170                 175

Ala Thr His Ile Pro Arg Ala Ile Leu Met Gly Gly Asp His Thr Thr
            180                 185                 190

Thr Leu Ser Ala Leu Gln Ala Ile Tyr Glu Lys Ile Gly Pro Val Ser
        195                 200                 205

Val Ile His Phe Asp Ser His Ile Asp Thr Trp Asp Pro Met Val Leu
    210                 215                 220

Gly Gly Asn Val Ser Ser Tyr Met Gln Val Asn His Gly Thr Phe Leu
225                 230                 235                 240

His Tyr Ala Ala Glu Arg Gly Tyr Leu Asn His Gly His Asn Leu His
                245                 250                 255

Val Gly Ser Arg Ala Pro Tyr Val Arg Lys His Gly Asp Ile Glu His
            260                 265                 270

Asp Lys His Cys Gly Phe Ala Ile Val Asn Ala Arg Glu Ile Asp Glu
        275                 280                 285

Val Gly Ile Ala Gly Val Val Gln Lys Ile Lys Asp Arg Val Gly Asn
    290                 295                 300

Thr Asn Val Tyr Ile Ser Val Asp Ile Asp Val Leu Asp Pro Val Tyr
305                 310                 315                 320

Ala Pro Gly Thr Gly Thr Ala Glu Pro Gly Gly Tyr Thr Thr Arg Glu
                325                 330                 335

Phe Met Gln Ile Leu Asp Gly Leu Glu Gly Ile Asn Ile Val Gly Ala
            340                 345                 350

Asp Val Val Glu Val Ala Pro Ala Tyr Asp Gly Pro Gly Asp Val Thr
        355                 360                 365

Leu Leu Ala Ala Ala Gln Val Ile Asp Ser Leu Ala Ser Leu Met Val
    370                 375                 380

Met Asn Gly Pro Leu Ser Thr Arg Gln Ser Thr Lys
385                 390                 395

<210> SEQ ID NO 156
<211> LENGTH: 360
<212> TYPE: PRT
<213> ORGANISM: Ogataea parapolymorpha

<400> SEQUENCE: 156

Met Ala Val Ala Lys Ala Leu Gln Ser Pro Ile Gln Phe Ala Ser Asn
1               5                   10                  15

Ser Glu Pro Thr Leu Asp Gln Leu Trp Gly Glu Asp Trp Pro Phe Asn
                20                  25                  30

Gly Ile Gln Thr Phe Ala His Leu Asn Tyr Thr Lys Cys Leu Val Asp
            35                  40                  45

Pro Glu Thr Ser Phe Asp Ile Gly Val Ile Gly Val Pro Phe Asp Thr
        50                  55                  60

Ala Thr Thr Tyr Arg Ser Gly Ala Arg Phe Gly Pro Arg Ala Ile Arg
65                  70                  75                  80

Thr Gly Ser Gln Arg Gln Thr Ser Lys Arg Ala Phe Asn Thr Arg Ala
                85                  90                  95

Gly Ile Asn Pro Tyr Gln Asp Trp Ala Lys Val Ile Asp Cys Gly Asp
            100                 105                 110

Ile Pro Val Thr Pro Met Asp Asn Glu Leu Ala Leu Asp Gln Met Thr
        115                 120                 125

Lys Ala Phe Glu Glu Leu Leu Leu Lys Arg Lys Asn Ala Val Asp Gly
130                 135                 140

Ser Gly Pro Pro Lys Leu Val Ala Leu Gly Gly Asp His Ser Ile Leu
145                 150                 155                 160

Leu Pro His Leu Arg Ala Leu Asn Lys Val Tyr Gly Lys Val Ala Val
                165                 170                 175

Ile His Phe Asp Ala His Leu Asp Thr Trp Ser Pro Ser Lys Tyr Pro
            180                 185                 190

Ser Phe Trp Ser Ser Asp Gln Ser Lys Phe Thr His Gly Ser Met Leu
        195                 200                 205

Trp Met Ala Asn Glu Glu Asp Leu Leu Ser Asp Tyr Asn Val His
210                 215                 220

Ile Gly Leu Arg Thr Arg Ile Ser Gly Lys Trp Glu Asp Tyr Glu
225                 230                 235                 240

Asp Asp Asp Asp Gln Gly Trp Ala Arg Phe Ser Ala Asp Ile Trp
                245                 250                 255

Ile Asn Gly Leu Gly Gly Leu Lys Glu Ile Val Arg Ser Ile Asn Glu
            260                 265                 270

Arg Ile Pro Lys Asp Tyr Pro Thr Tyr Val Ser Val Asp Ile Asp Cys
        275                 280                 285

Leu Asp Pro Gly Phe Ala Pro Gly Thr Gly Thr Ile Glu Ser Gly Gly
290                 295                 300

Leu Leu Pro Arg Glu Leu Phe Tyr Leu Leu Arg Asn Ile Asp Val Asn
305                 310                 315                 320

Leu Val Gly Ala Asp Ile Val Glu Val Ser Pro Gln Tyr Asp His Ala
                325                 330                 335

Glu Ile Thr Ala Thr Asn Gly Ala Glu Val Ala Tyr Gln Leu Ile Thr
            340                 345                 350

Ser Ile Val Lys Gln Gly Lys Lys
        355                 360

<210> SEQ ID NO 157
<211> LENGTH: 412
<212> TYPE: PRT
<213> ORGANISM: Lachancea thermotolerans

<400> SEQUENCE: 157

Met Leu Met Arg Ser Val Leu Phe Ser Leu Ala Cys Ala Asn Ala Val

```
1               5                   10                  15
Leu Ala Ser Gly Thr Thr Val Leu Glu Glu Asp Leu Glu Gln Met Trp
             20                  25                  30
Gly Gln Asp Trp Pro Phe Ser Gly Ile Gln Thr Phe Ala His Leu Pro
             35                  40                  45
His Glu Lys Cys Leu Met Asn Arg Ser Leu Asp Phe Asp Ile Gly Val
             50                  55                  60
Ile Gly Ile Pro Phe Asp Thr Ala Val Thr Tyr Arg Pro Gly Ala Arg
65                   70                  75                  80
Phe Gly Pro Gln Ala Ile Arg Lys Ser Ser Gln Arg Gln Thr Ser Met
             85                  90                  95
Arg Gly Phe Asn Phe Arg Ala Gly Ile Asn Pro Tyr Gln Asp Trp Ala
             100                 105                 110
Lys Val Leu Asp Cys Gly Asp Val Pro Val Thr Pro Met Asp Asn Asn
             115                 120                 125
Leu Ala Leu Gln Met Met Gly Ala Ala Tyr His Asn Leu Leu Asn Arg
             130                 135                 140
Asn Ser Thr Leu Lys Gln Ala Glu Leu Pro Pro Arg Phe Ala Thr Leu
145                  150                 155                 160
Gly Gly Asp His Ser Ile Ile Leu Pro Ile Leu Arg Gln Leu His Lys
             165                 170                 175
Ile Tyr Gly Pro Ile Ser Val Ile His Phe Asp Ser His Leu Asp Thr
             180                 185                 190
Trp Ala Pro Ser Lys Tyr Pro Ser Tyr Trp His Ser Asn Asn Ser Asp
             195                 200                 205
Phe Thr His Gly Ser Met Leu Trp Ile Ala Lys Gln Glu Gly Leu Leu
210                  215                 220
Ser Glu Asn Ser Asn Val His Ala Gly Leu Arg Thr Arg Leu Ser Gly
225                  230                 235                 240
Val Gly Trp Asp Asp Tyr Glu Glu Asp Lys Glu Thr Gly Phe His Arg
             245                 250                 255
Ile Glu Cys Asp Glu Ile Leu Asp Ile Gly Val Arg Gly Ile Ala Arg
             260                 265                 270
Lys Ile Leu Asp Ile Val Pro Lys Asp Lys Pro Val Tyr Ile Ser Val
             275                 280                 285
Asp Ile Asp Val Leu Asp Pro Ser Ala Ala Pro Gly Thr Gly Thr Val
             290                 295                 300
Glu Val Gly Gly Leu Leu Thr Arg Glu Leu Ile Ser Ile Ile Arg Gln
305                  310                 315                 320
Leu Asp Gly Leu Ser Leu Ile Gly Ala Asp Val Val Glu Val Ser Pro
             325                 330                 335
Ala Tyr Asp Gln Ser Asp Ile Thr Ser Thr Ala Ala Ser Gln Ile Val
             340                 345                 350
Tyr Glu Leu Ile Thr Asn Met Val Lys Lys Gly Pro Leu Asp Pro Ala
             355                 360                 365
Met Ile Gln Ala Asn Lys Asn Ser Glu Met Asp Gln Gly Asp Lys Pro
             370                 375                 380
Gln Asn Leu Ala Glu Asn Glu Tyr Gln Ser Leu Gly Glu Gly Ala Arg
385                  390                 395                 400
Gln Asn Phe Met Glu Ser Leu Leu Gln Gly Arg Val
             405                 410

<210> SEQ ID NO 158
```

<211> LENGTH: 366
<212> TYPE: PRT
<213> ORGANISM: Lodderomyces elongisporus

<400> SEQUENCE: 158

Met Lys Leu Leu Leu Thr Leu Leu Gly Ile Leu Gln Val Cys Ile Ala
1               5                   10                  15

Thr Asp Leu Glu Glu Lys Trp Gly Ser Leu Trp Gln Phe Gln Gly Ile
            20                  25                  30

Ala Thr Phe Ala His Leu Glu His Thr Gln Cys Leu Val Asn Pro Lys
        35                  40                  45

Glu Ser Phe Asp Val Ala Val Ile Gly Val Pro Phe Asp Thr Ala Val
    50                  55                  60

Ser Tyr Arg Pro Gly Ala Arg Phe Gly Pro Arg Ala Ile Arg Asp Ala
65                  70                  75                  80

Ser Gln Arg Gln Tyr Ser Leu Arg Gly Phe Asn His Arg Ala Leu Phe
                85                  90                  95

Asn Pro Tyr Lys Ser Trp Ala Lys Ile Ile Asp Cys Gly Asp Ile Pro
            100                 105                 110

Val Thr Pro Met Asp Asn His Leu Ala Phe Lys Gln Met Asp Ile Ala
        115                 120                 125

Phe Asp Glu Leu Leu Gln Arg Ser Ser Ala Asn Asp Ser Arg Val Pro
    130                 135                 140

Pro Arg Tyr Val Val Leu Gly Gly Asp His Ser Val Leu Leu Pro His
145                 150                 155                 160

Leu Arg Ala Leu Lys Lys His Tyr Gly Arg Leu Asn Val Leu His Phe
                165                 170                 175

Asp Ala His Leu Asp Thr Trp Ser Pro Leu Lys Tyr Pro Ser Phe Trp
            180                 185                 190

Arg Thr Asp Gln Asn Asp Leu Asn His Gly Ser Met Leu Trp Gln Ala
        195                 200                 205

His Glu Glu Gly Leu Thr Thr Asn Arg Asn Val His Ala Gly Val Arg
    210                 215                 220

Thr Lys Leu Ser Gly Ile Glu Asp Tyr Gln Asp Asp Ala Gln Asn
225                 230                 235                 240

Trp Val Arg Ile Glu Ala Asp Ile Trp Leu Lys Gly Pro Gln Tyr
                245                 250                 255

Val Val Asp Lys Ile Leu Glu Thr Ile Pro Lys Asp Ser Pro Thr Tyr
            260                 265                 270

Leu Ser Val Asp Ile Asp Val Leu Asp Pro Gly Phe Ala Ser Gly Thr
        275                 280                 285

Gly Thr Gln Glu Ser Gly Gly Trp Leu Pro Arg Glu Leu Ile His Ile
    290                 295                 300

Leu Arg Gly Val Glu Glu Leu Thr Ile Val Gly Ala Asp Val Val Glu
305                 310                 315                 320

Val Ala Pro Ala Tyr Asp Val Ser Glu Val Thr Ala Thr Asn Gly Ala
                325                 330                 335

Gln Met Ala Phe Glu Ile Leu Thr Ser Met Val Lys Lys Gly Asn Val
            340                 345                 350

Asp Lys Asn Ile Val Asp Arg Thr Ile Glu Ile Phe Glu Ser
        355                 360                 365

<210> SEQ ID NO 159
<211> LENGTH: 404
<212> TYPE: PRT

-continued

<213> ORGANISM: Meyerozyma guilliermondii

<400> SEQUENCE: 159

```
Met Lys Leu Leu Pro Leu Leu Phe Ala Thr Ala Leu Ala Gln Leu Thr
1               5                   10                  15

Leu Lys Asn Asp Asn Val Val Tyr Asp Ser Asn Pro Pro Ser Leu Ser
            20                  25                  30

Glu Met Trp Asp Gly Leu Trp Pro Phe Gln Gly Ile Asn Thr Phe Ala
        35                  40                  45

His Leu Asp His Lys Val Cys Leu Thr Gln Pro Asp Glu Ile Tyr Asp
    50                  55                  60

Phe Ala Ile Ile Gly Val Pro Phe Asp Thr Ala Val Leu Tyr Arg Pro
65                  70                  75                  80

Gly Ala Arg Phe Gly Pro Arg Ala Ile Arg Ala Ala Gln Arg Gln
                85                  90                  95

Thr Ser Leu Arg Gly Tyr Asn Gln Arg Ala Asn Phe Asn Pro Tyr Thr
            100                 105                 110

Ser Trp Ala Lys Val Leu Asp Cys Gly Asp Ile Pro Val Thr Pro Met
        115                 120                 125

Asp Asn His Leu Ala Phe Lys Gln Met Asp Leu Ala Phe Glu Glu Leu
    130                 135                 140

Ile Leu Arg Arg Asn Ser Ser Ser Lys Ala Pro Pro Arg Tyr Ile Ala
145                 150                 155                 160

Leu Gly Gly Asp His Ser Val Leu Leu Pro His Leu Arg Ala Leu Lys
                165                 170                 175

Lys Ala Tyr Gly Pro Leu Asn Val Ile His Phe Asp Ala His Leu Asp
            180                 185                 190

Thr Trp Ser Pro Asp Lys Tyr Pro Ser Phe Trp His Ser Asp Gln Ser
        195                 200                 205

Glu Ile Thr His Gly Ser Met Leu Trp Thr Ala Phe Glu Glu Gly Leu
    210                 215                 220

Thr Thr Asn Thr Asn Ile His Ala Gly Leu Arg Thr Lys Leu Ser Gly
225                 230                 235                 240

Leu Glu Asp Tyr Glu Asp Asp Lys Gln Asn Phe Val Arg Ile Tyr
                245                 250                 255

Ala Asp Asp Ile Trp Ile Asp Gly Val Gln Ser Val Ile Ala Lys Ile
            260                 265                 270

Asn Ala Thr Ile Pro Ala Asp Thr Pro Thr Tyr Ile Ser Val Asp Ile
        275                 280                 285

Asp Val Leu Asp Pro Gly Phe Gly Ser Gly Thr Gly Thr Gln Glu Pro
    290                 295                 300

Gly Gly Trp Leu Pro Arg Glu Leu Ile Tyr Val Leu Arg His Ile Asp
305                 310                 315                 320

His Leu Thr Ile Val Gly Gly Asp Val Val Glu Val Ser Pro Ala Phe
                325                 330                 335

Asp Asn Ala Glu Ile Thr Ala Thr Asn Gly Ala Gln Val Ala Tyr Glu
            340                 345                 350

Leu Leu Thr Ser Met Val Lys Lys Gly Arg Val Asp Leu Leu Val Gln
        355                 360                 365

Arg Glu Glu Ala Thr Pro Ile Ile Lys Ser Ser Glu Val Glu Leu Thr
    370                 375                 380

Leu Glu Glu Arg Leu Thr Ser Gly Ile Arg Gln Leu Lys Asn Met Gln
385                 390                 395                 400
```

Ala Leu Phe Asn

<210> SEQ ID NO 160
<211> LENGTH: 417
<212> TYPE: PRT
<213> ORGANISM: Millerozyma farinosa

<400> SEQUENCE: 160

```
Met Leu Lys Ser Ile Ser Tyr Trp Ala Phe Ile Leu Ser Ile Tyr Leu
1               5                   10                  15

Gly Val Val Cys Ala Asp Glu Ala Glu Gln Ile Ala Ser Ala Glu Gly
                20                  25                  30

Phe Ala Lys Met Gln Arg Asn Ala Thr Leu Glu Glu Met Trp Gly Glu
            35                  40                  45

Leu Trp Pro Phe Gln Gly Ile Asn Thr Phe Ala His Leu Glu His Phe
    50                  55                  60

Lys Cys Leu Val Glu Gln Asp Glu Lys Tyr Asp Ile Gly Ile Gly
65                  70                  75                  80

Val Pro Tyr Asp Thr Ser Val Ser Tyr Arg Pro Gly Ala Arg Phe Gly
                85                  90                  95

Pro Arg Ala Ile Arg Thr Ala Ser Gln Arg Gln Thr Ser Leu Arg Gly
            100                 105                 110

Phe Asn Gln Arg Ala Phe Phe Asn Pro Tyr Thr Ser Trp Ala Arg Ile
        115                 120                 125

Val Asp Cys Gly Asp Val Pro Val Thr Pro Val Asp Asn Glu Leu Ala
130                 135                 140

Phe Lys Gln Met Thr Ala Ala Phe Glu Glu Leu Leu Leu Arg Arg Ser
145                 150                 155                 160

Ala Lys Asn Asp Ser Ser Met Pro Pro Arg His Ile Ile Leu Gly Gly
                165                 170                 175

Asp His Ser Val Ile Leu Pro His Leu Arg Ala Leu Ser Lys Val His
            180                 185                 190

Gly Pro Ile Asn Val Ile His Leu Asp Ala His Leu Asp Thr Trp Ala
        195                 200                 205

Pro Asp Lys Tyr Pro Ser Phe Trp His Ser Ala Gln Ser Glu Val Asn
    210                 215                 220

His Gly Ser Met Leu Trp Lys Ala His Gln Glu Gly Leu Leu Ser His
225                 230                 235                 240

Asn Asn Val His Ala Gly Leu Arg Thr Lys Leu Ser Gly Ile Ala Asp
                245                 250                 255

Tyr Glu Asp Asp Asp Ala Gln His Phe Thr Arg Ile Thr Ala Asp Asp
            260                 265                 270

Ile Trp Ile Lys Gly Pro Asp Tyr Val Leu Asp Thr Ile Leu Lys Val
        275                 280                 285

Val Pro Ala Asn Thr Pro Thr Tyr Ile Ser Val Asp Ile Asp Val Leu
    290                 295                 300

Asp Pro Ala Phe Gly Ser Gly Thr Gly Thr Gln Glu Pro Gly Gly Trp
305                 310                 315                 320

Leu Pro Arg Glu Leu Ile Tyr Ile Leu Arg Gly Leu Glu Asn Leu Asp
                325                 330                 335

Val Val Gly Ala Asp Ile Val Glu Val Ser Pro Ala Phe Asp Ile Ala
            340                 345                 350

Glu Ile Thr Ala Thr Asn Gly Ala Gln Val Val Phe Glu Ile Leu Thr
        355                 360                 365
```

```
Ser Ile Val Lys Lys Gly Asn Ser Glu Lys Val Ala Asp Ser Ser Ser
    370                 375                 380

Gln Lys Asp Lys Gly Ser Ser Ala Ala Leu Gln Asp Asp Lys Ile Lys
385                 390                 395                 400

Gln Gln Lys Gln Asp Val Leu Thr Arg Lys Asn Pro Phe Val Ile Ser
                405                 410                 415

Asn

<210> SEQ ID NO 161
<211> LENGTH: 440
<212> TYPE: PRT
<213> ORGANISM: Scheffersomyces stipitis

<400> SEQUENCE: 161

Met Lys Cys Ser His Ile Val Ser Ala Pro Ile Phe Leu Ser Val Ala
1               5                   10                  15

Ala Ala Val Leu Gln Pro Val Ala Trp Lys Ser Asp Glu Leu Ile Asn
                20                  25                  30

Asp Ser Ile Asp Gly Ser Ser Pro Ser Leu Lys Glu Met Trp Asp Asp
            35                  40                  45

Leu Trp Pro Phe Gln Gly Ile Asn Thr Phe Ala His Leu Asp His His
    50                  55                  60

Lys Cys Leu Leu Glu Pro Gly Asn Thr Tyr Asp Val Ala Leu Ile Gly
65                  70                  75                  80

Val Pro Phe Asp Thr Ala Val Ser Tyr Arg Pro Gly Ala Arg Phe Gly
                85                  90                  95

Pro Arg Ala Ile Arg Ala Ala Ser Gln Arg Gln Thr Ser Leu Arg Gly
                100                 105                 110

Tyr Asn Gln Arg Ala Asn Phe Asn Pro Tyr Ala Ser Trp Ala Lys Ile
                115                 120                 125

Val Asp Cys Gly Asp Leu Pro Ile Thr Pro Met Asp Asn Ser Ile Ala
130                 135                 140

Phe Thr Gln Met Thr Lys Gly Phe Glu Glu Leu Leu Leu Arg Arg Ser
145                 150                 155                 160

Ser Asn Ser Ser Ser Glu Leu Pro Pro Arg Tyr Val Ala Leu Gly Gly
                165                 170                 175

Asp His Ser Val Leu Leu Pro His Leu Arg Ala Leu His Glu Val Tyr
                180                 185                 190

Gly Arg Ile Asn Val Ile His Phe Asp Ala His Leu Asp Thr Trp Ala
                195                 200                 205

Pro Asp Lys Tyr Pro Ser Phe Trp His Ser Asp Gln Ser Glu Ile Asn
    210                 215                 220

His Gly Ser Met Leu Trp Lys Ala His His Glu Gly Leu Thr Ser His
225                 230                 235                 240

His Asn Val His Ala Gly Leu Arg Thr Lys Leu Ser Gly Leu Glu Asp
                245                 250                 255

Tyr Glu Asp Asp Asp Ser Gln His Phe Ile Arg Ile Asp Ala Asp Asp
                260                 265                 270

Ile Trp Leu Lys Gly Pro Gln Trp Val Val Gln Lys Ile Leu Asp Thr
    275                 280                 285

Val Pro Asp Asp Ser Pro Thr Tyr Ile Ser Val Asp Val Asp Val Leu
            290                 295                 300

Asp Pro Gly Phe Thr Ser Gly Thr Gly Thr Gln Glu Pro Gly Gly Trp
305                 310                 315                 320
```

Leu Pro Arg Glu Leu Leu His Val Leu Arg Ser Ile Glu Gly Leu Thr
            325                 330                 335

Val Val Gly Gly Asp Val Val Glu Val Ser Pro Ala Phe Asp Thr Ala
        340                 345                 350

Glu Ile Thr Ser Thr Asn Gly Ala Gln Ile Ala Phe Glu Ile Ile Thr
            355                 360                 365

Ser Met Val Lys Lys Gly Pro Ile Asp Pro Ala Ile Val Lys Lys Asn
370                 375                 380

Lys Lys Glu Leu Val Lys Ile Thr His Val Asn Glu Leu Glu Gln Glu
385                 390                 395                 400

Lys Lys Asp Phe Ile Asp Leu Glu Lys Ala Lys Lys Thr Ile Glu Gln
            405                 410                 415

Lys Leu Lys Glu Leu Asp Glu Leu Lys Ser Glu Leu Ser Ser Gln Leu
            420                 425                 430

Leu Glu Leu Arg Glu Ile Pro Phe
            435                 440

<210> SEQ ID NO 162
<211> LENGTH: 397
<212> TYPE: PRT
<213> ORGANISM: Torulaspora delbrueckii

<400> SEQUENCE: 162

Met Leu Tyr Leu Phe Ser Leu Cys Val Leu Ser Leu Ala Trp Cys
1               5                   10                  15

Tyr Glu Asp Arg Ala Thr Asp Asp Leu Asp Arg Leu Trp Gly Gln Asp
            20                  25                  30

Trp Pro Phe Ser Gly Ile Asn Thr Tyr Ala His Leu Pro His Gln Lys
        35                  40                  45

Cys Leu Leu Asp Lys Asn Phe Thr Phe Asp Ile Gly Ile Ile Gly Val
50                  55                  60

Pro Phe Asp Ser Ala Val Thr Tyr Arg Pro Gly Ala Arg Phe Gly Pro
65                  70                  75                  80

Gln Ala Ile Arg Ala Ala Ser Gln Arg Gln Ile Pro Ile Arg Ser Phe
            85                  90                  95

Asn Phe Arg Ala Gly Ile Asn Pro Tyr Gln Lys Trp Ala Lys Val Val
            100                 105                 110

Asp Cys Gly Asp Ile Pro Val Thr Pro Met Asp Ser Ser Leu Ala Leu
        115                 120                 125

Glu Met Met Thr Ala Ala Tyr Glu Asn Leu Leu Asp Arg Asp Ser Glu
130                 135                 140

Tyr Ser Lys Ser Ser Met Pro Pro Arg Leu Leu Ser Leu Gly Gly Asp
145                 150                 155                 160

His Ser Ile Ile Leu Pro Val Ile Arg Asn Leu Tyr Lys Leu Tyr Gly
            165                 170                 175

Pro Ile Thr Val Leu His Phe Asp Ser His Leu Asp Thr Trp Ser Pro
        180                 185                 190

Ser Lys Tyr Pro Ser Tyr Trp His Ser Lys Ser Ser Lys Phe Thr His
    195                 200                 205

Gly Ser Met Leu Trp Met Ala Lys Gln Glu Gly Leu Leu Ser Glu His
    210                 215                 220

Asn Val His Ala Gly Leu Arg Thr Arg Leu Ser Gly Val Asp Trp Glu
225                 230                 235                 240

Asp Tyr Glu Asp Asp Asp Asp Val Gly Phe His Arg Ile Glu Ser Asp
            245                 250                 255

```
Asp Ile Ile Arg Leu Gly Val Gln Gly Leu Ala Glu Lys Ile Lys Gln
            260                 265                 270

Leu Leu Pro Lys Lys Gln Pro Leu Tyr Ile Ser Val Asp Ile Asp Val
        275                 280                 285

Leu Asp Pro Ser Ala Ala Pro Gly Thr Gly Thr Val Glu Ala Gly Gly
290                 295                 300

Trp Leu Thr Arg Glu Leu Ile Tyr Leu Leu Arg Ser Leu Glu Asp Tyr
305                 310                 315                 320

Pro Ile Val Gly Ala Asp Val Glu Val Ser Pro Pro Phe Asp Gln
                325                 330                 335

Ser Glu Ile Thr Ala Ile Ala Ser Gln Ile Ala Tyr Glu Leu Leu
            340                 345                 350

Thr Ser Met Val Lys Ser Gly Pro Ile Glu Pro Gln Met Ile Gln Glu
        355                 360                 365

Asn Gly Leu Phe Asn Leu Arg Ala Leu Gln Asp Asn His Val Asp Phe
    370                 375                 380

Ser Ala Ala Lys Pro Asp Thr Asp Tyr Asp Lys Leu Leu
385                 390                 395

<210> SEQ ID NO 163
<211> LENGTH: 278
<212> TYPE: PRT
<213> ORGANISM: Lachancea kluyveri

<400> SEQUENCE: 163

Met Arg Gly Phe Asn Phe Arg Ala Gly Ile Asn Pro Tyr Gln Ser Trp
1               5                   10                  15

Ala Lys Val Met Asp Cys Gly Asp Ile Pro Val Thr Pro Met Asp Asn
            20                  25                  30

Gln Leu Ala Leu Lys Met Met Asp Ala Ala Tyr Glu Asn Leu Leu Asp
        35                  40                  45

Arg Asn Ser Thr Ala Ala Glu Ser Pro Leu Pro Pro Arg Phe Ala Ser
    50                  55                  60

Leu Gly Gly Asp His Ser Val Ile Leu Pro Ile Leu Arg Gln Leu His
65                  70                  75                  80

Lys Ile Tyr Gly Pro Ile Ser Val Ile His Phe Asp Ser His Leu Asp
                85                  90                  95

Thr Trp Ala Pro Ser Lys Tyr Pro Ser Tyr Trp His Ser Asp Thr Ser
            100                 105                 110

Glu Phe Thr His Gly Ser Met Leu Trp Ile Ala Lys Gln Glu Gly Leu
        115                 120                 125

Leu Ala Glu Asn Ser Asn Val His Ala Gly Leu Arg Thr Arg Leu Ser
    130                 135                 140

Gly Val Gly Trp Asp Asp Tyr Glu Glu Asp Ser Glu Thr Gly Phe His
145                 150                 155                 160

Arg Ile Glu Cys Asp Glu Ile Leu Lys Val Gly Val Asn Gly Ile Ala
                165                 170                 175

Glu Arg Ile Leu Glu His Val Pro Lys Asp Lys Pro Val Tyr Ile Ser
            180                 185                 190

Val Asp Ile Asp Val Leu Asp Pro Ser Ala Ala Pro Gly Thr Gly Thr
        195                 200                 205

Ile Glu Val Gly Gly Leu Leu Thr Arg Glu Leu Ile Ser Ile Ile Arg
    210                 215                 220

Gln Leu Glu Asp Leu His Leu Val Gly Ala Asp Val Val Glu Val Ser
```

225                 230                 235                 240

Pro Ala Tyr Asp His Ala Asp Ile Thr Ser Thr Ala Ala Ser Gln Ile
                245                 250                 255

Val Tyr Glu Leu Ile Thr Asn Met Val Lys Lys Gly Pro Val Asp Pro
                260                 265                 270

Ala Ile Val Glu Ala Asn
        275

<210> SEQ ID NO 164
<211> LENGTH: 52
<212> TYPE: PRT
<213> ORGANISM: Artificial Sequence
<220> FEATURE:
<223> OTHER INFORMATION: conserved domain within concensus
<220> FEATURE:
<221> NAME/KEY: VARIANT
<222> LOCATION: (4)..(4)
<223> OTHER INFORMATION: may be N or I
<220> FEATURE:
<221> NAME/KEY: VARIANT
<222> LOCATION: (5)..(5)
<223> OTHER INFORMATION: may be G or P
<220> FEATURE:
<221> NAME/KEY: VARIANT
<222> LOCATION: (6)..(6)
<223> OTHER INFORMATION: may be M or I
<220> FEATURE:
<221> NAME/KEY: VARIANT
<222> LOCATION: (8)..(8)
<223> OTHER INFORMATION: may be S
<220> FEATURE:
<221> NAME/KEY: VARIANT
<222> LOCATION: (9)..(9)
<223> OTHER INFORMATION: may be Y
<220> FEATURE:
<221> NAME/KEY: VARIANT
<222> LOCATION: (11)..(11)
<223> OTHER INFORMATION: may be Q or A
<220> FEATURE:
<221> NAME/KEY: VARIANT
<222> LOCATION: (14)..(14)
<223> OTHER INFORMATION: may be N. D or F
<220> FEATURE:
<221> NAME/KEY: VARIANT
<222> LOCATION: (15)..(15)
<223> OTHER INFORMATION: may be F
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: VARIANT
<222> LOCATION: (20)..(20)
<223> OTHER INFORMATION: may be D, N or R
<220> FEATURE:
<221> NAME/KEY: VARIANT
<222> LOCATION: (23)..(23)
<223> OTHER INFORMATION: may be S, H or R
<220> FEATURE:
<221> NAME/KEY: VARIANT
<222> LOCATION: (24)..(24)
<223> OTHER INFORMATION: may be I
<220> FEATURE:
<221> NAME/KEY: VARIANT
<222> LOCATION: (25)..(25)
<223> OTHER INFORMATION: may be I, L or M
<220> FEATURE:
<221> NAME/KEY: VARIANT
<222> LOCATION: (30)..(30)
<223> OTHER INFORMATION: may beV or L
<220> FEATURE:
<221> NAME/KEY: VARIANT
<222> LOCATION: (32)..(32)
<223> OTHER INFORMATION: may be I
<220> FEATURE:

```
<221> NAME/KEY: VARIANT
<222> LOCATION: (35)..(35)
<223> OTHER INFORMATION: may be V
<220> FEATURE:
<221> NAME/KEY: VARIANT
<222> LOCATION: (37)..(37)
<223> OTHER INFORMATION: may be S
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: VARIANT
<222> LOCATION: (39)..(39)
<223> OTHER INFORMATION: may be I
<220> FEATURE:
<221> NAME/KEY: VARIANT
<222> LOCATION: (41)..(41)
<223> OTHER INFORMATION: may be F
<220> FEATURE:
<221> NAME/KEY: VARIANT
<222> LOCATION: (42)..(42)
<223> OTHER INFORMATION: may be E, Q or T
<220> FEATURE:
<221> NAME/KEY: VARIANT
<222> LOCATION: (43)..(43)
<223> OTHER INFORMATION: may be Q
<220> FEATURE:
<221> NAME/KEY: VARIANT
<222> LOCATION: (45)..(45)
<223> OTHER INFORMATION: may be D, G or N
<220> FEATURE:
<221> NAME/KEY: VARIANT
<222> LOCATION: (46)..(46)
<223> OTHER INFORMATION: may be K or L
<220> FEATURE:
<221> NAME/KEY: VARIANT
<222> LOCATION: (47)..(47)
<223> OTHER INFORMATION: may be G
<220> FEATURE:
<221> NAME/KEY: VARIANT
<222> LOCATION: (48)..(48)
<223> OTHER INFORMATION: may be F
<220> FEATURE:
<221> NAME/KEY: VARIANT
<222> LOCATION: (49)..(49)
<223> OTHER INFORMATION: may be D or H
<220> FEATURE:
<221> NAME/KEY: VARIANT
<222> LOCATION: (50)..(50)
<223> OTHER INFORMATION: may be E
<220> FEATURE:
<221> NAME/KEY: VARIANT
<222> LOCATION: (52)..(52)
<223> OTHER INFORMATION: may be I or V

<400> SEQUENCE: 164

Gln Arg Gln Thr Ser Leu Arg Gly Phe Asn Phe Arg Ala Gly Ile Asn
1               5                   10                  15

Pro Tyr Xaa Ser Trp Ala Lys Val Val Asp Cys Gly Cys Ile Pro Val
            20                  25                  30

Thr Pro Met Asp Asn Xaa Leu Ala Leu Lys Met Met Thr Ala Ala Tyr
        35                  40                  45

Glu Asn Leu Leu
    50

<210> SEQ ID NO 165
<211> LENGTH: 21
<212> TYPE: PRT
<213> ORGANISM: Artificial Sequence
<220> FEATURE:
<223> OTHER INFORMATION: conserved domain within consensus
<220> FEATURE:
<221> NAME/KEY: VARIANT
```

```
<222> LOCATION: (3)..(3)
<223> OTHER INFORMATION: May be S
<220> FEATURE:
<221> NAME/KEY: VARIANT
<222> LOCATION: (5)..(5)
<223> OTHER INFORMATION: May be D
<220> FEATURE:
<221> NAME/KEY: VARIANT
<222> LOCATION: (6)..(6)
<223> OTHER INFORMATION: May be S
<220> FEATURE:
<221> NAME/KEY: VARIANT
<222> LOCATION: (10)..(10)
<223> OTHER INFORMATION: May be Y
<220> FEATURE:
<221> NAME/KEY: VARIANT
<222> LOCATION: (14)..(14)
<223> OTHER INFORMATION: May be N, A or K
<220> FEATURE:
<221> NAME/KEY: VARIANT
<222> LOCATION: (15)..(15)
<223> OTHER INFORMATION: May be N, Q or G
<220> FEATURE:
<221> NAME/KEY: VARIANT
<222> LOCATION: (17)..(17)
<223> OTHER INFORMATION: May be D or K
<220> FEATURE:
<221> NAME/KEY: VARIANT
<222> LOCATION: (18)..(18)
<223> OTHER INFORMATION: May be I or V
<220> FEATURE:
<221> NAME/KEY: VARIANT
<222> LOCATION: (19)..(19)
<223> OTHER INFORMATION: May be N

<400> SEQUENCE: 165

Thr Trp Ala Pro Ser Lys Tyr Pro Ser Phe Trp His Ser Asp Thr Ser
1               5                   10                  15

Glu Phe Thr His Gly
            20

<210> SEQ ID NO 166
<211> LENGTH: 306
<212> TYPE: PRT
<213> ORGANISM: Escherichia coli

<400> SEQUENCE: 166

Met Ser Thr Leu Gly His Gln Tyr Asp Asn Ser Leu Val Ser Asn Ala
1               5                   10                  15

Phe Gly Phe Leu Arg Leu Pro Met Asn Phe Gln Pro Tyr Asp Ser Asp
                20                  25                  30

Ala Asp Trp Val Ile Thr Gly Val Pro Phe Asp Met Ala Thr Ser Gly
            35                  40                  45

Arg Ala Gly Gly Arg His Gly Pro Ala Ala Ile Arg Gln Val Ser Thr
        50                  55                  60

Asn Leu Ala Trp Glu His Asn Arg Phe Pro Trp Asn Phe Asp Met Arg
65              70                  75                  80

Glu Arg Leu Asn Val Val Asp Cys Gly Asp Leu Val Tyr Ala Phe Gly
                85                  90                  95

Asp Ala Arg Glu Met Ser Glu Lys Leu Gln Ala His Ala Glu Lys Leu
            100                 105                 110

Leu Ala Gly Lys Arg Met Leu Ser Phe Gly Asp His Phe Val
        115                 120                 125

Thr Leu Pro Leu Leu Arg Ala His Ala Lys His Phe Gly Lys Met Ala
    130                 135                 140

Leu Val His Phe Asp Ala His Thr Asp Thr Tyr Ala Asn Gly Cys Glu
```

```
            145                 150                 155                 160
        Phe Asp His Gly Thr Met Phe Tyr Thr Ala Pro Lys Glu Gly Leu Ile
                        165                 170                 175
        Asp Pro Asn His Ser Val Gln Ile Gly Ile Arg Thr Glu Phe Asp Lys
                        180                 185                 190
        Asp Asn Gly Phe Thr Val Leu Asp Ala Cys Gln Val Asn Asp Arg Ser
                        195                 200                 205
        Val Asp Asp Val Ile Ala Gln Val Lys Gln Ile Val Gly Asp Met Pro
                        210                 215                 220
        Val Tyr Leu Thr Phe Asp Ile Asp Cys Leu Asp Pro Ala Phe Ala Pro
        225                 230                 235                 240
        Gly Thr Gly Thr Pro Val Ile Gly Gly Leu Thr Ser Asp Arg Ala Ile
                        245                 250                 255
        Lys Leu Val Arg Gly Leu Lys Asp Leu Asn Ile Val Gly Met Asp Val
                        260                 265                 270
        Val Glu Val Ala Pro Ala Tyr Asp Gln Ser Glu Ile Thr Ala Leu Ala
                        275                 280                 285
        Ala Ala Thr Leu Ala Leu Glu Met Leu Tyr Ile Gln Ala Ala Lys Lys
                        290                 295                 300
        Gly Glu
        305

<210> SEQ ID NO 167
<211> LENGTH: 306
<212> TYPE: PRT
<213> ORGANISM: Shigella flexneri

<400> SEQUENCE: 167

Met Ser Thr Leu Gly His Gln Tyr Asp Asn Ser Leu Val Ser Asn Ala
        1               5                   10                  15
        Phe Gly Phe Leu Arg Leu Pro Met Asn Phe Gln Pro Tyr Asp Ser Asp
                        20                  25                  30
        Ala Asp Trp Val Ile Thr Gly Val Pro Phe Asp Met Ala Thr Ser Gly
                        35                  40                  45
        Arg Ala Gly Gly Arg His Gly Pro Ala Ala Ile Arg Gln Val Ser Thr
        50                  55                  60
        Asn Leu Ala Trp Glu His Asn Arg Phe Pro Trp Asn Phe Asp Met Arg
        65                  70                  75                  80
        Glu Arg Leu Asn Val Val Asp Cys Gly Asp Leu Val Tyr Ala Phe Gly
                        85                  90                  95
        Asp Ala Arg Glu Met Ser Glu Lys Leu Gln Ala His Ala Glu Lys Leu
                        100                 105                 110
        Leu Ala Ser Gly Lys Arg Met Leu Ser Phe Gly Gly Asp His Phe Val
                        115                 120                 125
        Thr Leu Pro Leu Leu Arg Ala His Ala Lys His Phe Gly Lys Met Ala
        130                 135                 140
        Leu Val His Phe Asp Ala His Thr Asp Thr Tyr Ala Asn Gly Cys Glu
        145                 150                 155                 160
        Phe Asp His Gly Thr Met Phe Tyr Thr Ala Pro Lys Glu Gly Leu Ile
                        165                 170                 175
        Asp Pro Asn His Ser Val Gln Ile Gly Ile Arg Thr Glu Phe Asp Lys
                        180                 185                 190
        Asp Asn Gly Phe Thr Val Leu Asp Ala Cys Gln Val Asn Asp Arg Ser
                        195                 200                 205
```

```
Val Asp Asp Val Ile Ala Gln Val Lys Gln Ile Val Gly Asp Met Pro
    210                 215                 220

Val Tyr Leu Thr Phe Asp Ile Asp Cys Leu Asp Pro Ala Phe Ala Pro
225                 230                 235                 240

Gly Thr Gly Thr Pro Val Ile Gly Gly Leu Thr Ser Asp Arg Ala Ile
                245                 250                 255

Lys Leu Val Arg Gly Leu Lys Asp Leu Asn Ile Val Gly Met Asp Val
            260                 265                 270

Val Glu Val Ala Pro Ala Tyr Asp Gln Ser Glu Ile Thr Ala Leu Ala
        275                 280                 285

Ala Ala Thr Leu Ala Leu Glu Met Leu Tyr Ile Gln Ala Ala Lys Lys
    290                 295                 300

Gly Glu
305

<210> SEQ ID NO 168
<211> LENGTH: 306
<212> TYPE: PRT
<213> ORGANISM: Klebsiella oxytoca

<400> SEQUENCE: 168

Met Ser Thr Leu Gly His Gln Tyr Asp Asn Ser Leu Val Ser Asn Ala
1               5                   10                  15

Phe Gly Phe Leu Arg Leu Pro Met Asn Phe Pro Tyr Asp Ser Asp
            20                  25                  30

Ala Asp Trp Val Ile Thr Gly Val Pro Phe Asp Met Ala Thr Ser Gly
        35                  40                  45

Arg Ala Gly Gly Arg His Gly Pro Ala Ala Ile Arg Gln Val Ser Thr
    50                  55                  60

Asn Leu Ala Trp Glu His Asn Arg Phe Pro Trp Asn Phe Asp Met Arg
65                  70                  75                  80

Glu Arg Leu Asn Val Val Asp Cys Gly Asp Leu Val Tyr Ala Phe Gly
                85                  90                  95

Asp Ala Arg Glu Met Ser Glu Lys Leu Gln Ala His Ala Glu Lys Leu
            100                 105                 110

Leu Ala Ala Gly Lys Arg Met Leu Ser Phe Gly Gly Asp His Phe Val
        115                 120                 125

Thr Leu Pro Leu Leu Arg Ala His Ala Lys His Phe Gly Lys Met Ala
    130                 135                 140

Leu Val His Phe Asp Ala His Thr Asp Thr Tyr Ala Asn Gly Cys Glu
145                 150                 155                 160

Phe Asp His Gly Thr Met Phe Tyr Thr Ala Pro Asn Glu Gly Leu Ile
                165                 170                 175

Asp Pro Asn His Ser Val Gln Ile Gly Ile Arg Thr Glu Phe Asp Lys
            180                 185                 190

Asp Asn Gly Phe Thr Val Leu Asp Ala Gly Gln Val Asn Asp Arg Ser
        195                 200                 205

Val Asp Asp Val Ile Ala Gln Val Lys Gln Ile Val Gly Asp Met Pro
    210                 215                 220

Val Tyr Leu Thr Phe Asp Ile Asp Cys Leu Asp Pro Ala Phe Ala Pro
225                 230                 235                 240

Gly Thr Gly Thr Pro Val Ile Gly Gly Leu Thr Ser Asp Arg Ala Ile
                245                 250                 255

Lys Leu Val Arg Gly Leu Lys Asp Leu Asn Ile Val Gly Met Asp Val
            260                 265                 270
```

Val Glu Val Ala Pro Ala Tyr Asp Gln Ser Glu Ile Thr Ala Leu Ala
            275                 280                 285

Ala Ala Thr Leu Ala Leu Glu Met Leu Tyr Ile Gln Ala Ala Lys Lys
            290                 295                 300

Gly Glu
305

<210> SEQ ID NO 169
<211> LENGTH: 306
<212> TYPE: PRT
<213> ORGANISM: Klebsiella pneumoniae

<400> SEQUENCE: 169

Met Ser Thr Leu Gly His Gln Tyr Asp Asn Ser Leu Val Ser Asn Ala
1               5                   10                  15

Phe Gly Phe Leu Arg Leu Pro Met Asn Phe Met Pro Tyr Glu Ser Asp
                20                  25                  30

Ala Asp Trp Val Ile Thr Gly Val Pro Phe Asp Met Ala Thr Ser Gly
            35                  40                  45

Arg Ala Gly Gly Arg His Gly Pro Ala Ala Ile Arg Gln Val Ser Thr
        50                  55                  60

Asn Leu Ala Trp Glu His Asn Arg Phe Pro Trp Asn Phe Asp Met Arg
65                  70                  75                  80

Glu Arg Leu Asn Val Val Asp Cys Gly Asp Leu Val Tyr Ala Phe Gly
                85                  90                  95

Asp Ala Arg Glu Met Ser Glu Lys Leu Gln Ala His Ala Glu Lys Leu
            100                 105                 110

Leu Ala Ala Gly Lys Arg Met Leu Ser Phe Gly Gly Asp His Phe Val
        115                 120                 125

Thr Leu Pro Leu Leu Arg Ala His Ala Lys His Phe Gly Lys Met Ala
130                 135                 140

Leu Val His Phe Asp Ala His Thr Asp Thr Tyr Ala Asn Gly Cys Glu
145                 150                 155                 160

Phe Asp His Gly Thr Met Phe Tyr Thr Ala Pro Asn Glu Gly Leu Ile
                165                 170                 175

Asp Pro Asn His Ser Val Gln Ile Gly Ile Arg Thr Glu Phe Asp Lys
            180                 185                 190

Asp Asn Gly Phe Thr Val Leu Asp Ala Gly Gln Val Asn Asp Arg Ser
        195                 200                 205

Val Asp Asp Val Ile Ala Gln Val Lys Gln Ile Val Gly Asp Met Pro
    210                 215                 220

Val Tyr Leu Thr Phe Asp Ile Asp Cys Leu Asp Pro Ala Phe Ala Pro
225                 230                 235                 240

Gly Thr Gly Thr Pro Val Ile Gly Gly Leu Thr Ser Asp Arg Ala Ile
                245                 250                 255

Lys Leu Val Arg Gly Leu Lys Asp Leu Asn Ile Val Gly Met Asp Val
            260                 265                 270

Val Glu Val Ala Pro Ala Tyr Asp Gln Ser Glu Ile Thr Ala Leu Ala
        275                 280                 285

Ala Ala Thr Leu Ala Leu Glu Met Leu Tyr Ile Gln Ala Ala Lys Lys
            290                 295                 300

Gly Glu
305

<210> SEQ ID NO 170
<211> LENGTH: 306
<212> TYPE: PRT
<213> ORGANISM: Enterobacter cloacae

<400> SEQUENCE: 170

Met Ser Thr Leu Gly His Gln Tyr Asp Asn Ser Leu Val Ser Asn Ala
1               5                   10                  15

Phe Gly Phe Leu Arg Leu Pro Met Asn Phe Gln Pro Tyr Asp Ser Asp
            20                  25                  30

Ala Asp Trp Val Ile Thr Gly Val Pro Phe Asp Met Ala Thr Ser Gly
        35                  40                  45

Arg Ala Gly Gly Arg His Gly Pro Ala Ala Ile Arg Gln Val Ser Thr
    50                  55                  60

Asn Leu Ala Trp Glu His Asn Arg Phe Pro Trp Asn Phe Asp Met Arg
65                  70                  75                  80

Glu Arg Leu Asn Val Val Asp Cys Gly Asp Leu Val Tyr Ala Phe Gly
                85                  90                  95

Asp Ala Arg Glu Met Ser Glu Lys Leu Gln Ala His Ala Glu Lys Leu
            100                 105                 110

Leu Ala Ala Gly Lys Arg Met Leu Ser Phe Gly Gly Asp His Phe Val
        115                 120                 125

Thr Leu Pro Leu Leu Arg Ala His Ala Lys His Phe Gly Lys Met Ala
    130                 135                 140

Leu Val His Phe Asp Ala His Thr Asp Thr Tyr Ala Asn Gly Cys Glu
145                 150                 155                 160

Phe Asp His Gly Thr Met Phe Tyr Thr Ala Pro Asn Glu Gly Leu Ile
                165                 170                 175

Asp Pro Asn His Ser Val Gln Ile Gly Ile Arg Thr Glu Phe Asp Lys
            180                 185                 190

Asp Asn Gly Phe Thr Val Leu Asp Ala Cys Gln Val Asn Asp Arg Gly
        195                 200                 205

Val Asp Asp Ile Ile Ala Gln Val Lys Gln Ile Val Gly Asp Met Pro
    210                 215                 220

Val Tyr Leu Thr Phe Asp Ile Asp Cys Leu Asp Pro Ala Phe Ala Pro
225                 230                 235                 240

Gly Thr Gly Thr Pro Val Ile Gly Gly Leu Thr Ser Asp Arg Ala Ile
                245                 250                 255

Lys Leu Val Arg Gly Leu Lys Asp Leu Asn Ile Val Gly Met Asp Val
            260                 265                 270

Val Glu Val Ala Pro Ala Tyr Asp Gln Ser Glu Ile Thr Ala Leu Ala
        275                 280                 285

Ala Ala Thr Leu Ala Leu Glu Met Leu Tyr Ile Gln Ala Ala Lys Lys
    290                 295                 300

Gly Glu
305

<210> SEQ ID NO 171
<211> LENGTH: 306
<212> TYPE: PRT
<213> ORGANISM: Citrobacter koseri

<400> SEQUENCE: 171

Met Ser Thr Leu Gly His Gln Tyr Asp Asn Ser Leu Val Ser Asn Ala
1               5                   10                  15

Phe Gly Phe Leu Arg Leu Pro Leu Asn Phe Gln Pro Tyr Asp Ser Asp

```
                 20                  25                  30
Ala Asp Trp Val Ile Thr Gly Val Pro Phe Asp Met Ala Thr Ser Gly
             35                  40                  45

Arg Ala Gly Gly Arg His Gly Pro Ala Ala Ile Arg Gln Val Ser Thr
         50                  55                  60

Asn Leu Ala Trp Glu His Asn Arg Phe Pro Trp Asn Phe Asp Met Arg
 65                  70                  75                  80

Glu Arg Leu Asn Val Val Asp Cys Gly Asp Leu Val Tyr Ala Phe Gly
                 85                  90                  95

Asp Ala Arg Glu Met Ser Glu Lys Leu Gln Ala His Ala Glu Lys Leu
            100                 105                 110

Leu Ser Ala Gly Lys Arg Met Leu Ser Phe Gly Gly Asp His Phe Val
        115                 120                 125

Thr Leu Pro Leu Leu Arg Ala His Ala Lys His Phe Gly Lys Met Ala
    130                 135                 140

Leu Val His Phe Asp Ala His Thr Asp Thr Tyr Ala Asn Gly Cys Glu
145                 150                 155                 160

Phe Asp His Gly Thr Met Phe Tyr Thr Ala Pro Lys Glu Gly Leu Ile
                165                 170                 175

Asp Pro Asn His Ser Val Gln Ile Gly Ile Arg Thr Glu Phe Asp Lys
            180                 185                 190

Asp Asn Gly Phe Thr Val Leu Asp Ala Cys Gln Val Asn Asp Arg Gly
        195                 200                 205

Val Asp Asp Ile Ile Ala Gln Val Asn Gln Ile Val Gly Asp Met Pro
    210                 215                 220

Val Tyr Leu Thr Phe Asp Ile Asp Cys Leu Asp Pro Ala Phe Ala Pro
225                 230                 235                 240

Gly Thr Gly Thr Pro Val Ile Gly Gly Leu Thr Ser Asp Arg Ala Ile
                245                 250                 255

Lys Leu Val Arg Gly Leu Lys Asp Leu Asn Ile Val Gly Met Asp Val
            260                 265                 270

Val Glu Val Ala Pro Ala Tyr Asp Gln Ser Glu Ile Thr Ala Leu Ala
        275                 280                 285

Ala Ala Thr Leu Ala Leu Glu Met Leu Tyr Ile Gln Ala Ala Lys Lys
    290                 295                 300

Gly Glu
305

<210> SEQ ID NO 172
<211> LENGTH: 302
<212> TYPE: PRT
<213> ORGANISM: Ceratitis capitata

<400> SEQUENCE: 172

Met Ser Thr Leu Gly His Gln Tyr Asp Asn Ser Leu Val Ser Asn Ala
 1               5                  10                  15

Phe Gly Phe Leu Arg Leu Pro Leu Asn Phe Gln Pro Tyr Asp Ser Asp
                 20                  25                  30

Ala Asp Trp Val Ile Thr Gly Val Pro Phe Asp Met Ala Thr Ser Gly
             35                  40                  45

Arg Ala Gly Gly Arg His Gly Pro Ala Ala Ile Arg Gln Val Ser Thr
         50                  55                  60

Asn Leu Ala Trp Glu His Tyr Arg Phe Pro Trp Asn Phe Asp Met Arg
 65                  70                  75                  80
```

```
Glu Arg Leu Asn Val Val Asp Cys Gly Asp Leu Val Tyr Ala Phe Gly
             85                  90                  95

Asp Ala Arg Glu Met Ser Glu Lys Leu Gln Ala His Ala Glu Arg Leu
            100                 105                 110

Leu Ala Ala Gly Lys Arg Met Leu Ser Phe Gly Gly Asp His Phe Val
            115                 120                 125

Thr Leu Pro Leu Leu Arg Ala His Ala Lys His Phe Gly Lys Met Ala
            130                 135                 140

Leu Val His Phe Asp Ala His Thr Asp Thr Tyr Ala Asn Gly Cys Glu
145                 150                 155                 160

Phe Asp His Gly Thr Met Phe Tyr Thr Ala Pro Lys Glu Gly Leu Ile
                165                 170                 175

Asp Pro Asn His Ser Val Gln Ile Gly Ile Arg Thr Glu Phe Asp Lys
            180                 185                 190

Asp Asn Gly Phe Thr Val Leu Asp Ala Cys Gln Val Asn Asp Arg Gly
            195                 200                 205

Val Asp Asp Ile Ile Ala Gln Val Lys Gln Ile Val Gly Asp Met Pro
210                 215                 220

Val Tyr Leu Thr Phe Asp Ile Asp Cys Leu Asp Pro Ala Phe Ala Pro
225                 230                 235                 240

Gly Thr Gly Thr Pro Val Ile Gly Gly Leu Thr Ser Asp Arg Ala Ile
                245                 250                 255

Lys Leu Val Arg Gly Leu Lys Asp Leu Asn Ile Val Gly Met Asp Val
            260                 265                 270

Val Glu Val Ala Pro Ala Tyr Asp Thr Ala Leu Ala Ala Ala Thr Leu
            275                 280                 285

Ala Leu Glu Met Leu Tyr Ile Gln Ala Ala Lys Lys Gly Glu
            290                 295                 300

<210> SEQ ID NO 173
<211> LENGTH: 306
<212> TYPE: PRT
<213> ORGANISM: Salmonella enterica

<400> SEQUENCE: 173

Met Ser Thr Leu Gly His Gln Tyr Asp Asn Ser Leu Val Ser Asn Ala
1               5                   10                  15

Phe Gly Phe Leu Arg Leu Pro Met Asn Phe Gln Pro Tyr Asp Ser Asp
            20                  25                  30

Ala Asp Trp Val Ile Thr Gly Val Pro Phe Asp Met Ala Thr Ser Gly
            35                  40                  45

Arg Ala Gly Gly Arg His Gly Pro Ala Ala Ile Arg Gln Val Ser Thr
     50                  55                  60

Asn Leu Ala Trp Glu His Arg Phe Pro Trp Asn Phe Asp Met Arg
65                  70                  75                  80

Glu Arg Leu Asn Val Val Asp Cys Gly Asp Leu Val Tyr Ala Phe Gly
             85                  90                  95

Asp Ala Arg Glu Met Ser Glu Lys Leu Gln Ala His Ala Glu Lys Leu
            100                 105                 110

Leu Ser Ala Gly Lys Arg Met Leu Ser Phe Gly Gly Asp His Phe Val
            115                 120                 125

Thr Leu Pro Leu Leu Arg Ala His Ala Lys His Phe Gly Lys Met Ala
            130                 135                 140

Leu Val His Phe Asp Ala His Thr Asp Thr Tyr Ala Asn Gly Cys Glu
145                 150                 155                 160
```

```
Phe Asp His Gly Thr Met Phe Tyr Thr Ala Pro Lys Glu Gly Leu Ile
                165                 170                 175
Asp Pro His His Ser Val Gln Ile Gly Ile Arg Thr Glu Phe Asp Lys
            180                 185                 190
Asp Asn Gly Phe Thr Val Leu Asp Ala Cys Gln Val Asn Asp Arg Gly
        195                 200                 205
Val Asp Asp Ile Leu Ala Gln Val Lys Gln Ile Val Gly Asp Met Pro
    210                 215                 220
Val Tyr Leu Thr Phe Asp Ile Asp Cys Leu Asp Pro Ala Phe Ala Pro
225                 230                 235                 240
Gly Thr Gly Thr Pro Val Ile Gly Gly Leu Thr Ser Asp Arg Ala Ile
                245                 250                 255
Lys Leu Val Arg Gly Leu Lys Asp Leu Asn Ile Val Gly Met Asp Val
                260                 265                 270
Val Glu Val Ala Pro Ala Tyr Asp Gln Ser Glu Ile Thr Ala Leu Ala
            275                 280                 285
Ala Ala Thr Leu Ala Leu Glu Met Leu Tyr Ile Gln Ser Ala Lys Lys
        290                 295                 300
Gly Glu
305

<210> SEQ ID NO 174
<211> LENGTH: 320
<212> TYPE: PRT
<213> ORGANISM: Burkholderia pseudomallei

<400> SEQUENCE: 174

Met Asn Glu Thr Leu Tyr Gly Asp Gly Ala Ile Arg Arg Pro Ser Ile
1               5                   10                  15
Tyr Gly Ser Ser Val Glu Asn Thr Tyr Ala Gly Val Leu Ser Phe Met
                20                  25                  30
Arg Arg Asn Tyr Thr Arg Asp Leu Gly Gly Val Asp Val Ala Val Cys
            35                  40                  45
Gly Val Pro Leu Asp Leu Ala Thr Thr Phe Arg Ser Gly Ala Arg Leu
        50                  55                  60
Gly Pro Ala Ala Val Arg Ala Ala Ser Val Gln Leu Ala Glu Leu Arg
65                  70                  75                  80
Pro Tyr Pro Trp Gly Phe Asp Pro Phe Asp Leu Ala Val Ile Asp
                85                  90                  95
Tyr Gly Asp Cys Trp Phe Asp Ala His Asn Pro Leu Ser Ile Lys Pro
                100                 105                 110
Ala Ile Val Glu His Ala Arg Thr Ile Leu Gln Ser Gly Ala Ala Met
            115                 120                 125
Leu Thr Leu Gly Gly Asp His Tyr Ile Thr Tyr Pro Leu Leu Ile Ala
        130                 135                 140
His Ala Gln Arg His Gly Lys Pro Leu Ser Leu Ile His Phe Asp Ala
145                 150                 155                 160
His Cys Asp Thr Trp Ala Asp Asp Ala Pro Asp Ser Leu Asn His Gly
                165                 170                 175
Thr Met Phe Tyr Lys Ala Val Asn Glu Gly Leu Ile Asp Pro Lys Thr
                180                 185                 190
Ser Val Gln Val Gly Ile Arg Thr Trp Asn Asp Asp Tyr Leu Gly Ile
            195                 200                 205
```

His Val Leu Asp Ala Ala Trp Val His Glu His Gly Pro Arg Ala Thr
210                 215                 220

Ala Glu Arg Ile Ala Ser Ile Val Gly Gly Arg Pro Ala Tyr Leu Thr
225                 230                 235                 240

Phe Asp Ile Asp Cys Leu Asp Pro Ala Phe Ala Pro Gly Thr Gly Thr
            245                 250                 255

Pro Val Ala Gly Gly Leu Ser Ser Ala Gln Ala Leu Ala Ile Val Arg
        260                 265                 270

Gly Leu Gly Gly Val Asn Leu Ile Gly Ala Asp Val Glu Val Ala
        275                 280                 285

Pro Ala Tyr Asp Gln Ser Glu Ile Thr Ala Ile Ala Ala His Val
290                 295                 300

Ala Cys Asp Leu Leu Cys Leu Trp Arg Gln Arg Lys Thr Gly Ala Arg
305                 310                 315                 320

<210> SEQ ID NO 175
<211> LENGTH: 27
<212> TYPE: PRT
<213> ORGANISM: Artificial Sequence
<220> FEATURE:
<223> OTHER INFORMATION: conserved domain of consensus of bacterial
      guanidino-amide hydrolases
<220> FEATURE:
<221> NAME/KEY: VARIANT
<222> LOCATION: (7)..(7)
<223> OTHER INFORMATION: May be K
<220> FEATURE:
<221> NAME/KEY: VARIANT
<222> LOCATION: (9)..(9)
<223> OTHER INFORMATION: May be V
<220> FEATURE:
<221> NAME/KEY: VARIANT
<222> LOCATION: (10)..(10)
<223> OTHER INFORMATION: May be N
<220> FEATURE:
<221> NAME/KEY: VARIANT
<222> LOCATION: (17)..(17)
<223> OTHER INFORMATION: May be H or K
<220> FEATURE:
<221> NAME/KEY: VARIANT
<222> LOCATION: (18)..(18)
<223> OTHER INFORMATION: May be T
<220> FEATURE:
<221> NAME/KEY: VARIANT
<222> LOCATION: (22)..(22)
<223> OTHER INFORMATION: May be V
<220> FEATURE:
<221> NAME/KEY: VARIANT
<222> LOCATION: (27)..(27)
<223> OTHER INFORMATION: May be W

<400> SEQUENCE: 175

His Gly Thr Met Phe Tyr Thr Ala Pro Lys Glu Gly Leu Ile Asp Pro
1               5                   10                  15

Asn His Ser Val Gln Ile Gly Ile Arg Thr Glu
            20                  25

<210> SEQ ID NO 176
<211> LENGTH: 59
<212> TYPE: DNA
<213> ORGANISM: Artificial Sequence
<220> FEATURE:
<223> OTHER INFORMATION: I-HmuII Recognition sequence 3' from
      restriction site antisense strand
<220> FEATURE:
<221> NAME/KEY: misc_feature
<222> LOCATION: (25)..(59)
<223> OTHER INFORMATION: n is a, c, g, or t

<400> SEQUENCE: 176
agtaatgagc ctaacgctca acaannnnnn nnnnnnnnnn nnnnnnnnnn nnnnnnnn        59

<210> SEQ ID NO 177
<211> LENGTH: 306
<212> TYPE: PRT
<213> ORGANISM: Artificial Sequence
<220> FEATURE:
<223> OTHER INFORMATION: Synthetic construct consensus of bacterial
      guanidino-amide hydrolases

<400> SEQUENCE: 177

```
Met Ser Thr Leu Gly His Gln Tyr Asp Asn Ser Leu Val Ser Asn Ala
1               5                   10                  15

Phe Gly Phe Leu Arg Leu Pro Met Asn Phe Gln Pro Tyr Asp Ser Asp
            20                  25                  30

Ala Asp Trp Val Ile Thr Gly Val Pro Phe Asp Met Ala Thr Ser Gly
        35                  40                  45

Arg Ala Gly Gly Arg His Gly Pro Ala Ala Ile Arg Gln Val Ser Thr
    50                  55                  60

Asn Leu Ala Trp Glu His Asn Arg Phe Pro Trp Asn Phe Asp Met Arg
65                  70                  75                  80

Glu Arg Leu Asn Val Val Asp Cys Gly Asp Leu Val Tyr Ala Phe Gly
                85                  90                  95

Asp Ala Arg Glu Met Ser Glu Lys Leu Gln Ala His Ala Glu Lys Leu
            100                 105                 110

Leu Ala Ala Gly Lys Arg Met Leu Ser Phe Gly Gly Asp His Phe Val
        115                 120                 125

Thr Leu Pro Leu Leu Arg Ala His Ala Lys His Phe Gly Lys Met Ala
    130                 135                 140

Leu Val His Phe Asp Ala His Thr Asp Thr Tyr Ala Asn Gly Cys Glu
145                 150                 155                 160

Phe Asp His Gly Thr Met Phe Tyr Thr Ala Pro Lys Glu Gly Leu Ile
                165                 170                 175

Asp Pro Asn His Ser Val Gln Ile Gly Ile Arg Thr Glu Phe Asp Lys
            180                 185                 190

Asp Asn Gly Phe Thr Val Leu Asp Ala Cys Gln Val Asn Asp Arg Gly
        195                 200                 205

Val Asp Asp Val Ile Ala Gln Val Lys Gln Ile Val Gly Asp Met Pro
    210                 215                 220

Val Tyr Leu Thr Phe Asp Ile Asp Cys Leu Asp Pro Ala Phe Ala Pro
225                 230                 235                 240

Gly Thr Gly Thr Pro Val Ile Gly Gly Leu Thr Ser Asp Arg Ala Ile
                245                 250                 255

Lys Leu Val Arg Gly Leu Lys Asp Leu Asn Ile Val Gly Met Asp Val
            260                 265                 270

Val Glu Val Ala Pro Ala Tyr Asp Gln Ser Glu Ile Thr Ala Leu Ala
        275                 280                 285

Ala Ala Thr Leu Ala Leu Glu Met Leu Tyr Ile Gln Ala Ala Lys Lys
    290                 295                 300

Gly Glu
305
```

UREOHYDROLASES AS DOMINANT SELECTABLE MARKERS IN YEAST

FIELD

The invention relates to the fields of molecular biology and genetic engineering of microorganisms, especially of yeast.

INTRODUCTION

Arginine metabolism has been subject of intensive biochemical studies. After discovery of the urea cycle for use of arginine as a nitrogen source (Krebs and Henseleit, (1932) Wochenschrift 11: 757-759; Krebs, (1973) Biochemical Education 1: 19-23), attention focused on its role as a precursor for the synthesis of polyamine and the signaling compounds γ-aminobutyrate (GABA) and nitric oxide (Knowles and Moncada (1994) Biochem J 298: 249-258; Pitkanen et al., (2001) Biochem Biophys Res Commun 287: 1051-1057). The most widely distributed pathway for arginine degradation that occurs across all three kingdoms (Abdelal, (1979) Annu Rev Microbiol 33: 139-168) is initiated by arginase (EC 3.5.3.1), an ureohydrolase that converts arginine to ornithine and urea. Its active site, which contains several $Mn^{2+}$-binding sites, is also conserved in other ureohydrolases such as agmatinase (EC 3.5.3.11), formiminoglutamase (EC 3.5.3.8) and proclavaminate amidinohydrolase (EC 3.5.3.22), guanidinobutyrase (EC 3.5.3.7) and guanidinopropionase (EC 3. 5.3.17) (Ouzounis and Kyrpides, (1994) J Mol Evol 39: 101-104). Genes encoding these enzymes are assumed to have emerged early in evolution (Hartman, (1975) Orig Life 6: 423-427) and have been used as markers in phylogenetic studies (Ouzounis and Kyrpides (1994) J Mol Evol 39: 101-104; Sekowska et al., (2000) Microbiology 146: 1815-1828).

In eukaryotes, only two types of ureohydrolase have hitherto been described. In addition to arginase, higher eukaryotes express agmatinase (Coleman et al., (2004) Biochem J 379: 849-855), which participates in an alternative pathway for arginine catabolism (FIG. 1). In this pathway, arginine is first decarboxylated to agmatine, which is converted to putrescine and urea by agmatinase. Putrescine can then either be converted to GABA or to the polyamines spermine and spermidine (Pegg, (2009) IUBMB Life 61: 880-894). The rapidly increasing number of whole genome sequences has enabled the putative identification of arginase and agmatinase genes in many eukaryotes. However, since such annotation is based on sequence homology only, it does not enable definitive conclusions on the catalytic function of the encoded proteins.

Much of the knowledge on fungal arginine metabolism is based on studies with the model organism Saccharomyces cerevisiae. In S. cerevisiae, arginine is transported into the cell and subsequently hydrolyzed by arginase (Car1) to yield ornithine and urea (Sumrada and Cooper, (1992) Yeast 8: 311-314; Cooper et al., (1992) J Bacteriol 700 174: 48-55; Shima 64 et al., (2003) Appl Environ Microbiol 69: 715-718). An ATP-dependent amidolyase (Dur1,2) then converts urea into ammonia and carbon dioxide. Ornithine is further converted by an ornithine specific transaminase (Car2) into glutamate-γ-semialdehyde (GSA), which spontaneously forms 1-pyrroline-5-carboxylate (P5C) (Martin et al., (2003) Appl Environ Microbiol 69: 1623-1628). Due to subcellular compartmentation, S. cerevisiae is unable to convert cytosolic P5C directly to glutamate (Davis, (1986) Microbiol Rev 50: 280-313). Instead, P5C is reduced to proline using pyroline-5-carboxylate reductase (Pro3). Proline is then transported into the mitochondria (Brandriss and Falvey, (1992) Bacteriol 174: 5176), converted back to P5C by an oxidase (Put1) and, finally converted to glutamate by mitochondrial P5C dehydrogenase (Put2) (Davis, (1986) Microbiol Rev 50: 280-313). Since only very few physiological studies have been conducted on arginine metabolism in non-Saccharomyces yeasts, it is unknown whether the arginase pathway, which is essential for growth of S. cerevisiae on arginine as sole nitrogen source (Bossinger and Cooper, (1977) J Bacteriol 131: 163-173, is the only fungal pathway for arginine catabolism.

S. cerevisiae and Kluyveromyces lactis both belong to the Saccharomycetaceae family. These two related yeasts are considered to have genetically separated before the whole genome duplication (WGD) event that reshaped the genome of S. cerevisiae, furthermore K. lactis is regarded as resembling a pre-WGD ancestor of S. cerevisiae (Dujon, (2010) Nat Rev Genet 11: 512-524). While many studies have been conducted on the differences in sugar metabolism between these two species, the differences in amino-acid metabolism have not been studied in detail. Nonetheless, the complete genome sequence of K. lactis revealed many putative orthologs of S. cerevisiae genes involved in arginine metabolism (Dujon et al., (2004) Nature 430: 35-44; Souciet et al., (2009) BMC Genomics 13: 517; Dias et al., (2012) BMC Genomics 13: 517).

The selection of a microorganism that is transformed with recombinant DNA is strongly facilitated by the use of a suitable selection marker. The molecular biologist working with Saccharomyces cerevisiae has access to a large number of selectable markers (Solis-Escalente et al., (2013) FEMS Yeast Research 13: 126-139). However, auxotrophic markers and antibiotic resistance markers are sometimes undesired, thereby vertiginously decreasing the number of suitable markers. Eventually, the molecular geneticist is left with a limited number when he wants to genetically access wild type, allopolyploid and/or aneuploid prototrophic yeast strains.

The study of arginine metabolism resulted in the identification of two new "gain of function" dominant markers, which can be used, for example, for introducing genomic alterations in microorganisms, preferably in laboratory, wild and industrial yeast strains, including S. cerevisiae strains.

Therefore, the invention provides a nucleic acid molecule comprising (a) a nucleotide sequence encoding a guanidinobutyrase selection marker; and/or (b) a nucleotide sequence encoding a guanidino-amide hydrolase selection marker, whereby the nucleotide sequence is operably linked to (heterologous) promoter and terminator sequences. This nucleic acid molecule, also termed dominant marker cassette, provides a convenient dominant selectable marker system suitable for use in microorganisms, preferably in yeast.

Guanidinobutyrase (guanidino-acid hydrolase) and guanidino-amide hydrolase belong to a larger protein family, the ureohydrolase, which comprises enzymes sharing a 3-layer alpha-beta-alpha structure and play important roles in arginine/agmatine metabolism, the urea cycle and histidine degradation. Guanidinobutyrase catalyzes the hydrolysis of 4-guanidinobutanoate into 4-aminobutanoate and urea. Guanidino-amide hydrolase hydrolyses agmatine to urea and putrescine, the precursor for the biosynthesis of polyamines, spermidine and spermine. The ureohydrolase family comprises three further subgroups: i) the guanidino-amino acid hydrolase (arginase, EC3.5.3.1) that catalyses the conversion of arginine to urea and ornithine, ii) the proclavaminate amidinohydrolase (EC 3.5.3.22), an activity that is catalyses the conversion of amidino proclavaminate into urea and proclavaminate, an intermediate in clavulanic acid biosynthesis and iii) the formiminoglutamase (EC 3.5.3.8) that catalyzes the fourth step in histidine degradation, by hydrolysing N-formimidoyl-L-glutamate to L-glutamate and formamide.

Figure 2B:
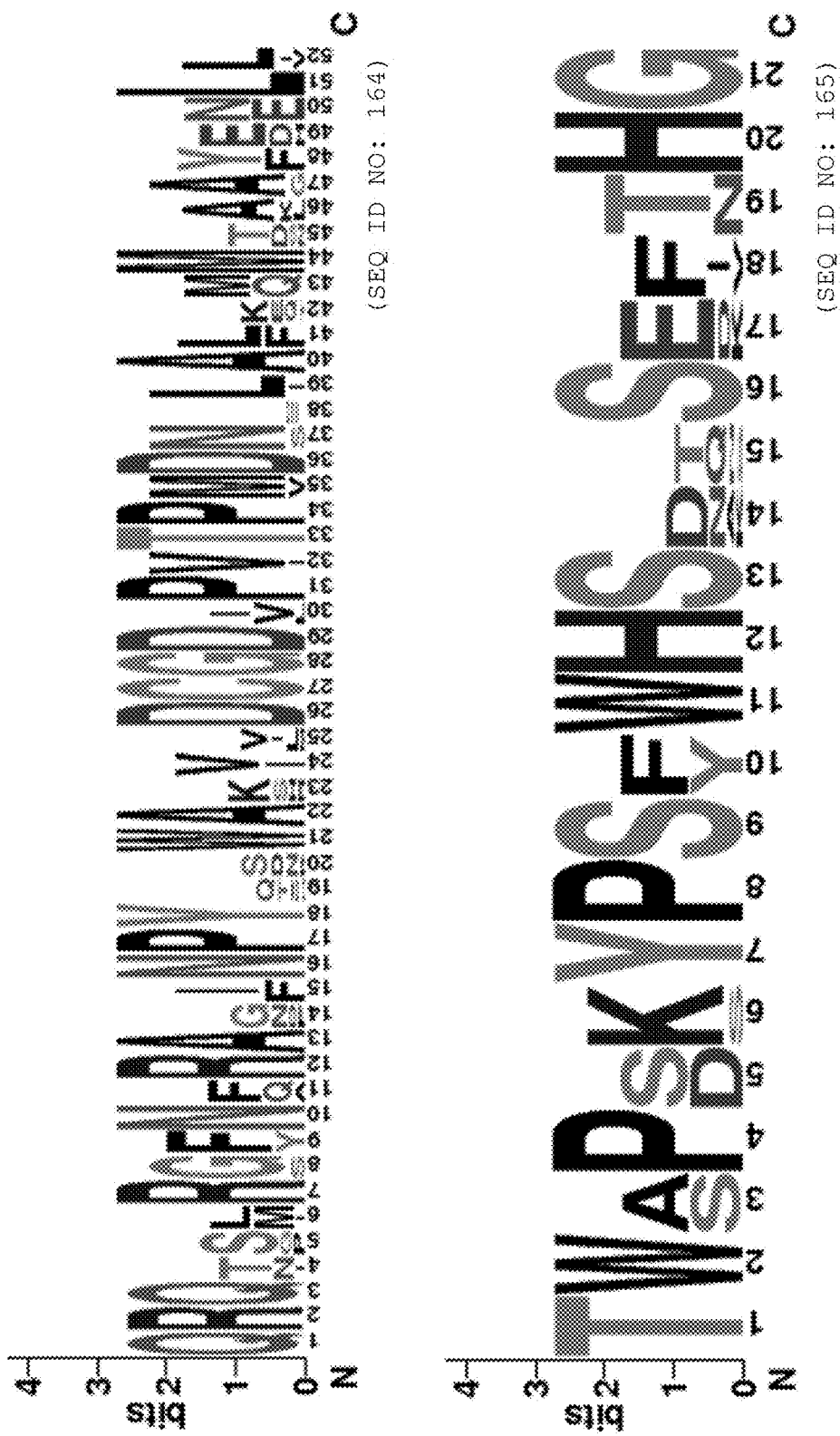

Said guanidinobutyrase-encoding nucleotide sequence encodes guanidino-acid hydrolase (EC.3.5.3.7). The nucleotide sequence preferably encodes a guanidino-acid hydrolase having one or both conserved domains as indicated in FIG. 2A and depicted in FIG. 2B, and/or encodes the consensus sequence as depicted in FIG. 2A. Said guanidino-acid hydrolase preferably comprises between 350 and 450 amino acids, preferably about 400 amino acids. Said guanidinobutyrase-encoding nucleotide sequence preferably encodes Kluyveromyces lactis NRRL Y-1140 hypothetical protein, having the sequence of GenBank XP_456325.1, as depicted in FIG. 3.

Figure 4B:
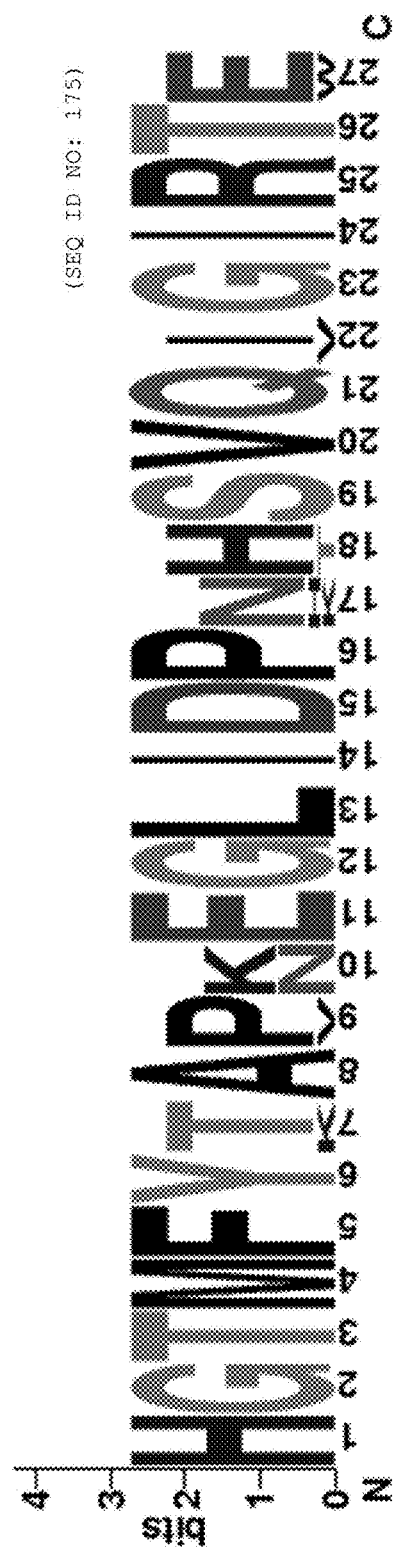

Said guanidino-amide hydrolase-encoding nucleotide sequence encodes agmatine ureohydrolase (agmatinase) (EC.3.5.3.11). The nucleotide sequence preferably encodes an agmatine ureohydrolase having the conserved domain as indicated in FIG. 4A and depicted in FIG. 4B, and/or encodes the consensus sequence as depicted in FIG. 4A. Said agmatine ureohydrolase preferably comprises between 290 and 330 amino acids, preferably about 306 amino acids. Said agmatine ureohydrolase preferably encodes the sequence of GenBank AAC75974.1, as depicted in FIG. 5.

Both guanidinobutyrase and agmatinase catalyze the formation of urea, a nitrogen source commonly assimilated by microorganisms such as S. cerevisiae. Therefore, these two ureohydrolase genes present the essential characteristics of a potential dominant "gain of function" selectable marker in microorganisms such as S. cerevisiae, when grown on guanidinobutyrate and/or agmatine as sole nitrogen source.

The invention thus provides a method of culturing a microorganism of the genus Saccharomycetaceae in the presence of guanidinobutyrate as sole nitrogen source, comprising (a) introducing a nucleic acid molecule comprising a nucleotide sequence encoding a guanidinobutyrase into the microorganism, whereby the nucleotide sequence is operably linked to promoter and terminator sequences, (b) culturing the microorganism such that the nucleic acid molecule encoding the guanidinobutyrase is expressed in the microorganism, and (c) culturing the microorganism in the presence of guanidinobutyrate as sole nitrogen source.

Said guanidinobutyrase-encoding nucleotide sequence preferably encodes Kluyveromyces lactis NRRL Y-1140 hypothetical protein.

Said promoter directs expression of the selection marker in the microorganism. Said terminator mediates efficient mRNA 3' end formation. Said promoter preferably is a yeast promoter, more preferably a yeast promoter selected from a glycolytic gene such as PGI1 (phosphoglucose isomerase 1), PFK1 (phosphofructokinase-1), PFK2 (phosphofructokinase-2), FBA1 (fructose-bisphosphate aldolase-1), TPI1 (triosephosphate isomerase-1), TDH1 (glyceraldehyde-3-phosphate dehydrogenase 1), TDH3 (glyceraldehyde-3-phosphate dehydrogenase 3), PGK1 (phosphoglycerate kinase 1), GPM1 (glycerate phosphomutase 1), PYK1 (pyruvate kinase 1), ENO1 (alpha-enolase), and/or ENO2 (enolase 2) promoter, or selected from ACT1 (actin 1), TEF1 (translational elongation factor EF-1 alpha), TEF2 (translational elongation factor EF-1 alpha 2), AgTEF2 (Ashbya gossypii TEF2 gene), PMA1 (plasma membrane P2-type H+-ATPase) promoter. Preferred promoter sequences are selected from promoter sequences of the PGI1, FBA1; TPI1; TDH3; PGK1; GPM1; ENO1; ENO2; and PYK1 genes. Terminators from a number of genes are known to the skilled person and have been employed, for example in expression vectors, including CYC1, TRP1, ADH1, MFl, FLP and D gene terminators (Romanos et al., 1992. Yeast 8: 423-488).

Preferred promoter sequences and terminator sequences do not comprise Saccharomyces sequences. Preferred promoter sequences and terminator sequences are from the Ashbya gossypii TEF gene encoding translation elongation factors and/or the regulatory sequences from K. lactis URA3 and LEU2 genes that encode the orotidine-5'-phosphate (OMP) decarboxylase and the beta-isopropylmalate dehydrogenase, respectively.

A nucleic acid molecule according to the invention, preferably encoding a guanidinobutyrase, is preferably provided as an amplified product or as a part of an amplified product. Said amplified product may further comprise sequences homologous to a first part of the genome of a microorganism, preferably an upstream part of a gene that is to be altered (termed target gene), and sequences homologous to second part of the genome of a microorganism, preferably a downstream part of the target gene, adjacent to the nucleic acid molecule. The term adjacent is used to indicate that the sequences homologous to the first part of the genome are located on one side of the nucleic acid molecule, while sequences homologous to the second part of the genome are located on the other side of the nucleic acid molecule. The sequences homologous to the first and second part of the genome preferably comprise between 20 and 1000 bp, more preferred between 30 and 500 bp, more preferred between 40 and 250 bp, more preferred between 50- to 80-bp of sequences. The sequences homologous to the upstream part of a gene preferably include the start codon. The sequences homologous to the downstream part of a gene preferably include the stop codon. Methods for producing an amplified product comprising a nucleic acid molecule according to the invention are known to a skilled person including, for example, polymerase chain reaction and nucleic acid sequence based amplification (NASBA).

A nucleic acid molecule according to the invention is preferably comprised in a vector. A vector contains bacterial resistance genes that, for example, allow growth of bacteria in the presence of an antibiotic. A most preferred vector is a plasmid, a double-stranded DNA molecule that is capable of replicating in bacteria independent of the chromosomal DNA.

Said vector, preferably plasmid, preferably additionally comprises sequences homologous to a first part of the genome of a microorganism, preferably an upstream part of a gene that is to be altered (termed target gene), and sequences homologous to second part of the genome of a microorganism, preferably a downstream part of the target gene, adjacent to the nucleic acid molecule. The term adjacent is used to indicate that the sequences homologous to the first part of the genome are located on one side of the nucleic acid molecule, while sequences homologous to the second part of the genome are located on the other side of the nucleic acid molecule.

The sequences homologous to the first part of the genome preferably comprise between 20 and 1000 bp, more preferred between 30 and 500 bp, more preferred between 40 and 250 bp, more preferred between 50- to 80-bp of sequences that are homologous to a first part of the genome, preferably to an upstream part of the gene to be altered or deleted. The sequences homologous to the upstream part of a gene preferably include the start codon.

The sequences homologous to the second part of the genome preferably comprise between 20 and 1000 bp, more preferred between 30 and 500 bp, more preferred between 40 and 250 bp, more preferred between 50- to 80-bp of sequences that are homologous to a second part of the genome, preferably to the downstream part of the gene to be altered or deleted. The sequences homologous to the downstream part of a gene preferably include the stop codon.

Said sequences that are homologous to a first and/or second part of the genome, preferably a target gene, may comprise sequences that are altered, when compared to the sequences of the genome. The terms altering, alteration and altered refer to a replacement of one or more nucleotides, the insertion of one or more nucleotides, and/or the deletion of one or more nucleotides anywhere within the homologous sequences.

A replacement of one or more nucleotides can be accomplished by altering one or more nucleotides in first part and/or the second part, preferably in sequences that are homologous to an upstream and/or downstream part of a gene. When the first part of homology and the second part of homology cover adjacent regions on the genome, preferably on a target gene, the integration of the targeting vector will result in an alteration of the genome.

Said vector, preferably plasmid, preferably further comprises a recognition site for an endonuclease at one end of the nucleic acid molecule according to the invention, and a copy of this recognition site at the other end of the nucleic acid molecule according to the invention. Said recognition sites preferably are located directly adjacent to the nucleic acid molecule according to the invention. Said endonuclease preferably is a rare-cutting endonuclease such as, for example, PacI (target recognition sequence 5'-TTAATTAA); AscI (target recognition sequence 5'-GGCGCGCC), and AsiSI (target recognition sequence 5'-GCGATCGC). PacI, AscI and AsiSI are available from New England Biolabs. The endonuclease more preferably is a homing endonuclease. The term homing endonuclease refers to an endonucleases that is encoded either as freestanding genes within introns, as a fusion with a host protein, or as a self-splicing intein. A preferred list of homing endonucleases is provided in Table 1. Additional examples of homing nucleases are I-DirI, I-NjaI, I-NanI, I-NitI, F-TevI, F-TevII, F-CphI, PI-MgaI, I-CsmI, which are all known to the skilled person. Further examples of homing nucleases are provided in Benjamin K (patent application US2012/052582), which is enclosed herein by reference.

Said vector, preferably plasmid, preferably further comprises a nucleic acid sequence of between 20 and 200 bp, preferably between 30 and 100 bp, more preferred about 40-50 bp, that is duplicated on either side of the nucleic acid molecule according to the invention, preferably outside of the recognition sites for an endonuclease. Said nucleic acid sequence of between 20 and 200 bp preferably is located in between the sequences homologous to the upstream part of a target gene and the recognition site for an endonuclease at one end of the nucleic acid molecule according to the invention, and in between the sequences homologous to the downstream part of the target gene and the recognition site for an endonuclease at the second end of the nucleic acid molecule according to the invention. The duplicated nucleic acid sequence preferably is identical to a region on the target genome, preferably on the target gene. The duplicated nucleic acid sequence of between 20 and 200 bp ensures seamless marker removal from the target genome by homologous recombination.

The invention further provides a method for producing a microorganism, preferably a yeast, comprising the nucleic acid molecule of the invention, the method comprising providing the microorganism with the nucleic acid molecule of the invention, selecting a microorganism having said nucleic acid molecule, thereby producing a microorganism comprising the nucleic acid molecule of the invention.

Methods for selecting a microorganism, preferably a yeast, having the nucleic acid according to the invention are known in the art and include Southern blotting and amplification of a nucleic acid product comprising at least a part of the nucleic acid molecule using at least one primer that is specific for the nucleic acid molecule. Alternatively, a vector that comprises the nucleic acid molecule according to the invention preferably further comprises a selectable marker that allows selection of a microorganism comprising the nucleic acid molecule of the invention.

The term specific, as used herein, refers to a primer or polynucleotide that will hybridize only to its target subsequence, typically in a complex mixture of nucleic acids, but to essentially no other sequences applying stringent conditions as is known to the skilled person. Stringent conditions are sequence-dependent and will be different in different circumstances. An extensive guide to the hybridization of nucleic acids is found in Tijssen (Tijssen, (1993) Hybridization with Nucleic Acid Probes, vol. 2, Laboratory techniques in biochemistry and molecular biology, Volume 24. Elsevier, Amsterdam). Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the primers complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). For selective or specific hybridization, a positive signal is at least two times background, preferably 10 times background hybridization.

A preferred method of the invention comprises selection of a microorganism, preferably a yeast, that functionally expresses the nucleic acid molecule encoding the selection marker. For example, a yeast may be selected that expresses guanidinobutyrase and/or agmatinase, as determined in an enzyme activity assay. Methods to determine guanidinobutyrase or agmatinase activity are known in the art. The amount of urea produced can be quantified using, for example, the Archibald method (Archibald, (1945) J Biol Chem 157: 507-518). A calibration line ranging from 0-1 mM of urea can be generated for quantification of the amount of urea.

The term "functionally express" in this specification is used to indicate that a gene of interest expresses the protein that is encoded by the gene, in an active form.

Said microorganism, preferably yeast, preferably of the genus Saccharomycetaceae, is preferably selected as it is able to grow on a substrate, preferably a synthetic medium, comprising, as sole nitrogen source, guanidinobutyrate and/or agmatine.

The invention further provides a microorganism, preferably yeast comprising the nucleic acid molecule of the invention. Said nucleic acid molecule of the invention preferably is integrated into the genome of said microorganism.

Said microorganism preferably is of the genus Saccharomycetaceae and comprises a nucleotide sequence encoding a guanidinobutyrase, preferably a guanidinobutyrase-encoding nucleotide sequence encoding *Kluyveromyces lactis* NRRL Y-1140 hypothetical protein.

The method of the invention can be applied to all microorganisms. If a microorganism has endogenous guanidinobutyrase and/or agmatinase activity, mutants of this organisms can be provided in which this activity is inactivated. Methods to inactivate a gene encoding guanidinobutyrase or agmatinase in a microorganism are known in the art. Suitable methods have been described in, for example, Akada et al., (2002). Yeast 19: 393-402; McNabb et al., (1997). Biotechniques, 22: 1134-1139; Storici et al., (1999). Yeast 15: 271-283; Gueldener et al., (2002). Nucleic Acids Res 30: e23; and Iwaki and Takegawa, (2004). Biosci Biotechnol Biochem 68: 545-550. Any of these methods can be applied to generate a microorganism in which an endogenous gene encoding guanidinobutyrase and/or agmatinase can be functionally inactivated.

The term functionally inactivated is used herein to indicate a reduced functional presence of a protein product of a gene in a microorganism, which is due to either a reduced level of expression or a reduced level of activity of the protein. Said reduced functional presence preferably results in a reduction of more than 90% of the protein amount and/or activity, more preferred a reduction of more than 95% of the protein amount and/or activity, most preferred a reduction of more than 99% of the protein amount and/or activity, compared to the corresponding protein activity in a related microorganism not comprising the functionally inactivated gene. In a most preferred embodiment, a functionally inactivated gene has no residual activity and is equivalent to a knock-out gene. The term knock-out gene refers to gene that has been made functionally inactive by partial or complete deletion of the coding region from the genomic DNA encoding said gene.

A microorganism, preferably yeast, of the invention preferably is a yeast of the genus Saccharomycetaceae. This genus includes *Saccharomyces* sensu stricto, *Kazachstania, Naumovozyma, Nakaseomyces* and *Vanderwaltozyma*. It has been proposed that these genera belonging to Saccharomycetaceae family have arisen after the whole genome duplication (post WGD) event that played a major role in the evolution of this subphylum.

A comparison of the nitrogen metabolism between *Saccharomyces cerevisiae* and *Kluyveromyces lactis* revealed substantial differences in arginine assimilation between these two yeast species. While deletion of the single *S. cerevisiae* arginase gene CAR1 was sufficient to abolish growth on arginine as sole nitrogen source, the corresponding Klcar1Δ mutant in *K. lactis* was still able to grow on arginine. This phenotypic difference was caused by the presence in *K. lactis* of a gene (KLLA0F27995g/KlGBU1) encoding for a guanidinobutyrase (EC.3.5.3.7), an enzyme not previously demonstrated in fungi. The presence of this enzyme provides the ability to grow on guanidinobutyrate as sole nitrogen source.

It was found that guanidinobutyrase orthologs are not present in the genus Saccharomycetaceae post WGD. Remarkably, one out of 34 annotated *S. cerevisiae* genome sequences, available from the SGD database (www.yeastgenome.org/) belonging to strain EC1118, did harbour a gene whose predicted protein sequence shared 62% sequence identity with a guanidinobutyrase sequence of *Kluyveromyces lactis*. Further inspection of the genome structure of strain EC1118 revealed that this ortholog was found on a genomic region acquired by horizontal transfer, most probably from *Torulaspora delbrueckii*. This gene origin fits the phylogenetic distribution of guanidinobutyrase orthologs in pre WGD Saccharomycetaceae genera (*Zygosaccharomyces, Lachancea, Torulaspora, Kluyveromyces* and *Eremothecium*), and in genera belonging to the CTG group and Dipodascacae (Kurtzman, (2003) FEMS Yeast Res 4: 233-245; Dujon, (2010) Nat Rev Genet 11: 512-524).

A preferred yeast is a laboratory, wild and industrial Lager brewing yeast *Saccharomyces pastorianus*, a laboratory, wild and industrial *S. cerevisiae* strain, preferably a *Saccharomyces* sensu stricto (*Saccharomyces paradoxus, S. mikatae, S. bayanus, S. eubayanus, S. kudriavzevii, S. paradoxus, S. arboricolus*), or a strain of *Kazachstania, Naumovozyma, Nakaseomyces* or *Vanderwaltozyma*, most preferred a laboratory, wild and industrial Lager brewing yeast *Saccharomyces pastorianus* or a *S. cerevisiae* strain.

The invention additionally provides a method of altering the genome of a microorganism, preferably a yeast genome, preferably a yeast of the genus Saccharomycetaceae, comprising providing the nucleic acid molecule of the invention, preferably encoding guanidinobutyrase, more preferably encoding *Kluyveromyces lactis* NRRL Y-1140 hypothetical protein, to said microorganism, and selecting a microorganism in which the genome has been altered by insertion of the nucleic acid molecule of the invention into the genome. A preferred method comprises providing a set of constructs according to the invention to said microorganism, and selecting a microorganism in which the genome has been altered, preferably by selection of a microorganism that functionally expresses said guanidinobutyrase. A preferred method comprises selecting a microorganism by culturing in the presence of guanidinobutyrate as sole nitrogen source.

The present invention further provides a set of constructs, comprising a first construct comprising a first part of the nucleotide sequence encoding a selection marker as indicated in claim 1, and a second construct comprising a second part of the nucleotide sequence encoding a selection marker as indicated in claim 1, whereby a fragment of the first part of the selection marker overlaps with a fragment that is present in the second part of the nucleotide sequence, allowing recombination between the first and second part of the nucleotide sequence.

This set of constructs overcomes a low targeting efficiency by providing a set of targeting constructs, in which the correct expression of a selection marker depends on a recombination event between the targeting constructs. It was found that the occurrence of a recombination event between the targeting constructs is markedly enhanced after integration of the targeting constructs in the correct targeting locus. Therefore, the target system of the present invention, comprising a set of targeting constructs, greatly enhances the percentage of correctly integrated constructs in microorganisms that express the selection marker, compared to a one-vector targeting system. Splitting the marker on two separate constructs limits the occurrence of false positives due to single cross over events. The split marker approach improves the ratio of true positives over false positives (Nielsen et al., 2006. Fungal Gen Biol 43: 54-64).

The term construct or targeting construct, as used herein, refers to an artificially constructed segment of nucleic acid. A preferred construct is a vector, preferably a vector that contains bacterial resistance genes for growth in bacteria. A most preferred construct is a plasmid, a linear or circular double-stranded DNA that is capable of replicating in bacteria independently of the chromosomal DNA.

The term overlap, as is used herein, refers to a duplicated region of the nucleotide sequence encoding a selection marker that is present on both set of constructs. The duplicated region is substantially identical and preferably is between 40 and 400 bp, preferably about 200 bp. The term substantially, as is used herein, is used to indicate that the region is at least 90% identical to ensure efficient recombination between the targeting constructs, more preferred at least 95% identical, more preferred at least 99% identical, more preferred 100% identical.

The first construct in the set of targeting constructs preferably further comprises a recognition site for an endonuclease and a first region of homology with a target genome of a microorganism, and the second construct further comprises a second region of homology with the target genome of the microorganism, and a copy of the endonuclease recognition site, whereby a coding sequence that encodes the endonuclease and which is coupled to an inducible promoter is present on the first or second construct; and a part of the first region of homology with the target genome on the first construct is duplicated between the copy of the endonuclease recognition site and the second region of homology with the target genome on the second construct; or a part of the second region of homology with the target genome on the second construct is duplicated between first region of homology with the target genome and the endonuclease recognition site on the first construct.

Said duplicated region of homology with the target genome on the first and second targeting construct preferably is between 20 and 200 bp, preferably between 40 and 100 bp, preferably about 80 bp. Said duplicated region of homology with the target genome on the first and second targeting construct allows scarless removal of the marker from the target genome by homologous recombination.

Figure 6:
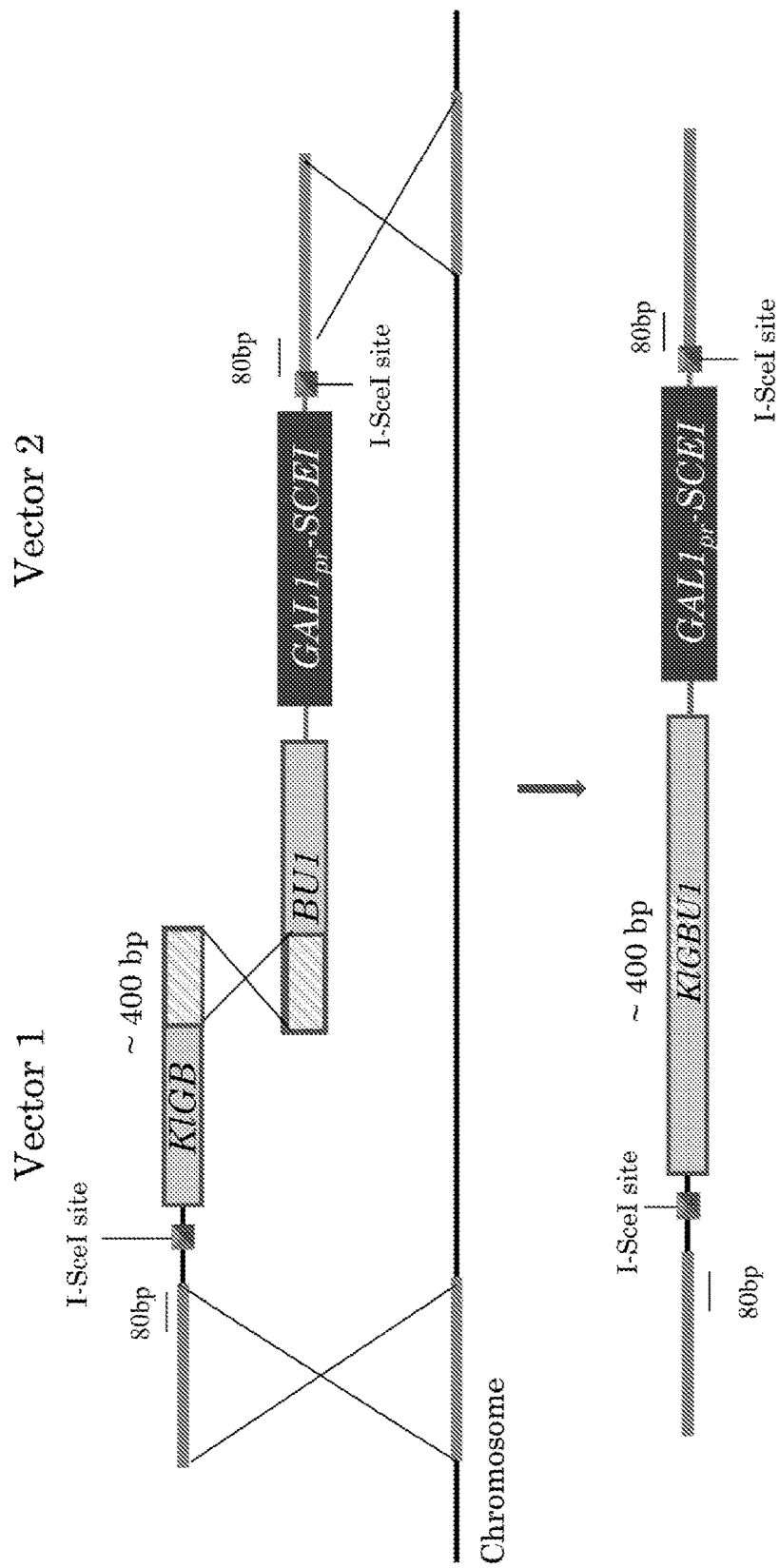

The first construct preferably comprises, in this order, a first region of homology with a target genome of a microorganism, a recognition site for an endonuclease, and a first part of a selection marker. The second construct preferably comprises, in this order, a region of overlap with the first part of the nucleotide sequence encoding a selection marker followed by a second part of the nucleotide sequence encoding the selection marker, a coding sequence that encodes the endonuclease and which is coupled to an inducible promoter, a copy of the endonuclease recognition site, a copy of a part of the first region of homology with the target genome that is present on the first construct, and a second region of homology with the target genome of the microorganism. This configuration is depicted in FIG. 6.

The target genome can be any location, preferably a gene, on the genome of a microorganism, preferably of a yeast, preferably of a yeast of the genus Saccharomytacea, of which the genomic sequence is to be altered. The term gene, as is used herein, refers to a part of the genome of the microorganism that comprises intronic and exonic parts of a gene, the promoter region of said gene, and genomic sequences that mediate the expression of said gene, such as, for example enhancer sequences.

The skilled person will understand that the targeting constructs are preferably used to alter a gene of a microorganism. Hence, the invention further provides a set of targeting constructs, comprising a first construct comprising a first region of homology with a target gene of a microorganism, a recognition site for an endonuclease, and a first part of a nucleotide sequence encoding a selection marker, and a second construct comprising a region of overlap with the first part of the nucleotide sequence encoding the selection marker followed by a nucleotide sequence encoding a second part of the selection marker, a copy of the endonuclease recognition site and a second region of homology with the target gene of the microorganism, whereby the overlapping fragments allow recombination between the first and second part of the nucleotide sequence encoding the selection marker; whereby a coding sequence that encodes the endonuclease and which is coupled to an inducible promoter is present on the first or second construct; and whereby a part of the first region of homology with the target gene on the first construct is duplicated between the copy of the endonuclease recognition site and the second region of homology with the target gene on the second construct; or a part of the second region of homology with the target gene on the second construct is duplicated between first region of homology with the target gene and the endonuclease recognition site on the first construct.

Said duplicated region of homology with the target gene on the first and second targeting construct preferably is between 20 and 200 bp, preferably between 40 and 100 bp, preferably about 80 bp.

The term alteration of the genomic sequence includes a replacement of one or more nucleotides, the insertion of one or more nucleotides, and/or the deletion of one or more nucleotides anywhere within a genome, preferably within a gene.

For example, if the first and second region of homology with a target gene comprise adjacent genomic sequences of the gene, a replacement of one or more nucleotides in the first region of homology, and/or in the second region of homology, will result in an alteration of the gene following homologous targeting with the set of targeting constructs according to the invention. Said replacement of one or more nucleotides preferably is in the region of homology with the target gene that is present on the first and on the second construct.

Said alteration of the genomic sequence preferably is a deletion of one or more nucleotides, preferably anywhere within the gene. For example, if the first and second region of homology with a target gene comprise genomic sequences of the gene that are separated on the genome of the organism, an alteration of the gene following homologous targeting with the set of targeting constructs according to the invention will result in a deletion of the region that was located between the first and second region of homology on the parental chromosome.

Said first construct preferably comprises a first part, preferably the first two-third or first half, of a region that encodes the selection marker. For example, the guanidinobutyrase protein of *K. lactis* has 410 amino acids, which is encoded by a nucleic acid sequence of 1230 bp. Said first construct preferably comprises between 400 and 800 bp of the coding region of this protein, more preferred between 500 and 700 bp. The second construct preferably comprises between 400 and 800 bp of the coding region of this protein, more preferred between 500 and 700 bp.

The region of overlap between the first and second part of the selection marker preferably is between about 50 bp and about 600 bp, preferably about 200 bp.

The first or second targeting construct comprises a coding sequence that encodes an endonuclease and which is coupled to an inducible promoter. The endonuclease preferably is a rare-cutting endonuclease such as, for example, PacI (target recognition sequence 5'-TTAATTAA); AscI (target recognition sequence 5'-GGCGCGCC), and AsiSI (target recognition sequence 5'-GCGATCGC). PacI, AscI and AsiSI are available from New England Biolabs. The endonuclease more preferably is a homing endonuclease. The term homing endonuclease refers to an endonucleases that is encoded either as freestanding genes within introns, as a fusion with a host protein, or as a self-splicing intein. A preferred list of homing endonucleases is provided in Table 1. Additional examples of homing nucleases are I-DirI, I-NjaI, I-NanI, I-NitI, F-TevI, F-TevII, F-CphI, PI-MgaI, I-CsmI, which are all known to the skilled person. Further examples of homing nucleases are provided in US patent application US 2012/052582, which is enclosed herein by reference.

A preferred homing nuclease is PI-PspI (New England Biolabs; recognition sequence 5'-TGGCAAACAGCTAT-TATGGGTATTATGGGT (SEQ ID NO: 1)) or PI-SceI (New England Biolabs; recognition sequence 5'-ATCTAT-GTCGGGTGCGGAGAAAGAGGTAAT (SEQ ID NO: 2)). The coding sequences of most homing endonuclease are known. For example, the coding sequence of PI-SceI and of PI-PspI are available from public databases (GenBank accession number Z74233.1 and Genbank accession number U00707.1, respectively). The skilled person will understand that a sequence that differs from the publicly available sequence for a nuclease, may still encode the nuclease. For example, the term PI-PspI coding region may include a sequence that deviates from the publicly available sequence, for example by codon optimization, but which still expresses an active endonuclease that recognizes and digests the indicated target recognition sequence.

Said endonuclease is preferably under control of an inducible promoter. The term inducible promoter, as is used herein, refers to a promoter of which the expression can be regulated. Inducible promoters are known to the skilled person. Examples of inducible promoters that have been employed in yeast are the GAL1 promoter and the GAL10 promoter, which both are inducible by galactose, the SUC2 promoter, which is inducible by sucrose, the MAL12 promoter, which is inducible by maltose; the CUP1 promoter, which is inducible by copper, and the tetO7 and tetO2 promoters, which are both inducible by tetracycline [Gari et al., (1997) Yeast 13: 837-48; Yen et al., (2003) Yeast 20 1255-62]. A preferred inducible promoter is the GAL1 promoter.

One recognition site comprising the target recognition sequence for the endonuclease, is located adjacent to (behind) the first region of homology with a target gene of a microorganism on the first construct. A copy of this recognition site is located adjacent to (in front of) the second region of homology with the target gene of the microorganism on the second construct. The skilled person will understand that when a part of the first region of homology with the target gene on the first construct is duplicated between the copy of the endonuclease recognition site and the second region of homology with the target gene on the second construct, said copy of the recognition site is located adjacent to (in front of) the duplication of the first region of homology with the target gene on the second construct. Alternatively, the recognition site is located adjacent to (behind) the duplicated part of the second region of homology with the target gene on the first construct when a part of the second region of homology with the target gene on the second construct is duplicated on the first construct. The selection marker, including promoter and terminator sequences, and the coding region of the endonuclease, including the inducible promoter, are between the recognition site on the first construct and the copy of this recognition site on the second construct.

The invention further provides a method for altering a genome, preferably a target gene, in a microorganism, comprising providing the set of targeting constructs according to the invention to said microorganism, and selecting a microorganism in which the genome has been altered. Said selection of a microorganism in which the genome has been altered is preferably accomplished by selection of a microorganism that functionally expresses a recombined selection marker.

As is indicated herein above, the occurrence of a recombination event between the targeting constructs is markedly enhanced after integration of the targeting constructs in the correct targeting locus. Hence, the presence of a functionally recombined selection marker is highly indicative for the presence of correctly integrated targeting constructs in the target genome and, therefore, of an altered genome in the microorganism.

As is indicated herein above, the terms altering, alteration and altered refer to a replacement of one or more nucleotides, the insertion of one or more nucleotides, and/or the deletion of one or more nucleotides anywhere in the genome, preferably within a target gene.

A replacement of one or more nucleotides can be accomplished by altering one or more nucleotides in the first region of homology and/or in the second region of homology. When the first region of homology and the second region of homology with the target genome cover adjacent regions of the genome, preferably target gene, the integration of the targeting vectors will result in an alteration of the genome. When present, said replacement of one or more nucleotides is preferably accomplished by altering one or more nucleotides in the overlapping region of homology with the genome that is present on the first and on the second construct.

Said alteration of a genomic sequence preferably is a deletion of one or more nucleotides anywhere within a genome, preferably within a gene. For example, if the first and second region of homology with a target genome comprise genomic sequences that are separated on the genome of the organism, an alteration of the genome following homologous targeting with the set of targeting constructs according to the invention will result in a deletion of the region that was located between the first and second region of homology on the parental chromosome.

The invention further provides a method for producing a microorganism comprising an altered genome, preferably an altered gene, the method comprising providing the set of targeting constructs according to the invention to said microorganism, and selecting a microorganism in which the genome has been altered and that functionally expresses a recombined selection marker.

The method for producing a microorganism comprising an altered genome preferably comprises inducing the inducible promoter for expression of the endonuclease, thereby removing the selection marker and the coding region of the endonuclease, including the inducible promoter, from the target genome.

The invention further provides a microorganism, comprising a genomic alteration that is produced by the methods of the invention. When present, the duplicated regions of homology with the target genome on the first and second targeting construct ensure seamless marker removal from the target genome by homologous recombination. The resulting microorganism comprises only the alteration or alterations that were present on the first and/or second targeting construct, or that were induced by recombination of the targeting constructs into the targeting genome, such as an insertion into the targeting genome or a deletion from the targeting genome.

The invention further provides a microorganism, comprising a genomic alteration, preferably an alteration of a target gene, the alteration comprising an insertion of a functionally recombined selection marker and a coding sequence for an endonuclease that is coupled to an inducible promoter, whereby the target genome comprises one copy of a recognition sequence for the endonuclease on both sites of the insertion.

The invention further provides a kit comprising the nucleic acid molecule of the invention, or the set of constructs of the invention. Said kit may further comprise methods and means for growth of a microorganism, preferably a yeast, preferably of the Saccharomycetaceae, in synthetic medium comprising guanidinobutyrate and/or agmatine, and/or the identification of guanidinobutyrase or agmatinase enzyme such as, for example, guanidinobutyric acid and/or agmatine.

The invention also provides a method of culturing a microorganism, preferably a yeast, preferably of the Saccharomycetaceae, in the presence of guanidinobutyrate or agmatine as sole nitrogen source, comprising: (a) introducing the nucleic acid molecule of the invention into the microorganism, and (b) culturing the microorganism such that the nucleotide molecule is expressed in the microorganism.

The invention also provides a method of culturing a microorganism, preferably a yeast, preferably of the Saccharomycetaceae, in the presence of guanidinobutyrate or agmatine as sole nitrogen source, comprising: (a) introducing the set of constructs of the invention into the microorganism, and (b) culturing the microorganism such that following recombination of the targeting constructs the nucleotide molecule encoding the selection marker is expressed in the microorganism.

The invention further provides a method for producing a microorganism comprising an altered genome, the method comprising providing a microorganism comprising an alteration of the genome, preferably of a target gene, the alteration comprising an insertion of a functionally recombined nucleotide sequence encoding a selection marker and a coding sequence for an endonuclease that is coupled to an inducible promoter, whereby the target genome comprises one copy of a recognition sequence for the endonuclease on both sites of the insertion, and inducing the inducible promoter to remove the nucleic acid sequences in between the recognition sequences of the endonuclease. Again, when present, the duplicated regions of homology with the target gene on the first and second targeting constructs ensure seamless marker removal from the target genome by homologous recombination by providing the genomic DNA with a small homologous piece to re-connect the broken DNA strands efficiently. The resulting microorganism comprises only the alteration or alterations that were present on the first and/or second targeting construct, or that were induced by recombination of the targeting constructs into the targeting genome, such as an insertion into the targeting genome or a deletion from the genome, preferably an insertion into a targeted gene or a deletion of the targeted gene or a deletion from within the targeted gene.

For the purpose of clarity and a concise description, features are described herein as part of the same or separate embodiments, however, it will be appreciated that the scope of the invention may include embodiments having combinations of all or some of the features described.

TABLE 1

| Enzyme | Recognition sequence | Cut | SF | Source | D | SCL |
|---|---|---|---|---|---|---|
| I-AniI | 5' TTGAGGAGGTTTCTCTGTAAA TAA 3' (SEQ ID NO: 3) 3' AACTCCTCCAAAGAGACATTT ATT 5' (complement of SEQ ID NO: 3) | 5' ---TTGAGGAGGTTTC (SEQ ID NO: 4) TCTGTAAATAA--- 3' (SEQ ID NO: 5) 3' ---AACTCCTCC (complement of SEQ ID NO: 6) AAAGAGACATTTAT T--- 5' (complement of SEQ ID NO: 7) | HI | Aspergillus nidulans | E | mito |
| I-CeuI | 5' TAACTATAACGGTCCTAAGGT AGCGA 3' (SEQ ID NO: 8) 3' ATTGATATTGCCAGGATTCCA TCGCT 5' (complement of SEQ ID NO: 8) | 5' ---TAACTATAACGGTCC TAA (SEQ ID NO: 9) GGTAGCGA--- 3 3' ---ATTGATATTGCCAG (complement of SEQ ID NO: 10) GATTCCATCGC T--- 5' (complement of SEQ ID NO: 10) | HI | Chlamydomonas eugametos | E | chloro |
| I-ChuI | 5' GAAGGTTTGGCACCTCGATGT CGGCTCATC 3' (SEQ ID NO: 12) 3' CTTCCAAACCGTGGAGCTACA GCCGAGTAG 5' (complement of SEQ ID NO: 12) | 5' ---GAAGGTTTGGCACCTCG (SEQ ID NO: 13) ATGTCGG CTCATC--- 3' (SEQ ID NO: 14) 3' ---CTTCCAAACCGTG (complement of SEQ ID NO: 15) GAGCTACAGCCGAGTA G--- 5' (complement of SEQ ID NO: 16) | HI | Chlamydomonas humicola | E | chloro |
| I-CpaI | 5' CGATCCTAAGGTAGCGAAATT CA 3' (SEQ ID NO: 17) 3' GCTAGGATTCCATCGCTTTAA GT 5' (complement of SEQ ID NO: 17) | 5' ---CGATCCTAAGGTAGCGA A (SEQ ID NO: 18) ATTCA --- 3 3' ---GCTAGGATTCCATC (complement of SEQ ID NO: 19) GCTTTAAGT--- 5' | HI | Chlamydomonas pallidostigmata | E | chloro |

TABLE 1-continued

| Enzyme | Recognition sequence | Cut | SF | Source | D | SCL |
|---|---|---|---|---|---|---|
| I-CpaII | 5' CCCGGCTAACTCTGTGCCAG 3' (SEQ ID NO: 20)<br>3' GGGCCGATTGAGACACGGTC 5' (complement of SEQ ID NO: 20) | 5' ---CCCGGCTAACTC (SEQ ID NO: 21)T GTGCCAG--- 3'<br>5' ---GGGCCGAT TGAGACAC GGTC--- 3' (complement of SEQ ID NO: 22) | HI | *Chlamydomonas pallidostigmata* | E | chloro |
| I-CreI | 5' CTGGGTTCAAAACGTCGTGAG ACAGTTTGG 3' (SEQ ID NO: 23)<br>3' GACCCAAGTTTTGCAGCACTC TGTCAAACC 5' (complement of SEQ ID NO: 23) | 5' ---CTGGGTTCAAAACGT CGTGA (SEQ ID NO: 24) GACAGTTTGG--- 3 (SEQ ID NO: 25)<br>3' ---GACCCAAGTTTTGCAG (complement of SEQ ID NO: 26) CACTCTGTCAAACC --- 5' (complement of SEQ ID NO: 27) | HI | *Chlamydomonas reinhardtii* | E | chloro |
| DmoI | 5' ATGCCTTGCCGGGTAAGTTCC GGCGCGCAT 3' (SEQ ID NO: 28)<br>3' TACGGAACGGCCCATTCAAGG CCGCGCGTA 5' (complement of SEQ ID NO: 28) | 5' ---ATGCCTTGCCGGGTAA (SEQ ID NO: 29) GTTCCGGCGCGCAT--- 3' (SEQ ID NO: 30)<br>3' ---TACGGAACGGCC (complement of SEQ ID NO: 31) CATTCAAGGCCGCG CGTA--- 5' (complement of SEQ ID NO: 32) | | *Desulfurococcus mobilis* | A | Chrm |
| H-DreII | 5' CAAAACGTCGTAAGTTCCGGC GCG 3' (SEQ ID NO: 33)<br>3' GTTTTGCAGCATTCAAGGCCG CGC 5' (complement of SEQ ID NO: 33) | 5' ---CAAAACGTCGTAA (SEQ ID NO: 34) GTTCCGGCGCG--- 3' (SEQ ID NO: 35)<br>3' ---GTTTTGCAG CATTCAAGGCCGCGC--- 5' (complement of SEQ ID NO: 36) | HI | *Escherichia coli* | B | |
| I-HmuI | 5' AGTAATGAGCCTAACGCTCAG CAA 3' (SEQ ID NO: 37)<br>3' TCATTACTCGGATTGCGAGTC GTT 5' (complement of SEQ ID NO: 37) | : *<br>3' ---TCATTACTCGGATTGC (complement of SEQ ID NO: 38) GAGTCGTT--- 5' | HIII | *Bacillus subtilis* SPO1 | B | phage |
| I-HmuII | 5' AGTAATGAGCCTAACGCTCAA CAA 3' (SEQ ID NO: 39)<br>3' TCATTACTCGGATTGCGAGTT GTT 5' (complement of SEQ ID NO: 39) | 3' ---TCATTACTCGGATTGC GAGTTGTTN$_{35}$ NNNN--- 5' (complement of SEQ ID NO: 176) | HIII | *Bacillus subtilis* phage SP82 | B | phage |
| I-LlaI | 5' CACATCCATAACCATATCATT TTT 3' (SEQ ID NO: 41)<br>3' GTGTAGGTATTGGTATAGTAA AAA 5' (complement of SEQ ID NO: 41) | 5' ---CACATCCATAA (SEQ ID NO: 42) CCATATCATTTTT--- 3' (SEQ ID NO: 43)<br>3' ---GTGTAGGTATTGGTATA GTAA (complement of SEQ ID NO: 44) AAA--- 5' | HIII | *Lactococcus lactis* | B | chrm |
| I-MsoI | 5' CTGGGTTCAAAACGTCGTGAG ACAGTTTGG 3' (SEQ ID NO: 45)<br>3' GACCCAAGTTTTGCAGCACTC TGTCAAACC 5' (complement of SEQ ID NO: 45) | 5' ---CTGGGTTCAAAACGTCGT GA (SEQ ID NO: 46) GACAGTTTGG--- 3' (SEQ ID NO: 47)<br>3' ---GACCCAAGTTTTGCAG (complement of SEQ ID NO: 48) CACTCTGTCAAACC --- 5' (complement of SEQ ID NO: 49) | | *Monomastix sp.* | E | |
| PI-PfuI | 5' GAAGATGGGAGGAGGGACCGG ACTCAACTT 3'(SEQ ID NO: 50)<br>3' CTTCTACCCTCCTCCCTGGCC TGAGTTGAA 5' (complement of SEQ ID NO: 50) | 5' ---GAAGATGGGAGGAGGG (SEQ ID NO: 51) ACCGGACTCAACTT--- 3' (SEQ ID NO: 52)<br>3' ---CTTCTACCCTCC (complement of SEQ ID NO: 53) TCCCTGGCCTGAGT TGAA--- 5' (complement of SEQ ID NO: 54) | | *Pyrococcus furiosus* Vc1 | A | |

TABLE 1-continued

| Enzyme | Recognition sequence | Cut | SF | Source | D | SCL |
| --- | --- | --- | --- | --- | --- | --- |
| PI-PkoII | 5' CAGTACTACGGTTAC 3' (SEQ ID NO: 55)<br>3' GTCATGATGCCAATG 5' (complement of SEQ ID NO: 55) | 5' ---CAGTACTACG (SEQ ID NO: 56) GTTAC--- 3'<br>3' ---GTCATG ATGCCAATG--- 5' | | *Pyrococcus kodakaraensis* KOD1 | A | |
| I-PorI | 5' GCGAGCCCGTAAGGGTGTGTA CGGG (SEQ ID NO: 57)<br>3' CGCTCGGGCATTCCCACACAT GCCC (complement of SEQ ID NO: 57) | 5' ---GCGAGCCCGTAAGGGT (SEQ ID NO: 58) GTGTACGGG--- 3'<br>3' ---CGCTCGGGCATT (complement of SEQ ID NO: 59) CCCACACATGCCC --- 5' (complement of SEQ ID NO: 60) | HIII | *Pyrobaculum organotrophum* | A | chrm |
| I-PpoI | 5' TAACTATGACTCTCTTAAGGT AGCCAAAT (SEQ ID NO: 61)<br>3' ATTGATACTGAGAGAATTCCA TCGGTTTA (complement of SEQ ID NO: 61) | 5' ---TAACTATGACTCTCTT AA (SEQ ID NO: 62) GGTAGCCAAAT--- 3' (SEQ ID NO: 63)<br>3' ---ATTGATACTGAGAG (complement of SEQ ID NO: 64) AATTCCATCGGTTT A--- 5' (complement of SEQ ID NO: 65) | HIV | *Physarum polycephalum* | E | nuclear |
| PI-PspI | 5' TGGCAAACAGCTATTATGGGT ATTATGGGT (SEQ ID NO: 66)<br>3' ACCGTTTGTCGATAATACCCA TAATACCCA (complement of SEQ ID NO: 66) | 5' ---TGGCAAACAGCTATTAT (SEQ ID NO: 67) GGGTATTATGGGT--- 3' (SEQ ID NO: 68)<br>3' ---ACCGTTTGTCGAT (complement of SEQ ID NO: 69) AATACCCATAATACC CA--- 5' (complement of SEQ ID NO: 70) | HI | *Pyrococcus* sp. | A | chrm |
| I-ScaI | 5' TGTCACATTGAGGTGCACTAG TTATTAC (SEQ ID NO: 71)<br>3' ACAGTGTAACTCCACGTGATC AATAATG (complement of SEQ ID NO: 71) | 5' ---TGTCACATTGAGGTGCA CT (SEQ ID NO: 72) AGTTATTAC--- 3'<br>3' ---ACAGTGTAACTCCAC (complement of SEQ ID NO: 73) GTGATCAATAATG --- 5' (complement of SEQ ID NO: 74) | HI | *Saccharomyces capenis* | E | |
| I-SceI | 5' AGTTACGCTAGGGATAACAGG GTAATATAG (SEQ ID NO: 75)<br>3' TCAATGCGATCCCTATTGTCC CATTATATC (complement of SEQ ID NO: 75) | 5' ---AGTTACGCTAGGGATAA (SEQ ID NO: 76) CAGGGTAATATAG--- 3' (SEQ ID NO: 77)<br>3' ---TCAATGCGATCCC (complement of SEQ ID NO: 78) TATTGTCCATTATA TC--- 5' (complement of SEQ ID NO: 79) | HI | *Saccharomyces cervisiae* | E | mito |
| PI-SceI | 5' ATCTATGTCGGGTGCGGAGAA AGAGGTAATGAAATGCA (SEQ ID NO: 80)<br>3' TAGATACAGCCCACGCCTCTT TCTCCATTACTTTACCGT (complement of SEQ ID NO: 80) | 5' ---ATCTATGTCGGGTGC (SEQ ID NO: 81) GGAGAAAGAGGTAATGAAATG GCA --- 3' (SEQ ID NO: 82)<br>3' ---TAGATACAGCC (complement of SEQ ID NO: 83) CACGCCTCTTTCT CCATTACTTTACCGT --- 5' (complement of SEQ ID NO: 84) | HI | *Saccharomyces cervisiae* | E | |
| I-SceII | 5' TTTTGATTCTTTGGTCACCCT GAAGTATA (SEQ ID NO: 85)<br>3' AAAACTAAGAAACCAGTGGGA CTTCATAT (complement of SEQ ID NO: 85) | 5' ---TTTTGATTCTTTGGTCA CCCT (SEQ ID NO: 86) TGAAGTATA--- 3'<br>3' ---AAAACTAAGAAACCAG (complement of SEQ ID NO: 87) TGGGACTTCATAT --- 5' (complement of SEQ ID NO: 88) | HI | *Saccharomyces cervisiae* | E | mito |

TABLE 1-continued

| Enzyme | Recognition sequence | Cut | SF | Source | D | SCL |
|---|---|---|---|---|---|---|
| I-SceIII | 5' ATTGGAGGTTTTGGTAACTAT TTATTACC (SEQ ID NO: 89) 3' TAACCTCCAAAACCATTGATA AATAATGG (complement of SEQ ID NO: 89) | 5' ---ATTGGAGGTTTTGGTAA C (SEQ ID NO: 90) TATTTATTACC--- 3' (SEQ ID NO: 91) 3' ---TAACCTCCAAAACC (complement of SEQ ID NO: 92) ATTGATAAATAAT GG--- 5' (complement of SEQ ID NO: 96) | HI | *Saccharomyces cervisiae* | E | mito |
| I-SceIV | 5' TCTTTTCTCTTGATTAGCCCT AATCTACG (SEQ ID NO: 94) 3' AGAAAAGAGAACTAATCGGGA TTAGATGC (complement of SEQ ID NO: 94) | 5' ---TCTTTTCTCTTGATTA (SEQ ID NO: 95) GCCCTAATCTACG--- 3' (SEQ ID NO: 96) 3' ---AGAAAAGAGAAC (complement of SEQ ID NO: 97) TAATCGGGATTAGA TGC--- 5' (complement of SEQ ID NO: 98) | HI | *Saccharomyces cervisiae* | E | mito |
| I-SceV | 5' AATAATTTTCTTCTTAGTAAT GCC (SEQ ID NO: 99) 3' TTATTAAAAGAAGAATCATTA CGG (complemt of SEQ ID NO: 99) | 5' ---AATAATTTTCT (SEQ ID NO: 100) TCTTAGTAATGCC--- 3' (SEQ ID NO: 101) 3' ---TTATTAAAAGAAGAAT CATTA (complement of SEQ ID NO: 102) CGG--- 5' | HIII | *Saccharomyces cervisiae* | E | mito |
| I-SceVI | 5' GTTATTTAATGTTTTAGTAGT TGG (SEQ ID NO: 103) 3' CAATAAATTACAAAATCATCA ACC (complement of SEQ ID NO: 103) | 5' ---GTTATTTAATG (SEQ ID NO: 104) TTTTAGTAGTTGG--- 3' (SEQ ID NO: 105) 3' ---CAATAAATTACAAAAT CATCA (complement of SEQ ID NO: 106) ACC--- 5' | HIII | *Saccharomyces cervisiae* | E | mito |
| I-SceVII | 5' TGTCACATTGAGGTGCACTAG TTATTAC (SEQ ID NO: 107) 3' ACAGTGTAACTCCACGTGATC AATAATG (complement of SEQ ID NO: 107) | Unknown | HI | *Saccharomyces cervisiae* | E | mito |
| I-Ssp6803I | 5' GTCGGGCTCATAACCCGAA (SEQ ID NO: 108) 3' CAGCCCGAGTATTGGGCTT (complement of SEQ ID NO: 108) | 5' ---GTCGGGCT CATAACCCGAA--- 3' (SEQ ID NO: 109) 3' ---CAGCCCGAGTA (complement of SEQ ID NO: 110) TTGGGCTT--- 5' | | *Synechocystis* sp. PCC 6803 | B | |
| I-TevI | 5' AGTGGTATCAACGCTCAGT AGATG (SEQ ID NO: 111) 3' TCACCATAGT TGCGAGTCAT CTAC (complement of SEQ ID NO: 111) | 5' ---AGTGGTATCAAC (SEQ ID NO: 112) GCTCAGTAGATG--- 3' (SEQ ID NO: 113) 3' ---TCACCATAGT (complement of SEQ ID NO: 114) TGCGAGTCATCT AC--- 5' (complement of SEQ ID NO: 115) | HII | *Escherichia coli* phate T4 | B | phage |
| I-TevII | 5' GCTTATGAGTATGAAGTGA ACACGTTATTC (SEQ ID NO: 116) 3' CGAATACTCATACTTCACT TGTGCAATAAG (complement of SEQ ID NO: 116) | 5' ---GCTTATGAGTATGAAG TGAACACGT (SEQ ID NO: 117) TATTC--- 3' 3' ---CGAATACTCATACTTC ACTTGTG (complement of SEQ ID NO: 118) CAATAA G--- 5' | HII | *Escherichia coli* phate T4 | B | phage |
| I-TevIII | 5' TATGTATCTTTTGCGTGTACC TTTAACTTC (SEQ ID NO: 119) 3' ATACATAGAAAACGCACATGG AAATTGAAG (complement of SEQ ID NO: 119) | 5' ---T ATGTATCTTTTGCG TGTACCTTTAACTTC--- 3' (SEQ ID NO: 120) 3' ---AT ACATAGAAAACGC ACATGGAAATTGAAG--- 5' (complement of SEQ ID NO: 121) | HIII | *Escherichia coli* phate RB3 | B | phage |

TABLE 1-continued

| Enzyme | Recognition sequence | Cut | SF | Source | D | SCL |
|---|---|---|---|---|---|---|
| PI-TliI | 5' TAYGCNGAYACNGACGGYTTYT (SEQ ID NO: 122) 3' ATRCGNCTRTGNCTGCCTAARA (complement of SEQ ID NO: 122) | 5' ---TAYGCNGAYACNGACG (SEQ ID NO: 123) YTTYT--- 3' 3' ---ATRCGNCTRTGNC (complement of SEQ ID NO: 124) TGCCTAARA--- 5' | HI | Thermococcus litoralis | A | chrm |
| PI-TliII | 5' AAATTGCTTGCAAACAGCTATTACGGCTAT (SEQ ID NO: 125) 3' TTTAACGAACGTTTGTCGATAATGCCGATA (complement of SEQ ID NO: 125) | Unknown ** | HI | Thermococcus litoralis | A | chrm |
| I-Tsp061I | 5' CTTCAGTATGCCCCGAAAC (SEQ ID NO: 126) 3' GAAGTCATACGGGGCTTTG (complement of SEQ ID NO: 126) | 5' ---CTTCAGTAT GCCCCG AAAC--- 3' (SEQ ID NO: 127) 3' ---GAAGT CATACGGGGC TTTG--- 5' (complement of SEQ ID NO: 128) | | Thermoproteus sp. IC-061 | A | |
| I-Vdi141I | 5' CCTGACTCTCTTAAGGTAGCCAAA (SEQ ID NO: 129) 3' GGACTGAGAGAATTCCATCGGTTT (complement of SEQ ID NO: 129) | 5' ---CCTGACTCTCTTAA (SEQ ID NO: 130) GGTAGCCAAA--- 3' (SEQ ID NO: 131) 3' ---GGACTGAG AGAATTC CATCGGTTT--- 5' (complement of SEQ ID NO: 132) | | Vulcanisaeta distributa IC-141 | A | |

Table 1: Overview of Homing Endonucleases and their Target Sequences.
Abbreviations: SF Structural family: HI: LAGLIDADG (SEQ ID NO: 133) family; HII: GIY-YIG family; Hill: H-N-H family; HIV: His-Cys box family.
D: Biological domain of the source: A: archaea; B: bacteria; E: eukarya.
SCL: Subcelullar location: chloro: chloroplast; chrm: chromosomal; mito: mitochondrial; nuclear: extra chromosomal nuclear; phage: bacteriophage.

TABLE 2

Saccharomyces cerevisiae strains used in this study.

| Strain | Genotype | Reference |
|---|---|---|
| CEN.PK113-7D | Prototrophic reference strain MATa | (Nijkamp et al., 2012) |
| CEN.PK113-5D | MATa ura3-52 | (Entian & Kötter, 2007) |
| IMZ312 | MATa ura3-52 pAG426GPD-ccdB (TDH3$_{pr}$-CYC1$_{ter}$ URA3 2μ) | This study |
| IME215 | MATa ura3-52 pUDE264 (TDH3$_{pr}$-KlGBU1-CYC1$_{ter}$ URA3 2μ) | This study |
| IMX598 | MAT a ade2Δ::TDH3$_{pr}$-KlGBU1-CYC1$_{ter}$ | This study |

References:
Nijkamp et al., (2012) Microb Cell Fact 11: 36
Entian & Kötter, (2007) Meth Microbiol 36: 629-666

TABLE 3 primers

| Primer | Sequence 5' to 3' |
|---|---|
| pUG-RV | 5' GGGAGATCTCCGCCAAGCGAATTGAAGGACCGTGCGTAGAATGAAGAACATTAAGGGTTGTCGACCTGC 3' (SEQ ID NO: 134) |
| pUg-FW | 5' GGGTCTAGAATGACAAGAGGGTCGAACTCGCCTAAGTCGTAATTGAGTCCAGATCCACTAGTGGCCTATG 3' (SEQ ID NO: 135) |
| pDS-RV | 5' GGGTCTAGACCGCCAAGCGAATTGAAGGACCGTGCGTAGAATGAAGAACCTATATTACCCTGTTATCCCTAGCGTAACTTTAAGGGTTCTCGAGAGCTC 3' (SEQ ID NO: 136) |
| pDS-FW | 5' GGGAGATCTATGACAAGAGGGTCGAACTCGCCTAAGTCGTAATTGAGTCAGTTACGCTAGGGATAACAGGGTAATATAGCTGTTTAGCTTGCCTCGTCC 3' (SEQ ID NO: 137) |
| FK140 pUDI065 fw | 5' GTATCACGAGGCCCTTTC 3' (SEQ ID NO: 138) |
| SLT1_control_rv | 5' CAATTCAACGCGTCTGTGAG 3' (SEQ ID NO: 139) |

TABLE 3-continued primers

| Primer | Sequence 5' to 3' |
|---|---|
| KANMX4 fw | 5' TCTTTCCTGCGTTATCCC 3' (SEQ ID NO: 140) |
| FK105-MP1 | 5' CTCGGTGAGTTTTCTCCTTCAT 3' (SEQ ID NO: 141) |
| GBU1 forward primer | 5' CATCCGAACATAAACAACCATGAAGGTTGCAGGATTTATATTG 3' (SEQ ID NO: 142) |
| GBU1 reverse primer | 5' CAAGAATCTTTTTATTGTCAGTACTGATCAGGCTTGCAAAACAAATTGTTC 3' (SEQ ID NO: 143) |
| Backbone forward | 5' CAATATAAATCCTGCAACCTTCATGGTTGTTTATGTTCGGATG 3' (SEQ ID NO: 144) |
| Backbone reverse | 5' GAACAATTTGTTTTGCAAGCCTGATCAGTACTGACAATAAAAAGATTCTTG 3' (SEQ ID NO: 145) |
| GBU1-ADE2ko-CENPK-fw | 5' GTAAAATCGTTGGATCTCTCTTCTAAGTACATCCTACTATAACAATCAAGAAAAACAAGAAAATCGGACAAAACAATCAAGTATGCGCTGCAGGTCGACAACCCTTAATG 3' (SEQ ID NO: 146) |
| GBU1-ADE2ko-CENPK-rv | 5' GATGTAATCATAACAAAGCCTAAAAAATAGGTATATCATTTTATAATTATTTGCTGTACAAGTATATCAATAAACTTATATATTAGCCGCATAGGCCACTAGTGGATCTG 3' (SEQ ID NO: 147) |

TABLE 4

Plasmids used in this study.

| Plasmid | Characteristic | Reference |
|---|---|---|
| pAG426GPDccdB | 2µ ori URA3 TDH3$_{pr}$-ccdB-CYC1$_{ter}$ | (Alberti et al., 2007) |
| pUDE264 | 2µ ori URA3 TDH3$_{pr}$-KlGBU1-CYC1$_{ter}$ | This study |
| pDS1 | ori AmpR DR$^a$-I-SceI site-AgTEF2$_{pr}$-KanMX-AgTEF2$_{ter}$-I-SceI site-DR | |
| pDS8 | ori AmpR DR$^a$-I-SceI site-AgTEF2$_{pr}$-KlGBU1-AgTEF2$_{ter}$-I-SceI site-DR | This study |

$^a$DR Direct Repeat.
References:
Alberti et al., (2007) Yeast 24: 913-919

TABLE 5

Guanidinobutyrase activities measured in cell extracts of S. cerevisiae strains IME215 and CEN.PK113-7D grown in batch cultures with arginine as sole nitrogen source. The S. cerevisiae strains and IME215 were pre-grown in synthetic medium with glucose and ammonium as sole nitrogen source. B.D. denotes below detection limit, which was estimated at 0.005 µmol min$^{-1}$ mg$^{-1}$ protein. Data represent the average ± mean deviation of independent biological duplicate cultures.

| Strain | Description | Activity (µmol min$^{-1}$ mg protein$^{-1}$) |
|---|---|---|
| S. cerevisiae IME215 | MATa ura3-52 pUDE264 (TDH3$_{pr}$-KlGBU1-CYC1$_{ter}$ URA3). | 0.17 ± 0.006 |
| S. cerevisiae CEN.PK113-7D | MATa Prototrophic reference | B.D. |

FIGURE LEGENDS

FIG. 1. Overview of the key reactions in eukaryotic arginine metabolism. Thick lines indicate ureohydrolase reactions. EC 3.5.3.1: arginase, EC 4.1.1.17, ornithine decarboxylase, EC 2.6.1.13: ornithine aminotransferase, EC 1.5.1.2: pyrroline-5-carboxylate reductase, EC 1.5.99.8: proline dehydrogenase, EC 1.5.1.12: 1-pyrroline-5-carboxylate dehydrogenase, EC 2.6.1.-aminotransferase, EC 4.1.1.75 2-oxo acid decarboxylase, EC 1.2.1.54 gamma-guanidinobutyraldehyde dehydrogenase, EC 3.5.3.7 guanidinobutyrate, EC 2.6.1.19 GABA transaminase, EC 1.2.1.16 succinate-semialdehyde dehydrogenase.

FIG. 2. A—Alignment of guanidino-acid hydrolase (EC.3.5.3.7) amino acid sequences of Saccharomycotina yeasts. The amino acid sequences were aligned using Clustal W (V1.7). The amino acid residues conserved in all sequences are depicted with the * symbol. XP_456325: reference GBU1 from Kluyveromyces lactis NRRL Y-1140; XP_002498240: Zygosaccharomyces rouxii CBS 732; XP_716668: Candida albicans SC5314; XP_461566: Debaryomyces hansenii CBS767; EIF45280: Dekkera bruxellensis AWRI1499; BAO40383: Kluyveromyces marxianus DMKU3-1042; AADM01000201.1: Lachancea waltii NCYC 2644; XP_503530: Yarrowia lipolytica CLIB122; EFW95653.1: Ogataea parapolymorpha DL-1 (Hansenula polymorpha); XP_002552049: Lachancea thermotolerans CBS 6340 (Kluyveromyces thermotolerans CBS6340); XP_001523956: Lodderomyces elongisporus NRRL YB-4239; XP_001482640: Meyerozyma guilliermondii ATCC 6260 (Pichia guilliermondii ATCC6260); XP_004196483: Millerozyma farinosa CBS 7064 (Pichia sorbitophila); XP_001385334: Scheffersomyces stipitis CBS 6054 (Pichia stipitis CBS 6054); XP_003679661: Torulaspora delbrueckii CBS 1146; AACE03000003.1: Lachancea kluyveri NRRL Y-12651. The consensus sequence is presented under the sequence alignment and amino acid conserved in at least 50% of the sequences. Bold and underlined amino acid denote a conserved domains found in guanidino-acid hydrolase.

B—Weblogo (Schneider and Stephens (1990). Nucleic Acids Research 18, 6097-6100) representing the conserved guanidino acid hydrolase motives from the sequence alignment.

FIG. 3. GenBank entry of the *K. lactis* protein XP_456325.1.

FIG. 4. Alignment of bacterial guanidino-amide hydrolase (EC.3.5.3.11) amino acid sequences. A. The amino acid sequences were aligned using Clustal W (V1.7). The amino acid residues conserved in all sequences are depicted with the * symbol. NP_289508: *Escherichia coli*; WP_000105576: *Shigella flexneri*; YP_005016506: *Klebsiella oxytoca* KCTC 1686; YP_001337000: *Klebsiella pneumoniae* subsp. *pneumoniae* MGH 78578; YP_003614749: *Enterobacter cloacae* subsp. *cloacae* ATCC 13047; YP_001455807: *Citrobacter koseri* ATCC BAA-895; XP_004532666: *Ceratitis capitata*; WP_006734551: *Salmonella enterica*; AHE29794: *Burkholderia pseudomallei* NCTC 1317. B—Consensus sequence generated from the sequence alignment. The consensus sequence is presented under the sequence alignment and amino acid conserved in at least 50% of the sequences. Bold and underlined amino acid denote a conserved domains found in guanidino-amide hydrolase.

B—Weblogo representing the conserved guanidino amide hydrolase motives from the sequence alignment.

FIG. 5. GenBank entry of the *E. coli* protein (agmatinase) AAC75974.1.

FIG. 6. Vector 1 and 2 with all essential parts for the standard deletion cassette. The 400 base overlap in the selection marker KlGBU1 (indicated by a cross) is designed to recombine due to the homology.

Figure 7:
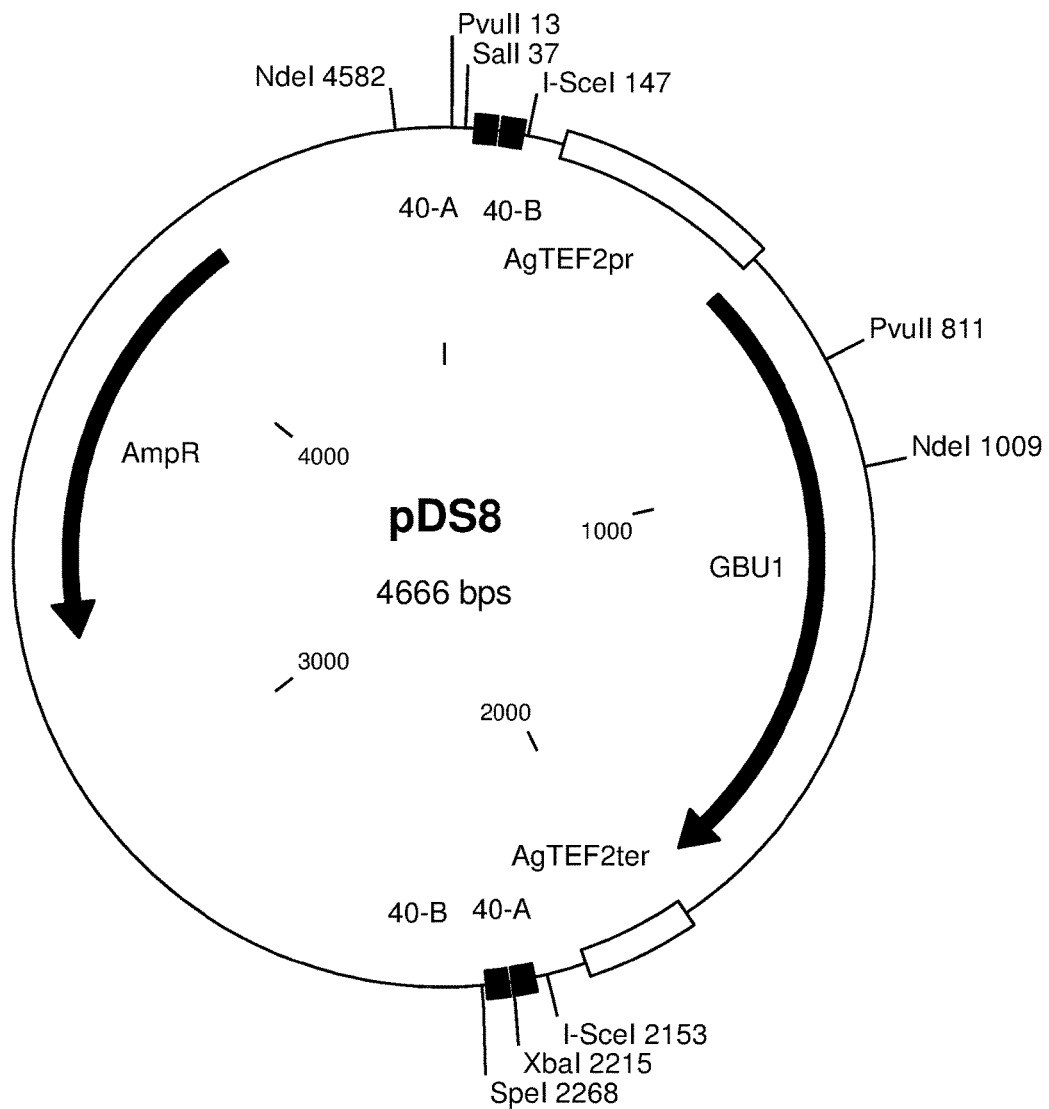

FIG. 7. Map of the plasmid pDS8 comprising the KlGBU1YM marker module.

Figure 8:
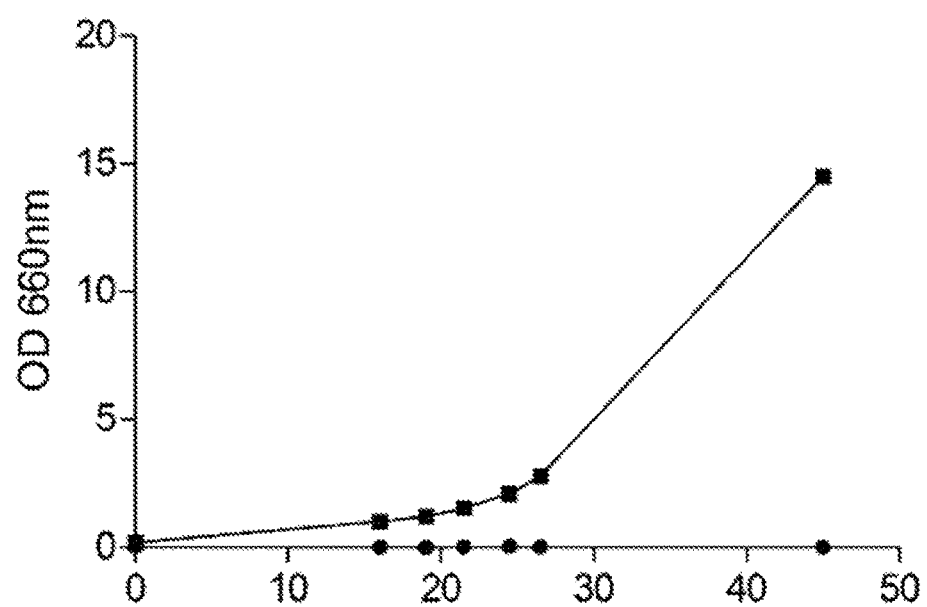

FIG. 8. Typical growth profile of *S. cerevisiae* strains on guanidinobutyrate: the *S. cerevisiae* strains CEN.PK113-7D (closed circle) and IME215 (TDH3$_{pr}$::KlGBU1::CYC1$_{ter}$) (closed square) were grown in shake flasks on glucose synthetic medium containing guanidinobutyrate as sole nitrogen source.

Figure 9:
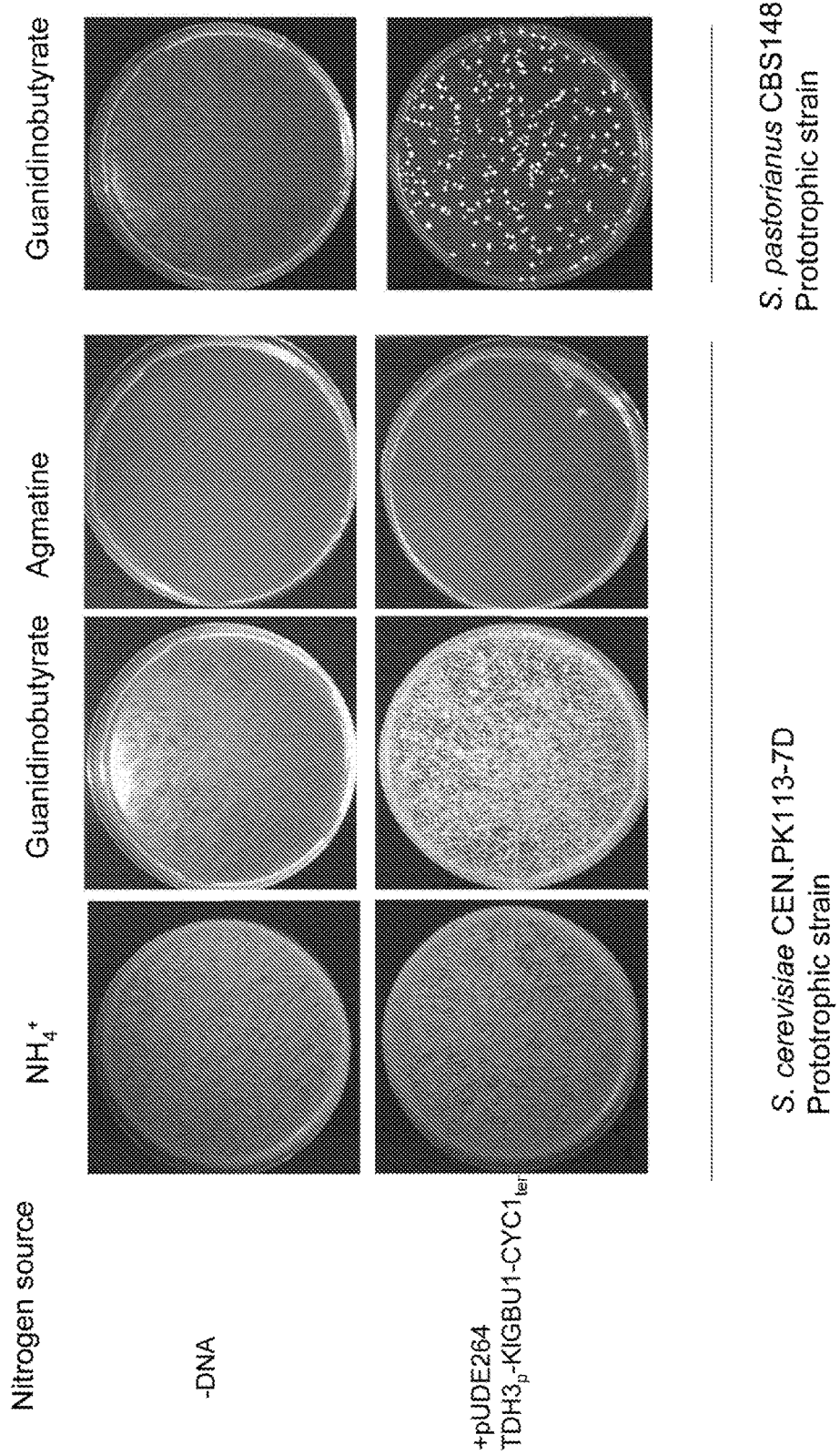

FIG. 9. Transformation of *S. cerevisiae* and *S. pastorianus* with pUDE264. The strains *S. cerevisiae* CEN.PK113-7D and *S. pastorianus* CBS1483 were transformed with the plasmid pUDE264 that carries the guanidinobutyrase gene from *K. lactis*. The transformed cells (50 µl) were plated on SM with different nitrogen sources ((NH$_4$)$_2$SO$_4$, guanidinobutyrate and agmatine). Untransformed strains (-DNA) were also plated on similar media as negative control.

FIG. 10. Examples of deletion cassettes. The deletion cassettes contain several regions: A—(1) a 50- to 80-bp sequence homologous to the upstream part of the gene to be deleted, including the start codon, and a 50- to 80-bp sequence homologous to the downstream part of the gene to be deleted, including the stop codon and (4) the selectable cassette which includes the *Ashbya gossypii* TEF2 promoter, the *K. lactis* GBU1 gene and the *A. gossypii* TEF2 terminator. B—In addition to the region (1) and (4) the deletion cassette includes (2) a 40-bp sequence flanked by (3) an I-SceI restriction site located upstream and downstream of the marker module.

EXAMPLES

Example 1

Materials and Methods
Strains and Maintenance

The *Saccharomyces cerevisiae* strains used in this study are listed in Table 2. The *S. cerevisiae* strains were constructed in the CEN.PK background (Nijkamp et al., (2012) Microb Cell Fact 11: 36; Entian & Kötter, (2007) Meth Microbiol 36: 629-666). Yeast strains that did not carry a plasmid were maintained on YPD medium (demineralized water; 10 g/L yeast extract; 20 g/L peptone; 20 g/L glucose). Yeast strains carrying plasmid were maintained on synthetic medium containing salts, trace elements and vitamins, prepared and sterilized as described previously (Verduyn et al., (1992) Yeast 8: 501-517) in which urea instead of ammonium sulfate was used when applicable. Culture stocks were prepared from shake flask cultures incubated at 30° C. and stirred at 200 rpm, by addition of 20% (v/v) glycerol and were stored at −80° C.

Media and Culture Conditions

Growth experiments were conducted in synthetic medium containing salts, trace elements and vitamins, prepared and sterilized as described previously (Verduyn et al., (1992) Yeast 8: 501-517). Glucose was added to a final concentration of 20.0 g/L. When ammonium sulfate was not the nitrogen source in the synthetic medium, it was replaced by guanidinobutyrate which was filter sterilized and added to sterile medium to concentrations of 2.9 g/L. Moreover, 3.3 g/L potassium sulfate was added to compensate for the removal of ammonium sulfate.

If required, 0.15 g/L uracil and/or 200 mg/L of G418 (Geneticin) were added to complete media. Selection agar plates were made by adding 20.0 g/L agar to these synthetic media.

Shake flask cultures were conducted in 500 ml or 250 ml shake flasks containing 100 ml or 20 ml of liquid medium respectively and incubated in an orbital shaker (New Brunswick Scientific, Edison, N.J.) at 200 rpm at 30° C.

Cloning and Overexpression of *K. lactis* KLLA0F27995g in *S. cerevisiae*.

Genomic DNA of the prototrophic reference strain *S. cerevisiae* CEN.PK113-7D was prepared as described previously (Burke et al., 2000. Cold Spring Harbor Laboratory. Methods in yeast genetics: a Cold Spring Harbor Laboratory course manual). ORF KLLA0F27995g (KlGBU1) was cloned from genomic DNA using Phusion Hot-Start polymerase (Finnzymes) and primers GBU1 forward primer/GBU1 reverse primer Table 3.

The PCR products was digested with SpeI and XhoI cloned into pAG426GPDccdB (Alberti et al., (2007) Yeast 24: 913-919; Table 4) preliminarily digested with the same enzymes, using T4 ligase (Life Technologies, Breda, The Netherlands) resulting in plasmid pUDE264. The plasmid pUDE264 was transformed in *S. cerevisiae* CEN.PK113-5D (ura3-52) using the LiAc method as previously described in (Gietz & Woods, (2002) Methods Enzymol 350: 87-96) resulting in strain IME215 (MATa ura3-52 pUDE264 (TDH3$_{pr}$-KlGBU1-CYC1$_{ter}$ URA3 2µ). The backbone plasmid pAG426GPD-ccdB was transformed in *S. cerevisiae* CEN.PK113-5D (ura3-52) using the LiAc method as previously described in (Gietz & Woods, (2002) Methods Enzymol 350: 87-96) resulting in strain IMZ312 (MATa ura3-52 pAG426GPD-ccdB (TDH3$_{pr}$-CYC1$_{ter}$ URA3 2µ).

Construction of the Plasmid pDS8

The KLLA0F27995g (KlGBU1) ORF was transferred from pUDE264 into pDS1 in place of the kanR gene. For the construction of the plasmid pDS1, the vector pUG6 (Guldener et al. (1996) Nucleic Acids Res 24:2519-24) was used as template for PCR using Phusion™ Hot Start II DNA Polymerase (Thermo Scientific, Waltham, Mass.) according to manufacturer's instructions and the primer pairs pUGfw/pUGrv to amplify the backbone of the vector and pDSfw/pDSrv to amplify the selection marker. The primer pUGfw contained the XbaI restriction site and a 40 bp synthetic sequence (repeat B) which was used to construct a 80 bp direct repeat. The primer pUGrv contained the BglII restriction site and another 40 bp synthetic sequence (repeat A) to construct the second 80 bp direct repeat. The primer pDSfw contained the BglII restriction site followed by to 40 bp B repeat. The primer pDSrv contained the XbaI restriction site and the 40 bp A repeat. All PCR's were visualized with gel electrophoresis. The fragments were isolated from agarose gel using Zymoclean™ Gel DNA Recovery Kit. (Zymo Research, Irvine, Calif.) The PCR fragments were restricted with XbaI and BglII and ligated with T4 DNA ligase (Thermo Scientific) according to manufacturer's instructions. Chemical competent *Escherichia coli*, strain DH5α, was transformed with the ligation mix and a correct colony was selected by PCR using the following primers FK140 pUDI065 fw, SLT1_control_rv, KANMX4 fw and FK105-MP1. The transfer of KlGBU1 in place of the kanR sequence was achieved by Gibson assembly (Gibson et al., (2009) Nat Methods 6: 343-345). The fragment carrying the KlGBU1 gene was PCR amplified using Phusion Hot-Start polymerase (Finnzymes) and primers GBU1-fw and GBU1-rv (Table 3). The plasmid pUDE264 was used as template. The backbone plasmid was PCR amplified using Phusion Hot-Start polymerase (Finnzymes) and primers Backbone-fw and Backbone-rv. The plasmid pDS1 was used as template. The two fragments shared at least 43 nucleotides identity at their flanks and were assembled in vitro using the Gibson assembly cloning kit from New England Biolabs (Ipswich, Mass.). The assembled mixture was transformed in *E. coli* DH5α and plated on LB plate containing ampicillin (100 mg/L). The assembled plasmid which contains the marker module KlGBU1YM was verified by restriction analysis and sequencing and a correct clone was named pDS8.

Deletion of ADE2 in *S. cerevisiae*.

Gene deletions in *S. cerevisiae* were performed by integration of the KlGBU1YM (SceI site::AgTEF2$_{pr}$-KlGBU1-AgTEF2$_{ter}$::SceI site) cassettes via the short-flanking-homology PCR method (Wach et al., (1994) Yeast 10: 1793-1808). Sequences of oligonucleotide primers are shown in Table 3. Deletion cassette for ADE2 was amplified using Phusion Hot-Start polymerase (Finnzymes, Landsmeer, The Netherlands) and the template plasmid pDS8 using primers GBU1-ADE2ko-CENPK-fw/GBU1-ADE2ko-CENPK-rv. The transformation of *S. cerevisiae* CEN.PK113-7D with the ADE2 deletion cassettes was performed using the LiAc method as previously described in (Gietz & Woods, (2002) Methods Enzymol 350: 87-96) resulting in strain IMX598.

Correct integration of the KlGBU1SY cassette and replacement of the gene of interest was, verified by diagnostic PCR using a forward primer specific for the 5' UTR (untranslated region) of ADE2 and the reverse primer for the deletion cassette (Table 3).

Preparation of Cell Extracts

For preparation of cell extracts, culture samples were harvested by centrifugation, washed twice with 10 mM potassium phosphate buffer (pH 7.5) containing 2 mM EDTA and stored at −20° C. Before cell disruption, samples were thawed at room temperature, washed, and resuspended in 100 mM potassium phosphate buffer (pH 7.5) containing 2 mM MgCl2 and 2 mM dithiothreitol. Extracts were prepared by sonication with 0.7 mm glass beads at 0° C. for 2 min at 0.5 min intervals with an MSE sonicator (Wolf Laboratories Limited, Pocklington, United Kingdom) (150 W output; 8 μm peak-to-peak amplitude) (Luttik et al., (2008) Metab Eng 10: 141-153). Unbroken cells and debris were removed by centrifugation at 4° C. (20 min; 36000×g). The resulting cell extract was used for enzyme assays.

Enzyme Activity Assays

For the arginase enzymatic assay 50 μL cell extract were activated in 950 μL manganese maleate buffer (50 mM manganese sulfate, 50 mM maleic acid, pH 7) for 1 h at 37° C. (Messenguy et al., (1971) Eur J Biochem 22: 277-286). The reaction mixture for arginase assays, prepared in dark eppendorf tubes, contained 60 μL of activated cell extract, 400 μL 713 mM arginine solution (pH 9.5) and demineralized water up to 1 mL. The reaction mixture was incubated for 30 min at 37° C. To stop the reaction, 0.7 mL sulfuric-phosphoric acid mixture (20% v/v concentrated sulfuric acid and 60% v/v syrupy phosphoric acid in demineralized water) was added to the reaction mixture. The amount of urea produced was quantified using the Archibald method (Archibald, (1945) J Biol Chem 157: 507-518) with a calibration line ranging from 0 until 0.6 mM of urea. 0.06 mL of a 4% v/v α-isonitroso-propiophenone in ethanol solution was added and samples were thoroughly mixed before boiling for 1 h in a 100° C. water bath to develop the color. The samples were cooled at room temperature for 15 min and the absorbance at 540 nm was measured in a Libra S11 spectrophotometer (Biochrom, Cambridge, United Kingdom).

The reaction mixture for guanidinobutyrase (GBU) enzyme assays was prepared in dark eppendorf tubes, containing in a 1 mL final volume: 50 mM glycine buffer (pH 9), 5 mM MnSO4 and 50 μL to 100 μL cell extract. The reaction was started by addition of 50 mM guanidinobutyric acid. After 30 min of incubation at 37° C., the reaction was stopped by addition of 700 μL of sulfuric-phosphoric acid mixture (20% v/v concentrated sulfuric acid and 60% v/v syrupy phosphoric acid in demineralized water). The amount of urea produced was quantified using the Archibald method (Archibald, 1945) with a calibration line ranging from 0 until 0.6 mM of urea. 0.06 mL of a 4% v/v α-isonitrosopropiophenone in ethanol solution was added and samples were thoroughly mixed before boiling for 1 h in a 100° C. water bath to develop the color. The samples were cooled at room temperature for 15 min and the absorbance at 540 nm was measured with a Libra S11 spectrophotometer (Biochrom).

Results

Expression of KlGBU1 in *S. cerevisiae* Confers the Ability to Grow on Guanidinobutyrate as Sole Nitrogen Source.

To characterize the function the *K. lactis* putative ureohydrolase gene, KLLA0F27995g was cloned under the control of the strong constitutive TDH3 promoter (TDH3pr) in an expression vector and transformed to *S. cerevisiae* (FIG. 8).

The expression plasmid pUDE264 was transformed in the laboratory strain CEN.PK113.7D (prototroph) and the wild brewing *Saccharomyces pastorianus* strain CBS1483 (www.cbs.knaw.nl/Collections/). The transformed cells were plated on synthetic medium containing either guanidinobutyrate or agmatine or ammonium sulfate. Expectedly, for both strains all transformants could grow on non-selective plates containing ammonium sulfate. In line with the enzyme measurements no transformants was rescued on agmatine plates whereas more than thousand and hundred transformants were detected on guanidinobutyrate plates for CEN.PK113-7D and CBS1483, respectively (FIG. 9). This demonstrated that KlGBU1 could be efficiently used as a dominant selectable marker in prototrophic strain of *S. pastorianus*.

Plasmids and Deletion Cassettes Construction.

The coding sequence of the *K. lactis* GBU1 gene, flanked by the *Ashbya. gossypii* TEF2 promoter and terminator, was cloned into the vector pDS1 by replacing the KanMX gene, resulting in the plasmid pDS8 (FIG. 7). The resulting KlGBU1YM module only contained heterologous sequences, thereby reducing the probability of mistargeted integration (Wach et al., (1994) Yeast 10: 1793-1808). The pDS8 plasmid can be easily used as template for deletion cassettes containing the new marker module KlGBU1YM and was used for the construction of all deletion cassettes used in this study.

The deletion cassettes contained three major regions (FIG. 10): (1) a 50- to 55-bp sequence homologous to the upstream part of the gene to be deleted, including the start codon, and a 50- to 55-bp sequence homologous to the downstream part of the gene to be deleted, including the stop codon. These regions were used for targeted homologous recombination (Baudin et al., (1993) Nucleic Acids Res 21: 3329-3330), (2) a 40-bp sequence flanked by (3) an I-SceI restriction site located upstream and downstream of the marker module and (4) the KlGBU1YM marker. Upon restriction by the endonuclease, homologous recombination of the direct repeat would be sufficient to pop-out and recycle the marker module.

Gene Deletion in *S. cerevisiae* Using KlGBU1YM

To evaluate whether the new marker KlGBU1YM was suitable for gene knock-out in *S. cerevisiae*, it was attempted to delete a gene in the laboratory strain CEN.PK113-7D. ADE2 was selected for this proof-of-principle experiment because the phenotype caused by ADE2 deletion can be visually screened, giving a fast preliminary evaluation of targeted integration. ADE2 codes for the enzyme phosphoribosylaminoimidazol carboxylase, which is involved in the biosynthesis of purine nucleotides. ade2 mutants require an external source of adenine and accumulate precursors of purine nucleotides in the vacuole which give colonies a red color (Zonneveld & van der Zanden, (1995) Yeast 11: 823-827).

The potential of KlGBU1YM as dominant marker was tested by transforming a deletion cassette to disrupt ADE2 in CEN.PK113-7D. After transformation, cells were grown on synthetic medium (SM) agar plates containing guanidinobutyrate as sole nitrogen source. Targeted gene deletion was confirmed by the inability of single colonies to grow on SM (in absence of adenine) and by PCR. The average transformation efficiency was 5 transformants per microg of DNA, with 100% of the colonies harboring the correct integration, and being able to grow on guanidinobutyrate as sole nitrogen source.

The material in the ASCII text file, named "Sequence-Listing-v3.txt", created Nov. 10, 2018, file size of 122,880 bytes, is hereby incorporated by reference.

The invention claimed is:

1. A set of constructs, comprising a first construct comprising a first part of a nucleotide sequence encoding a guanidinobutyrase, and a second construct comprising a second part of the nucleotide sequence encoding the guanidinobutyrase, whereby a fragment of the first part of the nucleotide sequence overlaps with a fragment that is present in the second part of the nucleotide sequence, allowing recombination between the first and second part of the nucleotide sequence, wherein the first construct further comprises a recognition site for an endonuclease and a first region of homology with a target genome of a microorganism, and the second construct further comprises a second region of homology with the target genome of the microorganism, and a copy of the endonuclease recognition site, whereby
   a coding sequence that encodes the endonuclease and which is coupled to an inducible promoter is present on the first or second construct; and
   a part of the first region of homology with the target genome on the first construct is duplicated between the copy of the endonuclease recognition site and the second region of homology with the target genome on the second construct; or a part of the second region of homology with the target genome on the second construct is duplicated between the first region of homology with the target genome and the endonuclease recognition site on the first construct.

2. The set of constructs according to claim 1, wherein the overlapping fragment of the nucleotide sequence encoding the selection marker is about 200 base pairs.

3. The set of constructs according to claim 1, wherein the duplicated region of homology with the target genome on the first and second construct is between 20 bp and 200 bp.

4. The set of constructs according to claim 3, wherein the duplicated region of homology is between 40 bp and 100 bp.

5. A method of culturing a microorganism selected from genera *Saccharomyces* sensu stricto, *Kazachstania*, *Naumovozyma*, *Nakaseomyces* and *Vanderwaltozyma* in the presence of guanidinobutyrate as sole nitrogen source, comprising:
   (a) introducing the set of constructs according to claim 1 into the microorganism, whereby the nucleotide sequence is operably linked to promoter and terminator sequences;
   (b) culturing the microorganism such that the nucleic acid molecule encoding the guanidinobutyrase is expressed in the microorganism; and
   (c) culturing the microorganism in the presence of guanidinobutyrate as sole nitrogen source.

6. The method according to claim 5, wherein said guanidinobutyrase-encoding nucleotide sequence encodes *Kluyveromyces lactis* NRRL Y-1140 hypothetical protein.

7. The method of claim 6, wherein the guanidinobutyrase-encoding nucleotide sequence encodes *Kluyveromyces lactis* guanidinobutyrase having SEQ ID NO: 148.

8. The method according to claim 5, wherein the promoter and/or terminator sequences are selected from a glycolytic gene.

9. The method according to claim 8, wherein the glycolytic gene is selected from PGI1, PFK1, PFK2, FBA1, TPI1, TDH1, TDH3, PGK1, GPM1, PYK1, ENO1, and ENO2.

10. The method of claim 5, wherein the encoded guanidinobutyrase comprises the conserved amino acid residues denoted with an asterisk in FIG. 2A.

11. A microorganism selected from genera *Saccharomyces* sensu stricto, *Kazachstania*, *Naumovozyma*, *Nakaseomyces* and *Vanderwaltozyma* that comprises a nucleotide sequence encoding a guanidinobutyrase.

12. The microorganism of claim 11, wherein the encoded guanidinobutyrase comprises the conserved amino acid residues denoted with an asterisk in FIG. 2A.

13. The microorganism according to claim 11, wherein said guanidinobutyrase-encoding nucleotide sequence encodes *Kluyveromyces lactis* NRRL Y-1140 hypothetical protein having SEQ ID NO: 148.

14. The microorganism of claim 13, wherein the guanidinobutyrase-encoding nucleotide sequence encodes *Kluyveromyces lactis* guanidinobutyrase having SEQ ID NO: 148.

15. A method for altering a genome in a microorganism selected from genera *Saccharomyces* sensu stricto, *Kazachstania*, *Naumovozyma*, *Nakaseomyces* and *Vanderwaltozyma*, comprising providing the set of constructs according to claim 1 to said microorganism, and selecting a microorganism in which the genome has been altered.

16. The method according to claim 15, wherein the microorganism is selected by culturing the microorganism in the presence of guanidinobutyrate as sole nitrogen source.

17. The method of claim 15, wherein the genome of the microorganism has been altered by insertion of a functional, recombined selection marker.

18. The method according to claim 17, wherein the microorganism is selected by culturing the microorganism in the presence of guanidinobutyrate as sole nitrogen source.

19. The method of claim 15, wherein the microorganism that is selected functionally expresses a guanidinobutyrase.

20. The method of claim 15, wherein a target gene is altered in the genome of said microorganism.

21. The method of claim 15, wherein the encoded guanidinobutyrase comprises the conserved amino acid residues denoted with an asterisk in FIG. 2A.

22. A kit comprising the set of constructs of claim 1.

* * * * *